(12) United States Patent
Chalekson et al.

(10) Patent No.: US 12,114,855 B2
(45) Date of Patent: Oct. 15, 2024

(54) FLEXIBLE SURGICAL STAPLER AND STAPLE INSERTION DEVICE

(71) Applicant: Tack Surgical, LLC, Solana Beach, CA (US)

(72) Inventors: Charles P. Chalekson, Templeton, CA (US); David G. Matsuura, Del Mar, CA (US); Philip J. Simpson, Escondido, CA (US); Nelson Siu, Encinitas, CA (US)

(73) Assignee: Tack Surgical, LLC, Solana Beach, CA (US)

( * ) Notice: Subject to any disclaimer, the term of this patent is extended or adjusted under 35 U.S.C. 154(b) by 0 days.

(21) Appl. No.: 17/849,157

(22) Filed: Jun. 24, 2022

(65) Prior Publication Data

US 2022/0409200 A1 Dec. 29, 2022

Related U.S. Application Data

(60) Provisional application No. 63/214,706, filed on Jun. 24, 2021.

(51) Int. Cl.
*A61B 17/064* (2006.01)
*A61B 17/00* (2006.01)

(52) U.S. Cl.
CPC ............. *A61B 17/0644* (2013.01); *A61B 2017/00004* (2013.01); *A61B 2017/0645* (2013.01)

(58) Field of Classification Search
CPC .................................................. A61B 17/0644
See application file for complete search history.

(56) References Cited

U.S. PATENT DOCUMENTS

| 5,785,713 A * | 7/1998 | Jobe ................. A61B 17/68 606/151 |
| 8,894,669 B2 * | 11/2014 | Nering ............. A61B 17/0682 606/151 |
| 9,370,356 B2 * | 6/2016 | Euteneuer ........... A61F 2/0811 |
| 10,016,198 B2 * | 7/2018 | Morgan ............. A61B 17/0682 |
| 2005/0288689 A1 * | 12/2005 | Kammerer ......... A61B 17/0469 606/142 |
| 2012/0085809 A1 * | 4/2012 | Milo .................. A61B 17/0644 227/181.1 |
| 2012/0211543 A1 * | 8/2012 | Euteneuer ........ A61B 17/07207 227/175.1 |
| 2014/0276968 A1 * | 9/2014 | Miksza ................. A61B 50/20 606/139 |
| 2017/0252036 A1 * | 9/2017 | Palmer ............... A61B 17/8685 |
| 2017/0281157 A1 * | 10/2017 | Hartdegen ......... A61B 17/0642 |

* cited by examiner

*Primary Examiner* — Nathaniel C Chukwurah
(74) *Attorney, Agent, or Firm* — Ice Miller LLP

(57) ABSTRACT

The present invention relates to tissue approximation and fixation, and surgical staples and staple placement devices for surgery. The present invention includes surgical staples having solid first and second legs for anchoring into respective tissue portions, and an elastically deformable bridge monolithically formed with the first leg and the second leg, the legs each forming respective angles greater than 90 degrees with respective portions of said elastically deformable bridge. The present invention also includes staple insertion device comprising a handle portion and substantially parallel insertion portions extending from the handle, the insertion portions each having an interior lateral channel, and each insertion portions having a terminal point.

10 Claims, 84 Drawing Sheets

FLEXIBLE SURGICAL STAPLER AND STAPLE INSERTION DEVICE

RELATED APPLICATION DATA

This application claims the priority benefit of U.S. Provisional Application Ser. No. 63/214,706, filed Jun. 24, 2021, which is hereby incorporated in its entirety herein by reference.

FIELD OF THE INVENTION

The present invention relates to tissue approximation and fixation, and surgical staples and staple placement devices for surgery and the like.

BACKGROUND OF THE INVENTION

In human and veterinary surgery, closure of the surgical site can be quite challenging and influential upon the overall outcome of the procedure. For example, many open and laparoscopic surgeries involve closure across multiple layers, or "levels" of tissue. The manner in which this closure is performed can be critical to a successful outcome and prevention of complications.

The most effective approaches to multi-level closure involve carefully crafted approximations involving a variety of fixation techniques and devices. They are often not performed to the full extent possible due to their: (1) intensive time requirement; (2) difficulty of using traditional sutures in certain tissue layers; and (3) limited options in terms of device alternatives to sutures.

Securing and closing multiple layers can easily occupy 50% of surgical times in specialties such as plastic surgery and other specialties.

Even when they are performed, they are susceptible to significant failure, as they often involve somewhat precarious arrangements. For example, a continuous running suture might cause an entire tissue plane to lose securement suffer from even a single point along its course fails. Certain tissue planes do not accept traditional needle and suture material well, such as fat, loose areolar tissue planes and muscle. There is significant desire to close these planes and to remove dead space, but upon suturing, the material tears through resulting in very poor ability to atraumatically and successfully reinforce these sites which can result in significant scarring.

Closure issues are also seen in intradermal closure, which affects all surgical specialties. Dermis is the one layer that all surgeons close. As mentioned above, running suture potentially compromises the entire incision. Other closure device options are bulky, have a tendency to extrude from the body prematurely, and are imprecise.

In contrast, discontinuous securement in which sections of tissue are connected but individually locked in place allow for discrete and differential tensioning. This allows the surgeon to set more accurate, exacting, and reliable points of closure across multiple levels of tissue.

Multiple layer closure further decreases tension on all other closure locations, resulting in less dehiscence, better soft tissue support [with maintenance of tissue positioning], and better scar outcomes. In addition, it can mitigate seroma and fluid accumulation, reducing or eliminating the need for surgical drains.

Surgical procedures can result in creation of a void around tissues that normally have direct contact and adherence with other tissues. The primary medical concern with respect to this void, also referred to as "dead space" is that fluid, or sometimes gas, can collect within this space. A seroma is the collection of fluid within this potential space. Seromas most often occur at a surgical site where tissue has been intentionally elevated. Friction between these elevated layers, trauma to the tissue or an inflammatory response to foreign bodies [such as implants or mesh] may result in further production of this undesirable fluid.

Seromas can cause discomfort, damage surrounding tissue, compromise normal healing, create a substrate for infection, and cause troublesome aesthetic issues.

One option to decrease the risk is the placement of surgical drains, which may be left in place anywhere from a few days to multiple weeks. They require significant maintenance, are painful, and are mostly, but not completely effective at draining any fluid moving into the space. Drains do not prevent the production of fluid.

One option to close and remove dead space is the placement of internal quilting sutures at the time of surgery. This entails the closure of elevated tissue planes with a large number of meticulously placed sutures to close and obliterate dead space, preventing friction and establishing contact to minimize fluid production. In this spirit, post-surgical compression garments applied to stabilize the tissue to limit edema and fluid production. In addition, the surgeon may frequently place one or more drainage tubes at the site.

Nonetheless, swelling and fluid can collect either immediately or in delayed fashion, even many weeks after surgery. This can result in additional comorbidity, medical cost, and procedures for the patient, even jeopardizing the procedure success itself.

Procedures prone to seromas and for which drains are commonly used are numerous but are most frequently seen in both plastic surgery and general surgery. Surgeries that involve elevation and undermining of larger amounts of tissue tend to have higher risks toward seromas.

Some examples include breast surgeries such as lumpectomies, mastectomies, reductions, abdominoplasties, body lift procedures, hernia repairs, lymph node removal, tumor resections, and manipulation of major organs.

There are major costs and complications associated with post-surgical management of dead space and typically involve seromas, infection, and hematomas or other bleeding. Serious or long-term problems related to a seroma are regarded as infrequent but can be costly, time-consuming, and require additional surgery and treatment.

However, there remains a need for efficient and effective tissue approximation in order to best reduce seroma formation, as well as to reduce or eliminate the need for draining.

SUMMARY OF THE INVENTION

The present invention includes a surgical staple adapted to be anchored into tissue, the suture comprising: (a) a flexible staple bridge of a flexible resorbable or other suture-like material; and (b) staple legs extending from the staple bridge and (c) one or more barbed anchor portion on the staple legs and shaped so as to resist the withdrawal from tissue once placed into tissue once the staple legs are inserted into tissue, the staple legs adapted to be moved from a relatively compressed state to a relatively expanded state, or from a relatively expanded state to a relatively compressed state.

The present invention also includes a surgical staple comprising: (a) a solid first leg for anchoring in a first tissue portion, a solid second leg for anchoring in a second tissue portion, and an elastically deformable bridge monolithically formed with the first leg and the second leg; the solid first leg and the solid second leg each forming a divergent angle, such as a respective angles greater than 90 degrees with respective portions of the elastically deformable bridge, the elastically deformable bridge of sufficient elasticity so as to permit the first leg and the second leg to be urged from an angled position to a substantially parallel position or beyond; and (b) each of the solid first leg and the solid second leg having a terminal end each comprising a distally directing point, such that, the solid first leg and the solid second leg have been urged into the substantially parallel position, the distally directing points are directed substantially orthogonal to the elastically deformable bridge; and each the terminal end having interior lateral sides comprising a lateral barb directed distally and to an angle to the respective leg.

The present invention further includes a surgical staple comprising: (a) a solid first leg for anchoring in a first tissue portion, a solid second leg for anchoring in a second tissue portion, and an elastically deformable bridge monolithically formed with the first leg and the second leg; the solid first leg and the solid second leg each forming a convergent angle forming respective angles less than 90 degrees with respective portions of the elastically deformable bridge, the elastically deformable bridge of sufficient elasticity so as to permit the first leg and the second leg to be urged from an angled position to a substantially parallel position; each of the solid first leg and the solid second leg having a terminal end each comprising a distally directing point, such that, the solid first leg and the solid second leg have been urged into the substantially parallel position, the distally directing points are directed substantially orthogonal to the elastically deformable bridge; and each the terminal end having interior lateral sides comprising a lateral barb directed distally and to an angle to the respective leg.

The surgical staple of the present invention may be of any effective dimensions, but an average non-limiting range of dimensions (based on surgical application) are as follows: (a) the cross members or bridge portions of the staples may be in the range of from about 5 mm to about 10 mm wide with a cross section in the range of from about 0.5 mm (round or rectangular) to about 1.5 mm; (b) the length of the legs including the barbs may be in the range of from about 3 mm to about 8 mm, and (c) the barb dimensions for the above range of staples and with varying shapes (length and width) may be in the range of from about 1 mm to about 4 mm.

The straight, shaped, pre-compressed, and tensioned staples are shown in FIGS. 1 thru 68b, including those that are delivered under tension and which expand or contract after release.

Also included are expandable arrows which can be actuated by applying tension to the suture after insertion in the tissue such as for use with the suture material in accordance with the use of the staples for tissue approximation.

The present invention also includes arrangements to address the movement of tissue in response to the insertion of the straight and or pre-tensioned staples.

The staples may be provided in stacked arrays such as through use of a frangible connection between adjacent staples, such as though any effective attachment means such as through the use of adhesives, co-molded structure, interferent structures or the like, so as to maintain the staple array within a cartridge structure.

The present invention also includes a device with a handle to allow the staples to be stored unstressed and then tensioned by tracks or mechanisms in the handle prior to delivery or release to facilitate intended function.

In one embodiment, each of the staples may have a plurality of barbs of sufficient number and length so as to resist the withdrawal once the staple is placed into a tissue.

The device of the present invention includes staple insertion device comprising: (a) a handle portion; (b) substantially parallel insertion portions extending from said handle, said insertion portions each having an interior lateral channel, and each insertion portions having a terminal point; the insertion portions adapted to slidingly engage a flexible staple, whether a straight staple, or a flexible staple that is adapted either to have its legs compressed and expand upon release from the device, or to have its legs expanded and compressed and upon release from the device.

The insertion portions may also be angled outward and may also be moveable between a relatively convergent position to a relatively divergent position.

The present invention also includes method of tissue approximation or attachment that may be carried out for example by using the handle portion of the described device and staple delivery portion (such as the insertion needles with or without a slider of driver) to place a surgical staple of the present invention.

This may be carried out such as may be described generally as using the handle portion with its sharp insertion portion for obtaining access to a tissue through its facing surface, in order to place a series of staples across or on either side of an incision or other tissue requiring approximation.

The insertion needle portions extending from the handle portion are extracted from the tissue leaving the surgical staple imbedded within the tissue.

In one variation, as the delivery portion may be served by a slider or driver that reciprocates within a channel and is retracted into the handle where it will engage with the staples in series and position the staple in a position to be deployed as the initial staple has been inserted and the device is moved to a subsequent location.

As the delivery portion (pusher) is retracted into the handle portion, it may conceivably engage with another surgical staple and position it ready to be deployed as described above. This would allow device to repeat the operation as described above a plurality of times, thus becoming a "multi-shot" surgical staple placement device.

Other variations to the invention include providing moving and pivoting needle insertion portion for facilitating tissue manipulation or approximation prior to delivery of the staple into the manipulated tissue.

A partial list of materials frequently used in medical equipment and devices of this type (other than metals, many are available as USP Class VI) may include:
  a. Metals:
  b. 300 Series Stainless Steel
  c. Titanium
  d. Nickel Titanium Alloys
  e. Aluminum
  f. Polymers:
  g. Polycarbonate (PC)
  h. Acrylonitrile butadiene styrene (ABS)
  i. ABS/PC Copolymers
  j. Acetyl (Delrin®, Celcon®)
  k. Modified Acrylics
  l. Polyether Ether Ketone (PEEK)
  m. Polypropylene (PP)
  n. Polyethylene (PE)
  o. Poly Vinyl Chloride (PVC)
  p. Polytetrafluoroethylene (PTFE)

q. Elastomers:
r. Thermoplastic Elastomers (TPE)
s. Thermoplastic Urethanes (TPU)
t. Fluoroelastomer (Viton®)
u. Silicone
v. Latex
w. Polyisoprene
x. Bio-absorbable:
y. Polydioxanone (PDS)
z. Polyglycolic Acid PGA
aa. Polylactic Acid (PLA)
bb. Poly-L-lactic Acid (PLLA)

These may be used to construct the insertion device and staples in accordance with methods of plastics molding and construction known and used in the art.

It will be appreciated that other embodiments, shapes, and configurations of the surgical staple placement device and surgical staple, as well as the accompanying suture material with associated arrows as described herein may be conceived using the basics of the handle portion, the insertion portion, the delivery portion (including the driver or slider), and the suture, while still retaining the basic concept of development, fixation, approximation, and tensioning. It will also be appreciated that can also be conceived that in other configurations of the surgical staple, alternately shaped barbs and the like may be attached, assembled or fixed to the surgical staple or to either or both ends of the surgical staple legs.

DETAILED DESCRIPTION OF THE PREFERRED EMBODIMENTS

Figure 1:
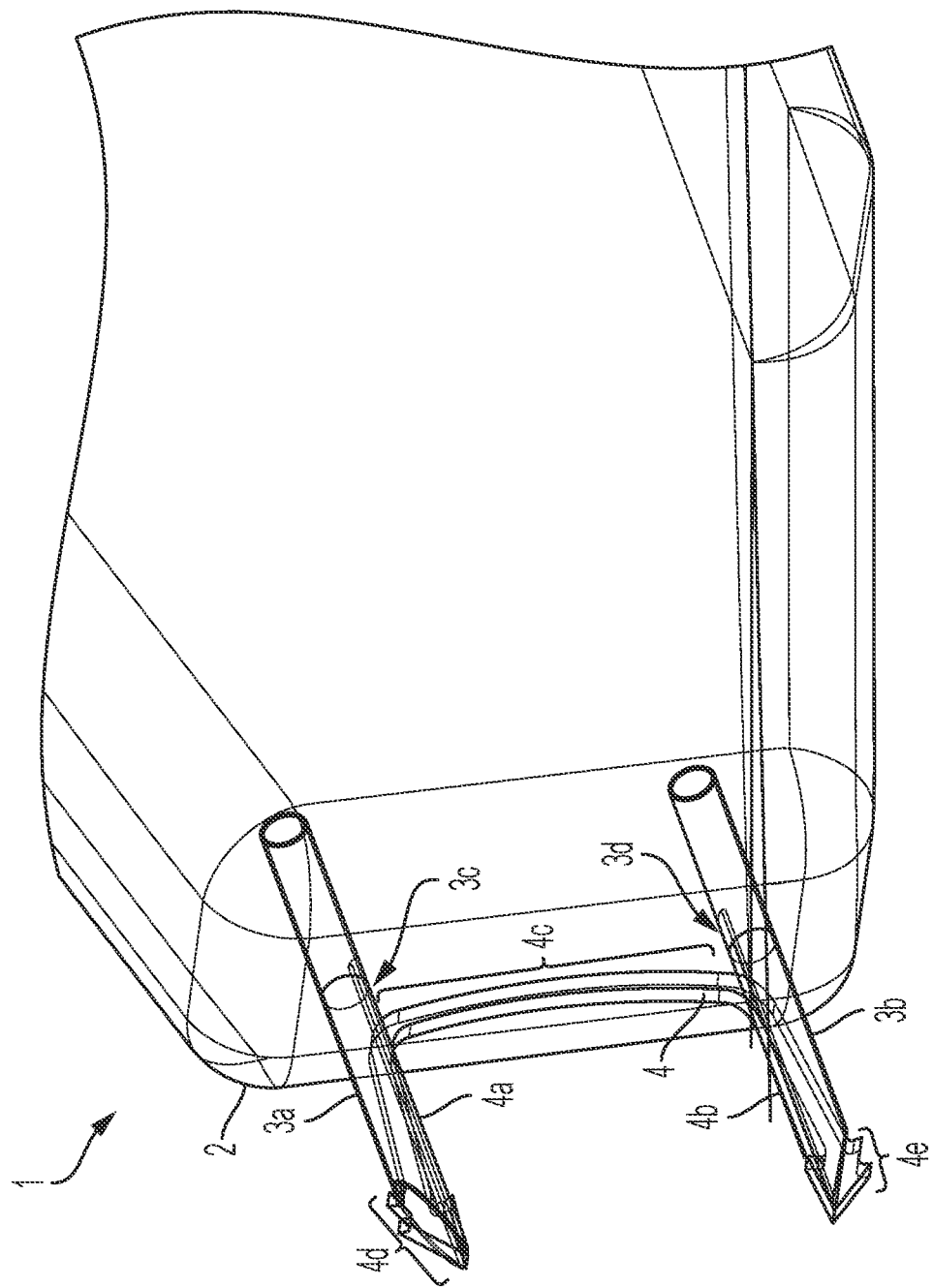
FIG. 1 shows a lateral perspective view of a flexible surgical staple and staple insertion device in accordance with one embodiment of the invention.

FIG. 1 shows a lateral perspective view of a flexible surgical staple and staple insertion device in accordance with one embodiment of the invention. FIG. 1 shows staple insertion device 1 comprising a handle portion 2 and insertion needle portions 3a and 3b having opposed channels 3c and 3d. Opposed channels 3c and 3d hold in sliding engagement flexible staple 4 by engaging staple legs 4a and 4b, while staple bridge portion 4c is held in a relatively compressed state such that the staple legs 4a and 4b are maintained aligned with respective insertion needle portions 3a and 3b. In this position the flexible staple is in a loaded compressed state so that it may be inserted into tissue at sufficient depth to approximate the tissue. Flexible staple legs 4a and 4b are provided with one or more outwardly directed barbs 4d and 4e that permit insertion while securing the flexible staple 4 in place in the tissue once the flexible staple 4 expands.

Figure 2:
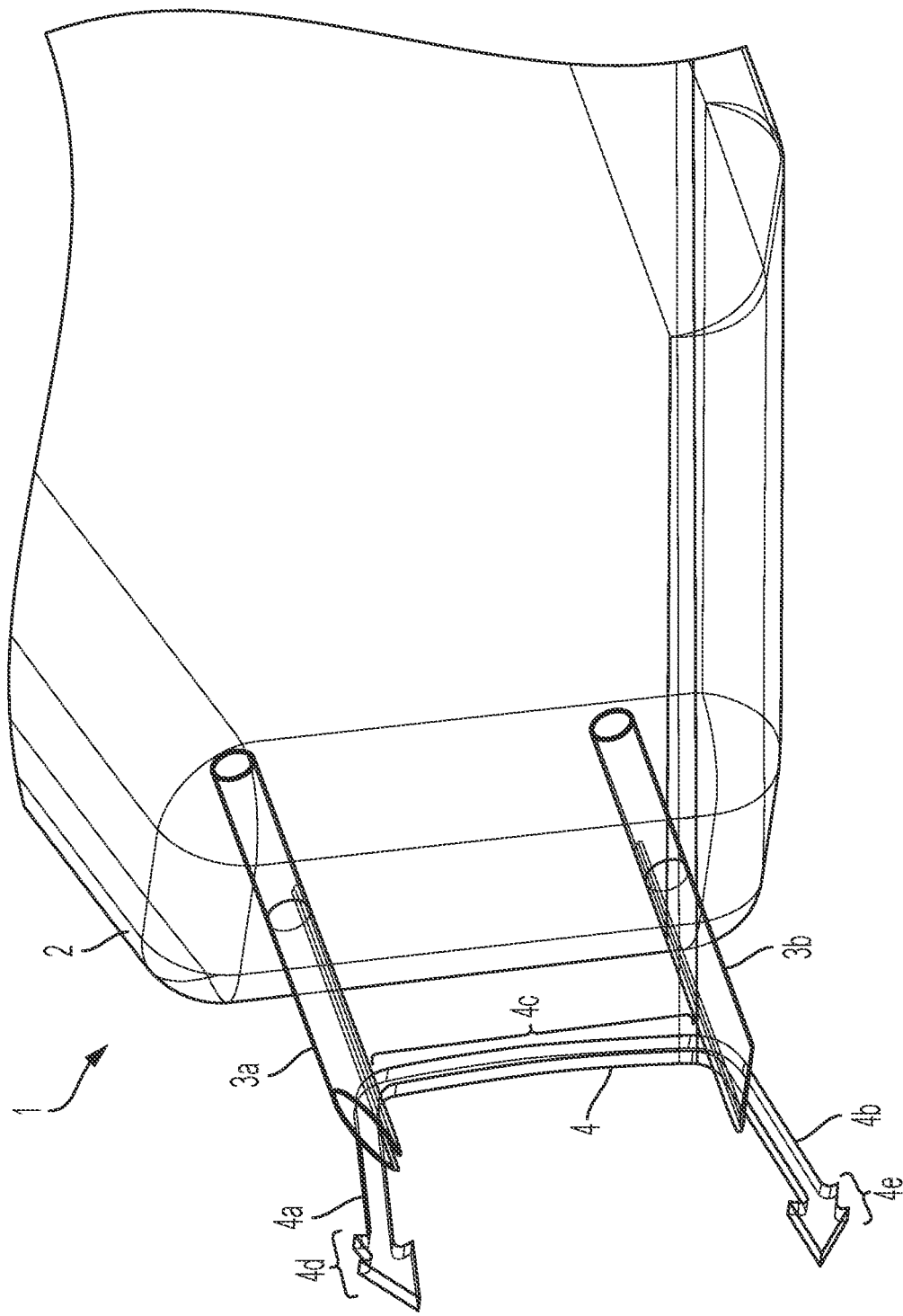
FIG. 2 shows a lateral perspective view of a flexible surgical staple and staple insertion device in accordance with one embodiment of the invention.

FIG. 2 shows a lateral perspective view of a flexible surgical staple and staple insertion device in accordance with one embodiment of the invention, and wherein like numerals refer to identified features. FIG. 2 shows flexible staple 4 as it is partially released from insertion needle portions 3a and 3b, and showing the lateral expansion of staple legs 4a and 4b as they are slid from respective insertion needle portions 3a and 3b permitting staple bridge portion 4c to decompress toward its uncompressed state, as the staple insertion device 1 is withdrawn from the tissue to be approximated.

Figure 3:
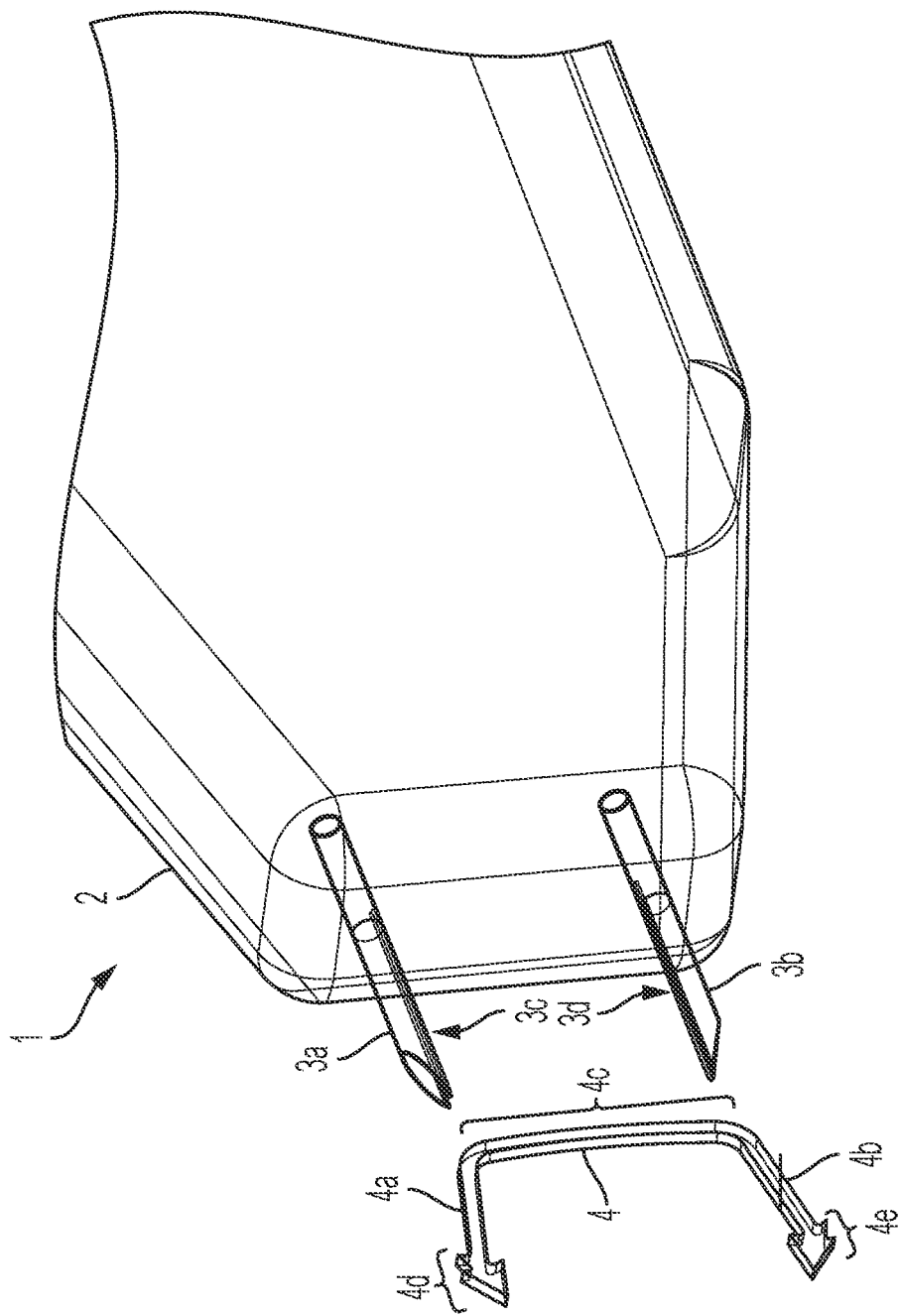
FIG. 3 shows a lateral exploded perspective view of a flexible surgical staple and staple insertion device in accordance with one embodiment of the invention.

FIG. 3 shows a lateral exploded perspective view of a flexible surgical staple and staple insertion device in accordance with one embodiment of the invention. FIG. 3 shows flexible staple 4 fully released from insertion needle portions 3a and 3b and showing the completed lateral expansion of staple legs 4a and 4b as staple bridge portion 4c is fully decompressed after having been inserted into tissue at sufficient depth to approximate the tissue.

Figure 4:
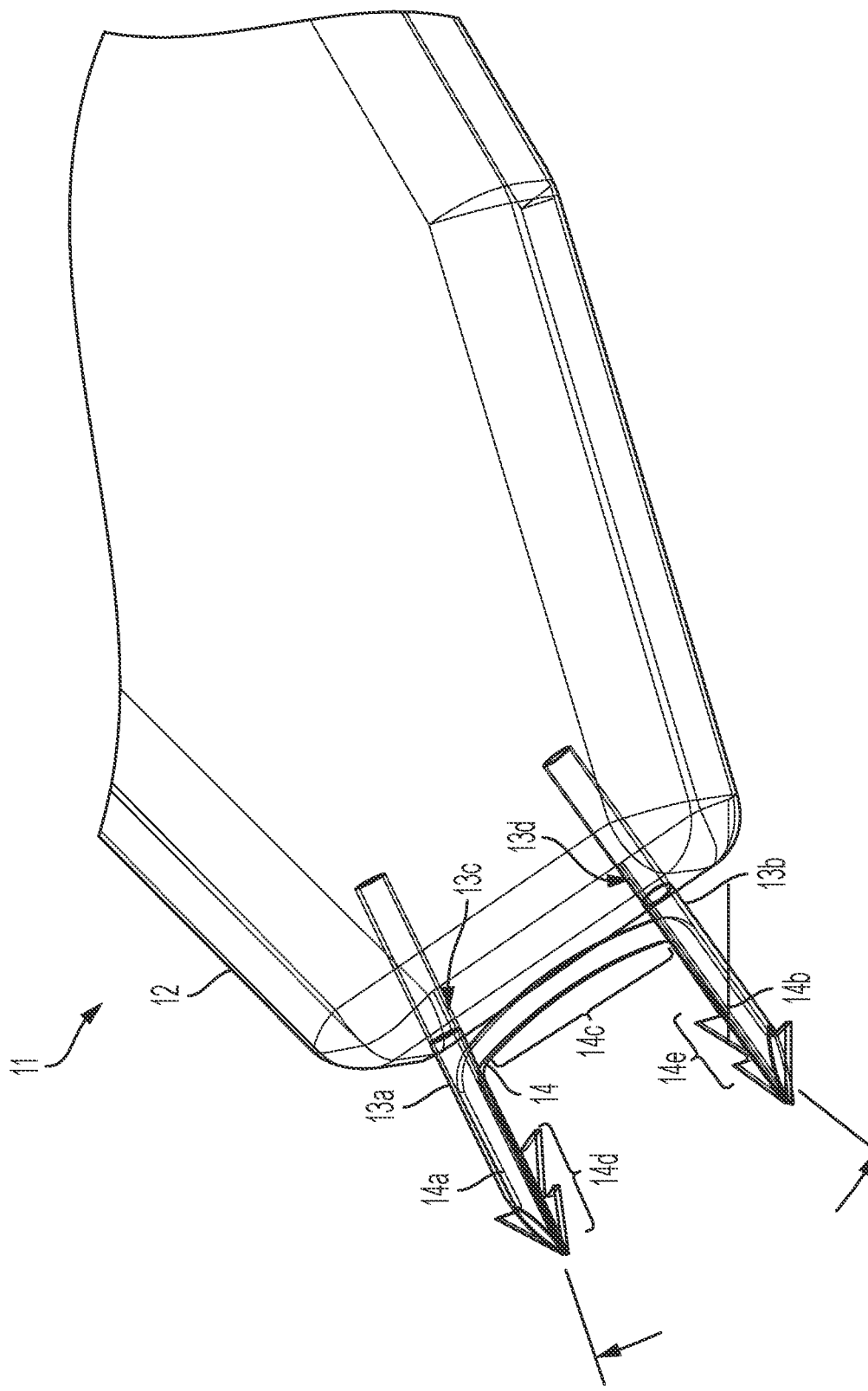
FIG. 4 shows a detailed lateral perspective view of a flexible surgical staple and staple insertion device in accordance with one embodiment of the invention.

FIG. 4 shows a detailed lateral perspective view of a flexible surgical staple and staple insertion device in accordance with another embodiment of the invention. FIG. 4 shows staple insertion device 11 similar to staple insertion device 1 and comprising a handle portion 12 and angled insertion needle portions 13a and 13b having opposed channels 13c and 13d. The angled insertion needle portions 13a and 13b assist in facilitating tissue approximation during insertion.

Opposed channels 13c and 13d hold in sliding engagement flexible staple 14 by engaging staple legs 14a and 14b, while staple bridge portion 14c is held in a relatively compressed state such that the staple legs 14a and 14b are maintained aligned with respective insertion needle portions 13a and 13b. In this position the flexible staple is in a loaded compressed state so that it may be inserted into tissue at sufficient depth to approximate the tissue. Flexible staple legs 14a and 14b are provided with one or more outwardly directed barbs 14d and 14e that permit insertion while securing the flexible staple 14 in place in the tissue once the flexible staple 14 expands.

Figure 5:
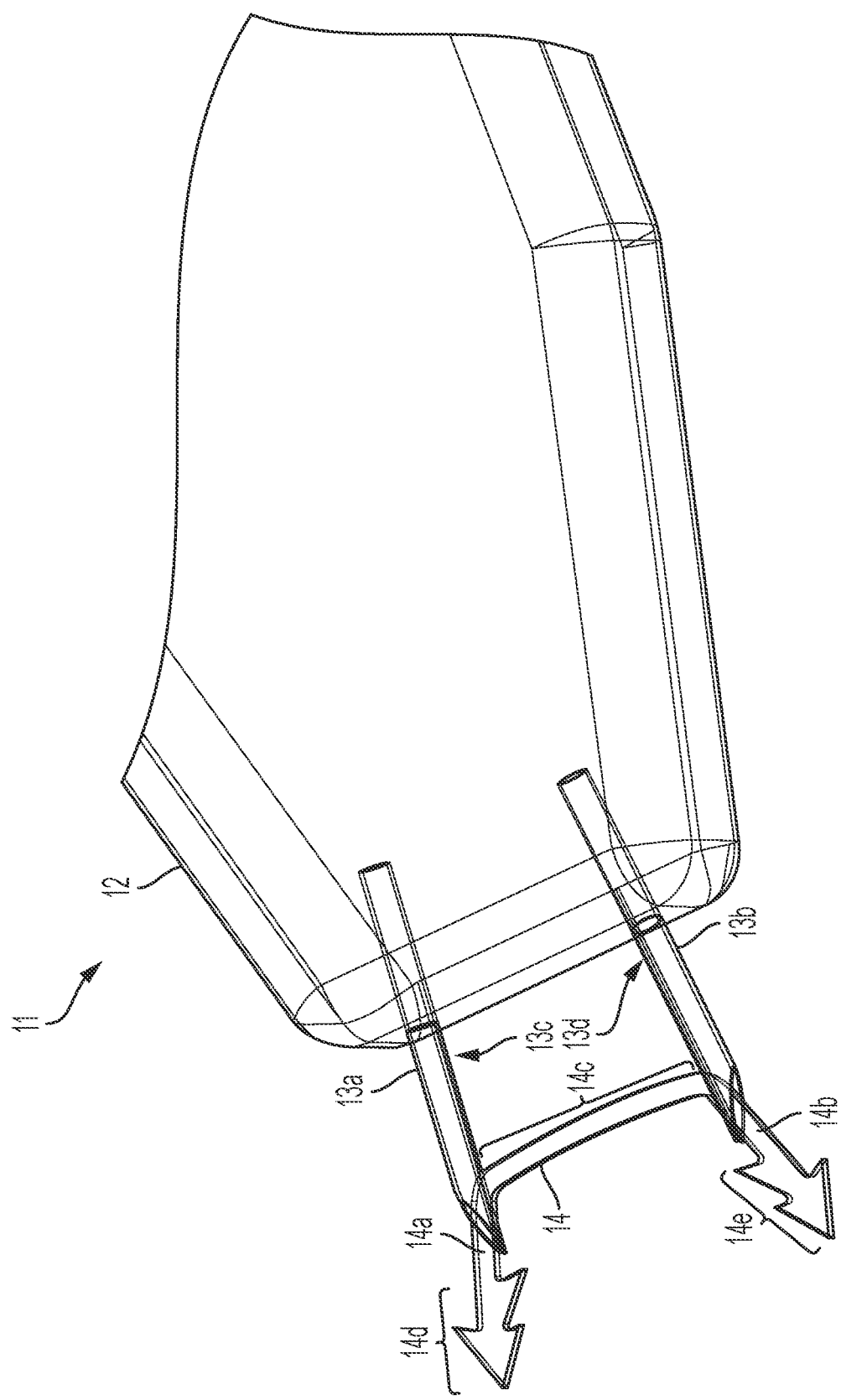
FIG. 5 shows a detailed lateral perspective view of a flexible surgical staple and staple insertion device in accordance with one embodiment of the invention.

FIG. 5 shows a detailed lateral perspective view of a flexible surgical staple and staple insertion device in accordance with the embodiment FIG. 4, and wherein like numerals refer to identified features. FIG. 5 shows flexible staple 14 as it is partially released from insertion needle portions 13a and 13b, and showing the lateral expansion of staple legs 14a and 14b as they are slid from respective insertion needle portions 13a and 13b permitting staple bridge portion 14c to decompress toward its uncompressed state, as the staple insertion device 11 is withdrawn from the tissue to be approximated.

Figure 6:
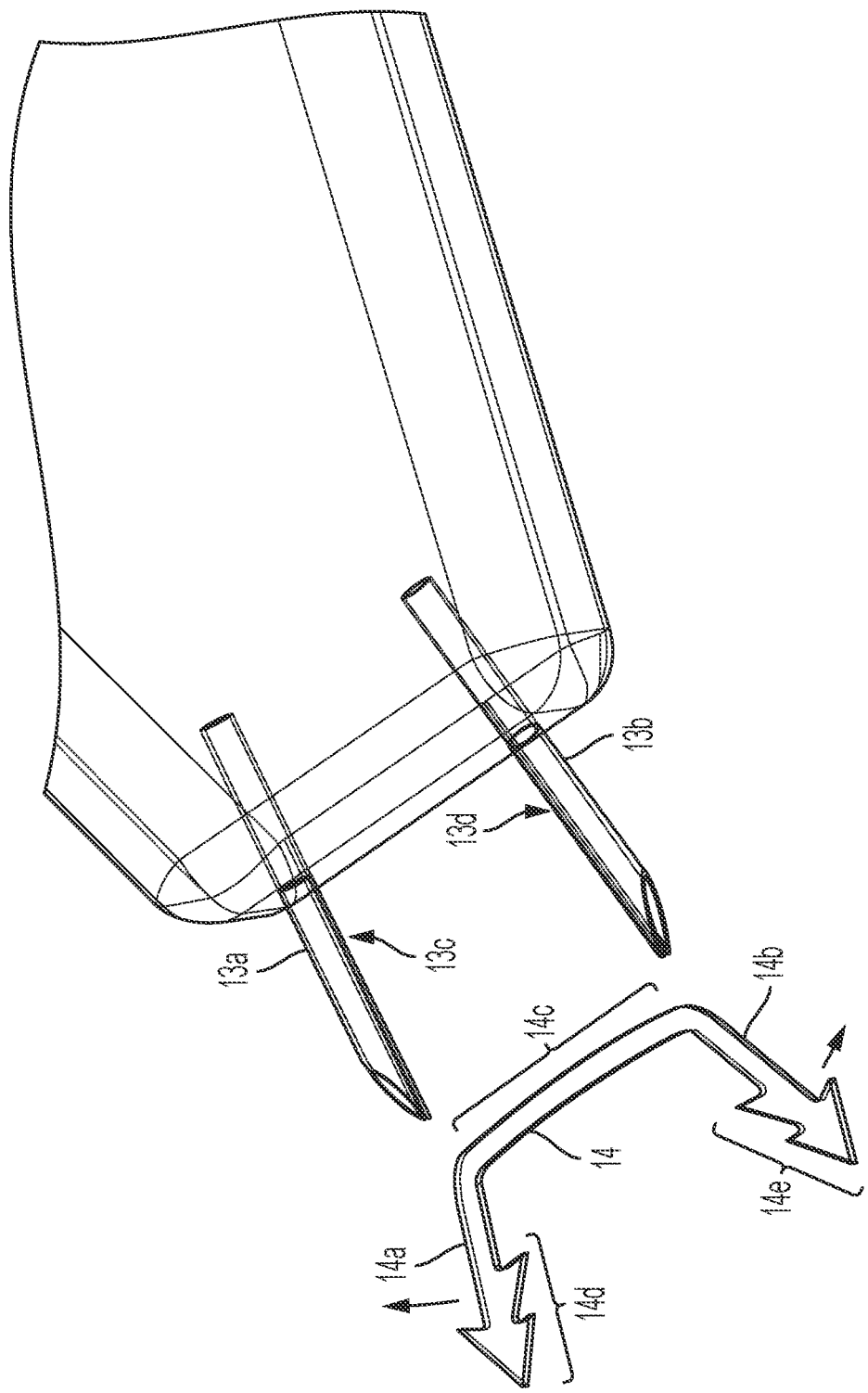
FIG. 6 shows a lateral exploded perspective view of a flexible surgical staple and staple insertion device in accordance with one embodiment of the invention.

FIG. 6 shows a lateral exploded perspective view of a flexible surgical staple and staple insertion device in accordance with the embodiment FIG. 4, and wherein like numerals refer to identified features. FIG. 6 shows flexible staple 14 fully released from insertion needle portions 13a and 13b and showing the completed lateral expansion of staple legs 14a and 14b as staple bridge portion 14c is fully decompressed after having been inserted into tissue at sufficient depth to approximate the tissue.

Figure 7:
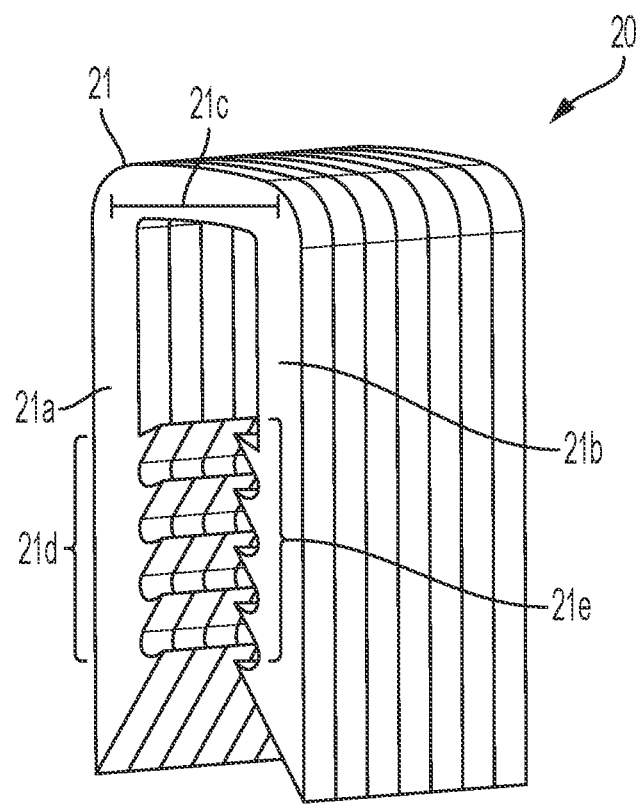
FIG. 7 shows a lateral perspective view of an assembled array of surgical staples in accordance with one embodiment of the invention.

FIG. 7 shows a lateral perspective view of an assembled array of flexible surgical staple in accordance with one embodiment of the invention. FIG. 7 shows surgical staple array 20 comprising a series of staples 21 each having staple legs 21a and 21b and staple bridge portion 21c. Flexible staple legs 21a and 21b are provided with one or more inwardly directed barbs 21d and 21e that permit insertion while securing the staple 21 in place in the tissue once the flexible staple 14 expands. The staple array 20 may be created by providing a frangible connection between adjacent staples, such as though any effective attachment means such as through the use of adhesives, co-molded structure, interferent structures or the like, so as to maintain the staple array within a cartridge structure or the like of a staple insertion device while permitting a staple driver to separate and drive each staple in series through hand force or equivalent actuator force. The staples of this embodiment may be rigid or flexible and in the case of flexible staples, the attachment means may be used to maintain the staples in a compressed state prior to serial release from the array, and while, once released, maintained in a compressed state during insertion such as through use of staple insertion devices 1 or 11 as described above.

Figure 8:
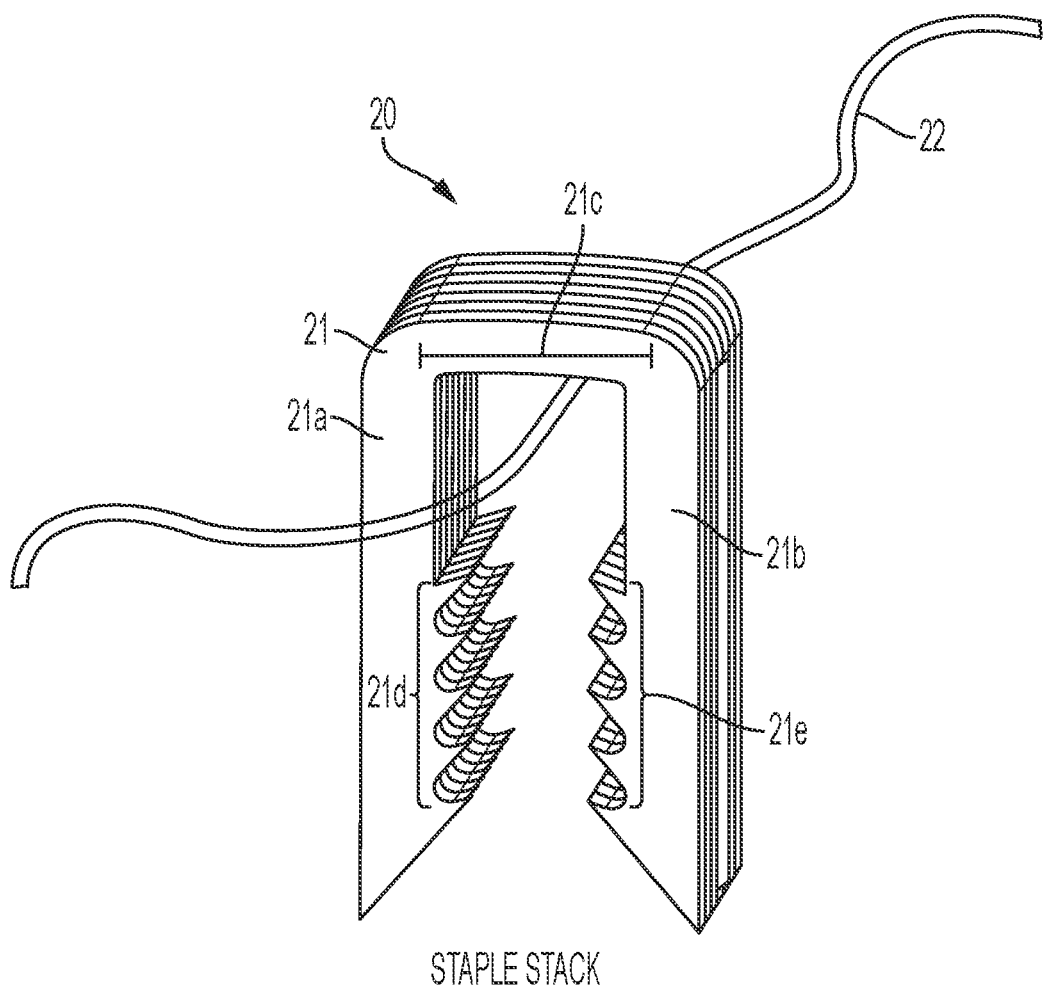
FIG. 8 shows a lateral perspective view of an assembled array of flexible surgical staple and a length of suture in accordance with one embodiment of the invention.

FIG. 8 shows a lateral perspective view of an assembled array of surgical staples and a length of suture in accordance with the embodiment FIG. 7, and wherein like numerals refer to identified features. FIG. 8 shows surgical staple array 20 comprising a series of staples 21 as described above, and with suture 22 disposed so as to extend through the staple array 20 so as to be captured and delivered such as from a suture supply (such as a spool incorporated into staple insertion devices 1 or 11 or the like), and so as to be co-deployed under each staple as inserted.

Figure 9:
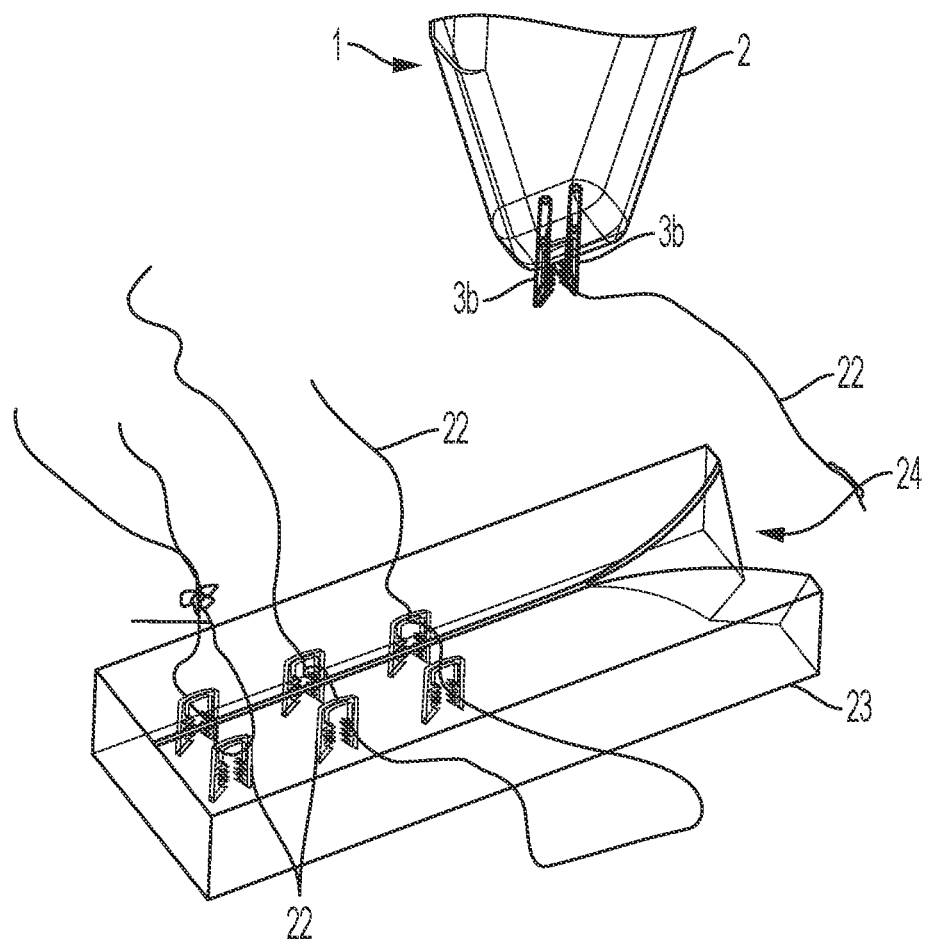
FIG. 9 shows a lateral perspective view of a flexible surgical staple and staple insertion device in accordance with one embodiment of the invention, positioned over a schematic of an approximated tissue having staples placed therein.

FIG. 9 shows a lateral perspective view of a surgical staple and staple insertion device in accordance with one embodiment of the invention, positioned over a schematic of an approximated tissue 23 having some staples 21 placed therein. FIG. 9 shows a schematic of tissue 23 having an incision or other tissue separation 24 requiring approximation. This Figure shows how staple 21 and suture 22 may be co-deployed using, for instance staple insertion device 1 as described above for deploying staple 21 individually or from surgical staple array 20 contained by a cartridge within staple insertion device 1. The staples 21 may be placed on opposite sides of the tissue separation 24, and lengths of suture 22 may through this method be captured beneath staples 21, and free ends may be knotted to maintain the tissue in the approximated position.

Figure 10:
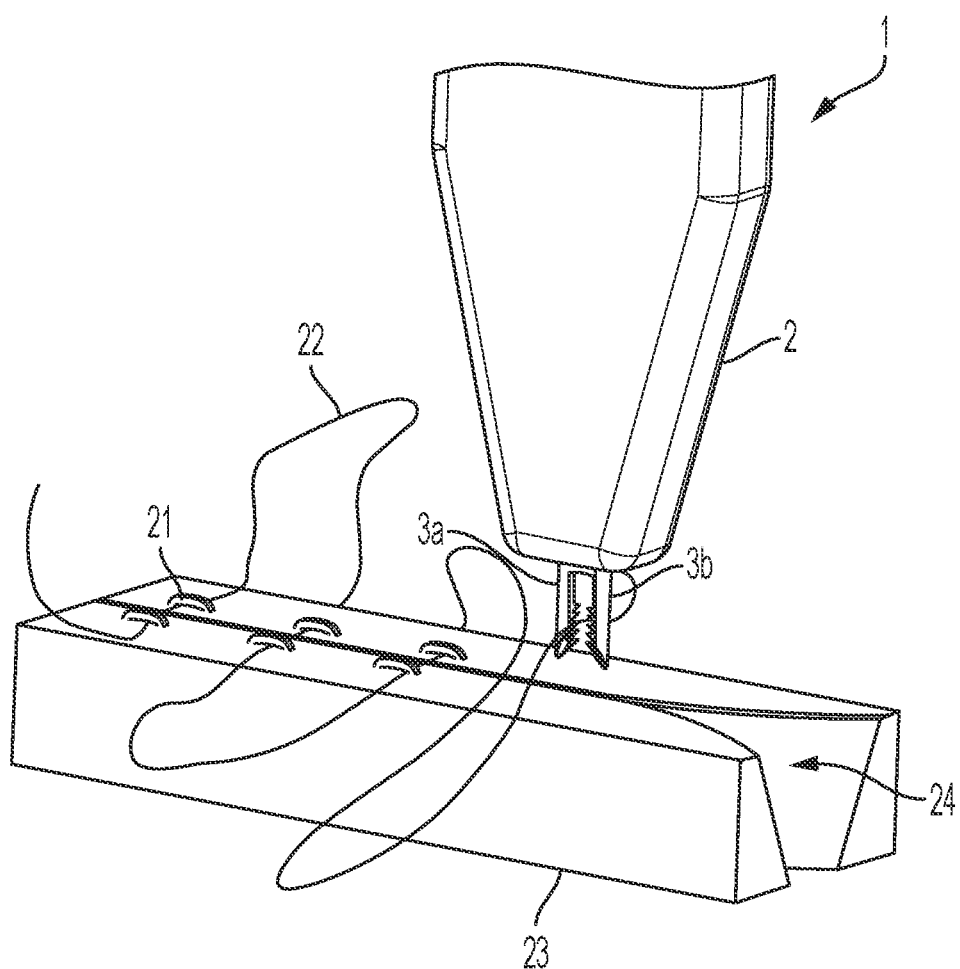
FIG. 10 shows a lateral perspective view of a flexible surgical staple and staple insertion device in accordance with one embodiment of the invention, positioned over a schematic of an approximated tissue having staples placed therein.

FIG. 10 shows a lateral perspective view of a surgical staple 21 and staple insertion device 1 in accordance with one embodiment of the invention as shown in FIG. 9, and wherein like numerals refer to identified features. This Figure shows staple insertion device 1 positioned over a schematic of an approximated tissue 23 having some staples 21 already placed therein to secure the approximated tissue separation 24. This Figure similarly shows how the lengths of suture 22 may be captured beneath staples 21, and free ends may be knotted to maintain the tissue in the approximated position.

Figure 11:
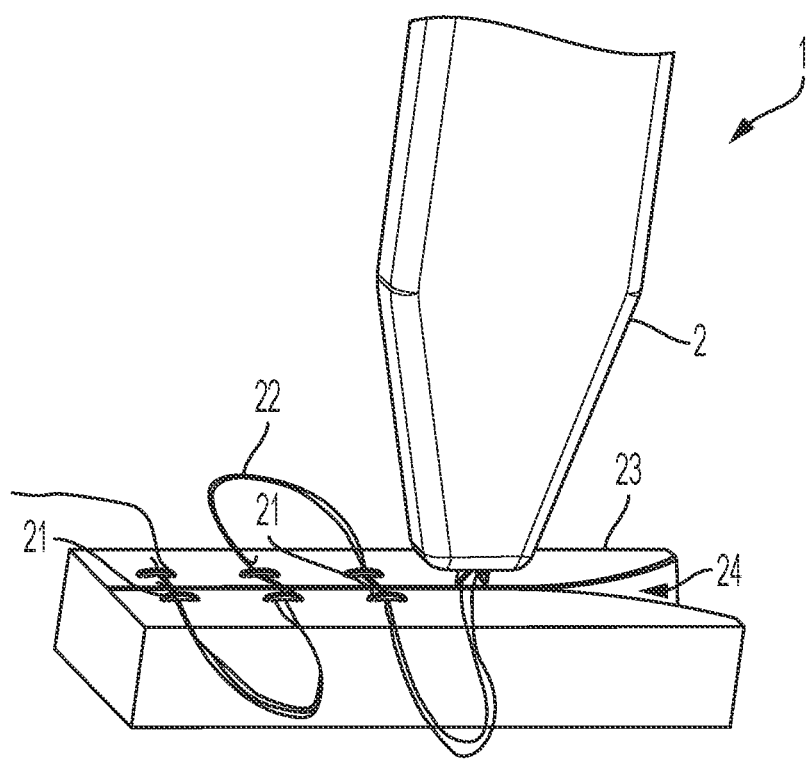
FIG. 11 shows a lateral perspective view of a flexible surgical staple and staple insertion device in accordance with one embodiment of the invention, positioned over a schematic of an approximated tissue having staples placed therein.

FIG. 11 shows a lateral perspective view of a surgical staple 21 and staple insertion device 1 in accordance with one embodiment of the invention as shown in FIG. 9, and wherein like numerals refer to identified features. This Figures shows staple insertion device 1 positioned so as to insert a staple 21 into an approximated tissue 23 having staples 21 placed therein. This Figure similarly shows how the suture 22 may be captured beneath staples 21, so as to provide a continuous loop of suture 22 woven through a series of staples 21 fixed in the tissue and maintaining the suture beneath them. Following insertion of the staples 21, the suture loop may be tightened and knotted to secure the approximated tissue.

Figure 12:
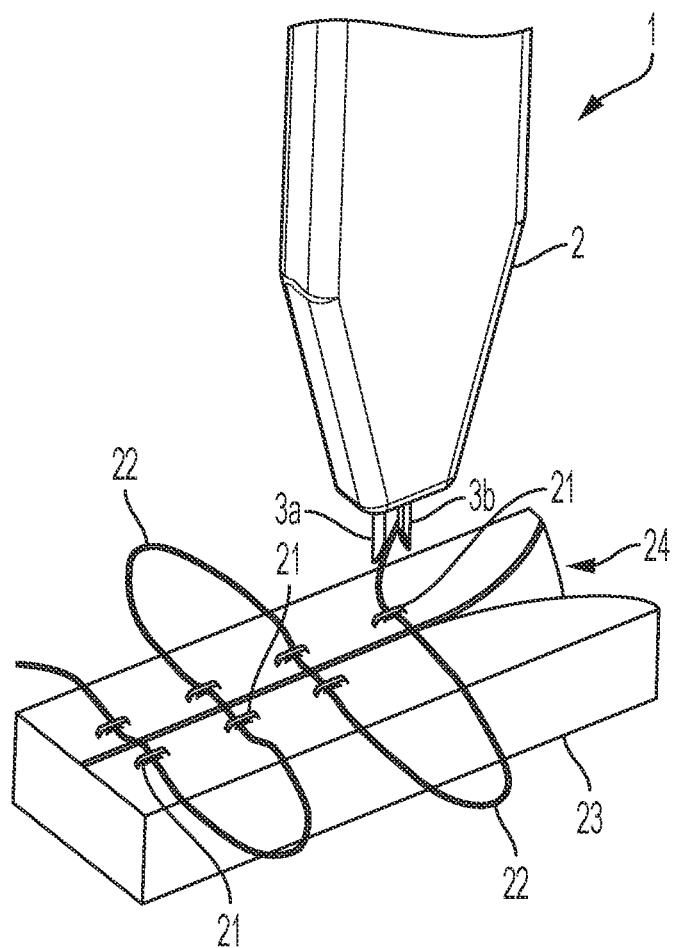
FIG. 12 shows a lateral perspective view of a flexible surgical staple and staple insertion device in accordance with one embodiment of the invention, positioned over a schematic of an approximated tissue having staples placed therein.

FIG. 12 shows a lateral perspective view of a surgical staple 21 and staple insertion device 1 in accordance with one embodiment of the invention as shown in FIG. 9, and wherein like numerals refer to identified features. This Figure shows the staple insertion device 1 having been withdrawn from approximated tissue 23 having placed and released one of the staples 21 therein so as to capture suture 22 beneath staple 21, leaving a continuous loop of suture 22 woven through the series of staples 21 fixed in the tissue and maintaining the suture beneath them, after which the suture loop may be tighten and knotted to secure the approximated tissue.

Figure 13:
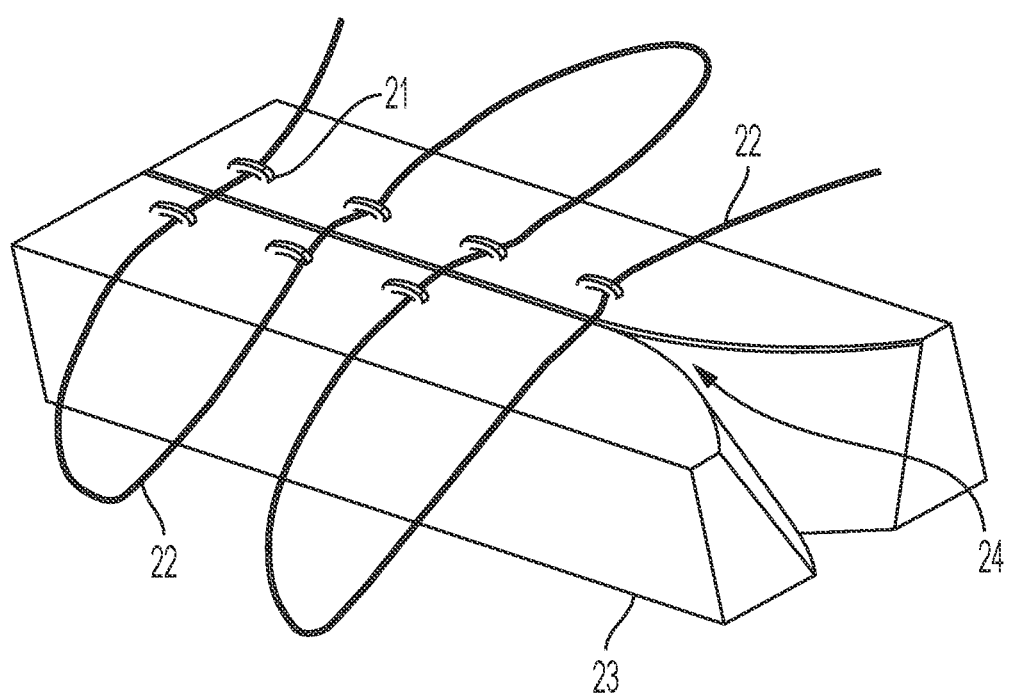
FIG. 13 shows a lateral perspective view of a schematic of an approximated tissue having staples placed therein.

FIG. 13 shows a lateral perspective view of a schematic of an approximated tissue 23 having staples 21 placed therein, with the suture 22 captured beneath staples 21, so as to provide a continuous loop of suture 22 woven through a series of staples 21 fixed in the tissue 23 and maintaining the suture beneath them and close approximated tissue separation 24.

Figure 14:
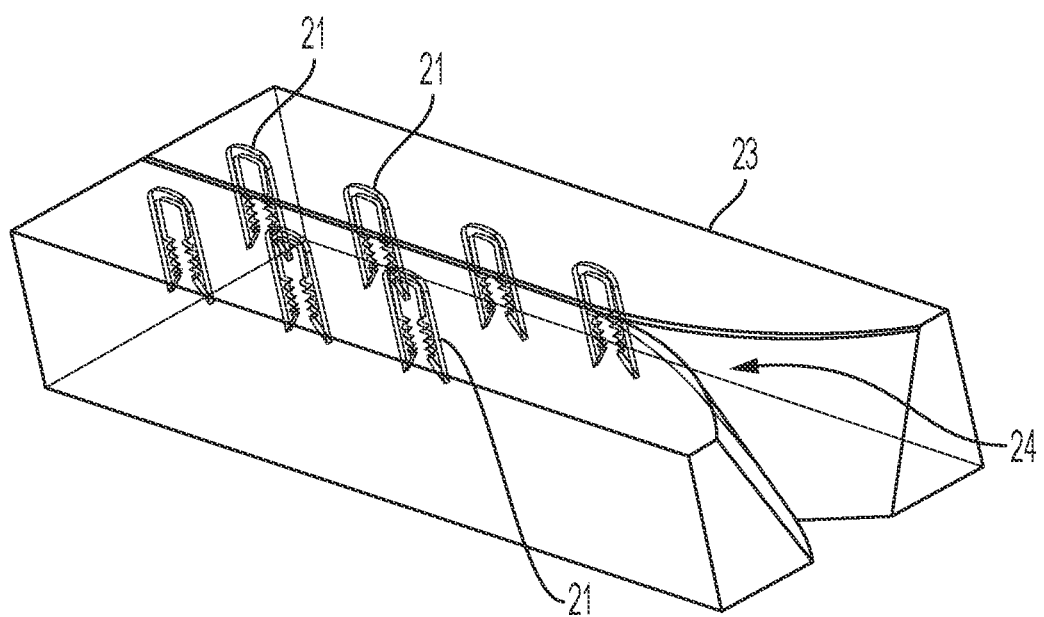
FIG. 14 shows a lateral perspective view of a schematic of an approximated tissue having staples placed therein.

FIG. 14 shows a lateral perspective view of a schematic of an approximated tissue having staples placed therein. This view provides a detailed view through a transparent schematic of approximated tissue 23 having a series of shows a series of staples 21 fixed in the tissue 23 (captured suture 22 not shown) so as to be able to close approximated tissue separation 24.

Figure 15:
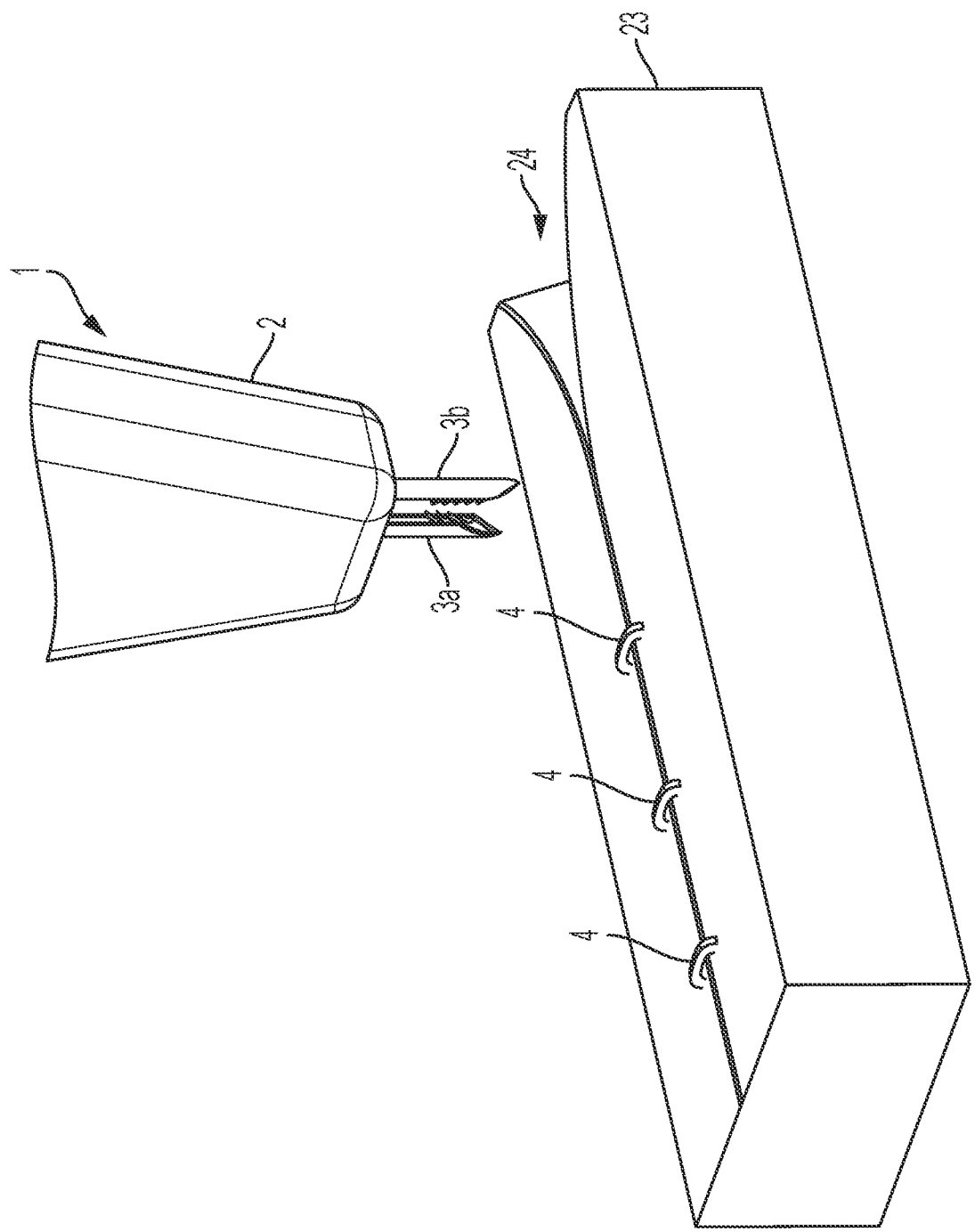
FIG. 15 shows a lateral perspective view of a flexible surgical staple and staple insertion device in accordance with one embodiment of the invention, positioned over a schematic of an approximated tissue having staples placed therein.

FIG. 15 shows a lateral perspective view of a surgical staple 21 and staple insertion device 1 in accordance with another embodiment of the invention, positioned over a schematic of an approximated tissue 23 having flexible staples, such as staple 4 placed therein. However, this Figure shows how the flexible surgical staples 4 of the present invention may be used to directly approximate and close approximated tissue separation 24. It will be appreciated that this may be done using the self-approximating, such as staples 4 or 14 delivered respectively from the straight (3a and 3b) or angled (13a and 13b) insertion needles of respective staple insertion devices 1 and 11 as described herein.

Figure 16:
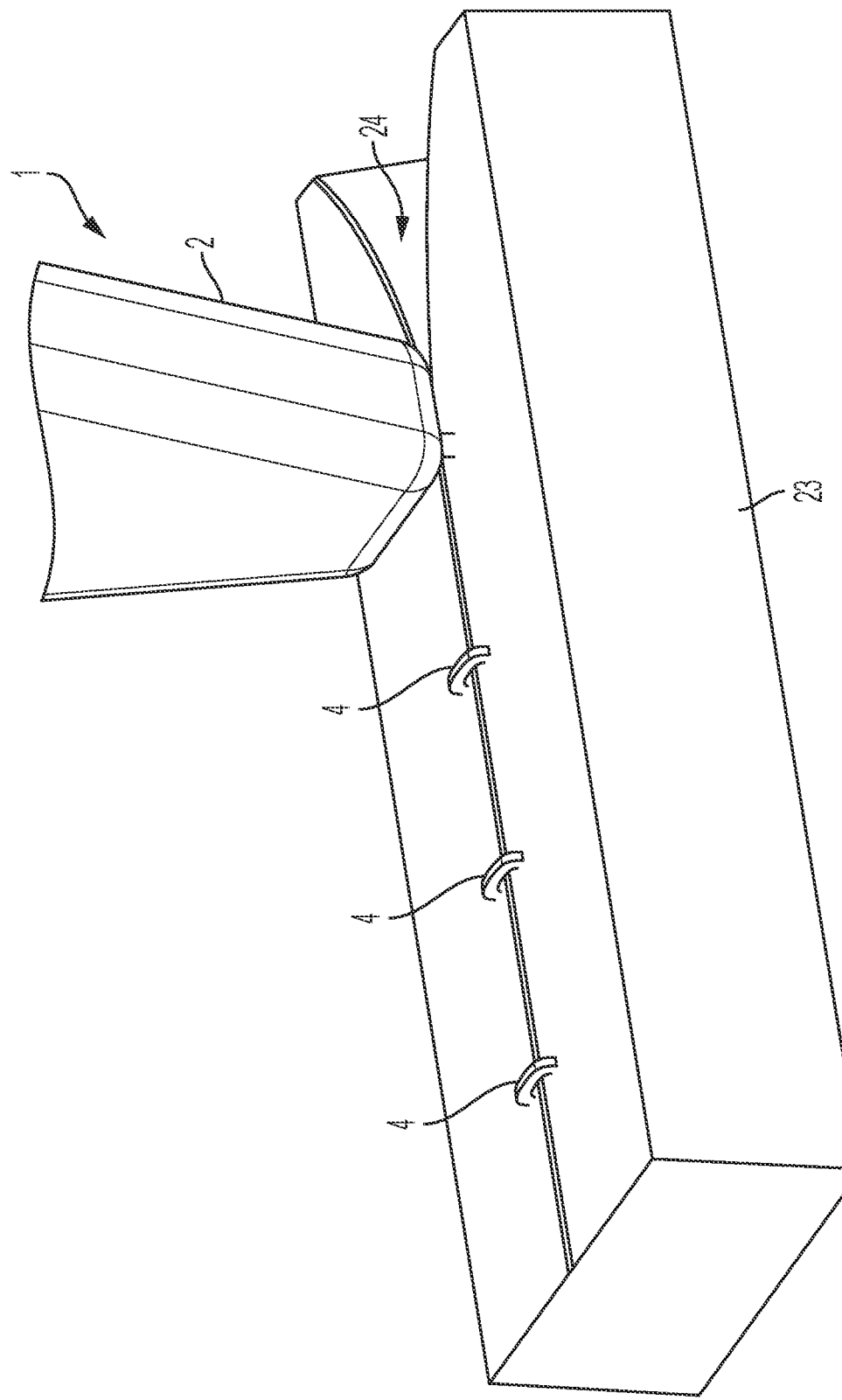
FIG. 16 shows a lateral perspective view of a flexible surgical staple and staple insertion device in accordance with one embodiment of the invention, positioned over a schematic of an approximated tissue having staples placed therein.

FIG. 16 shows a lateral perspective view of a surgical staple 21 and staple insertion device 1 in accordance with another embodiment of the invention, positioned as it inserts into a schematic of an approximated tissue 23 so as to place one of a series of flexible staples, such as staple 4, into approximated tissue 23 so as to close approximated tissue separation 24.

Figure 17:
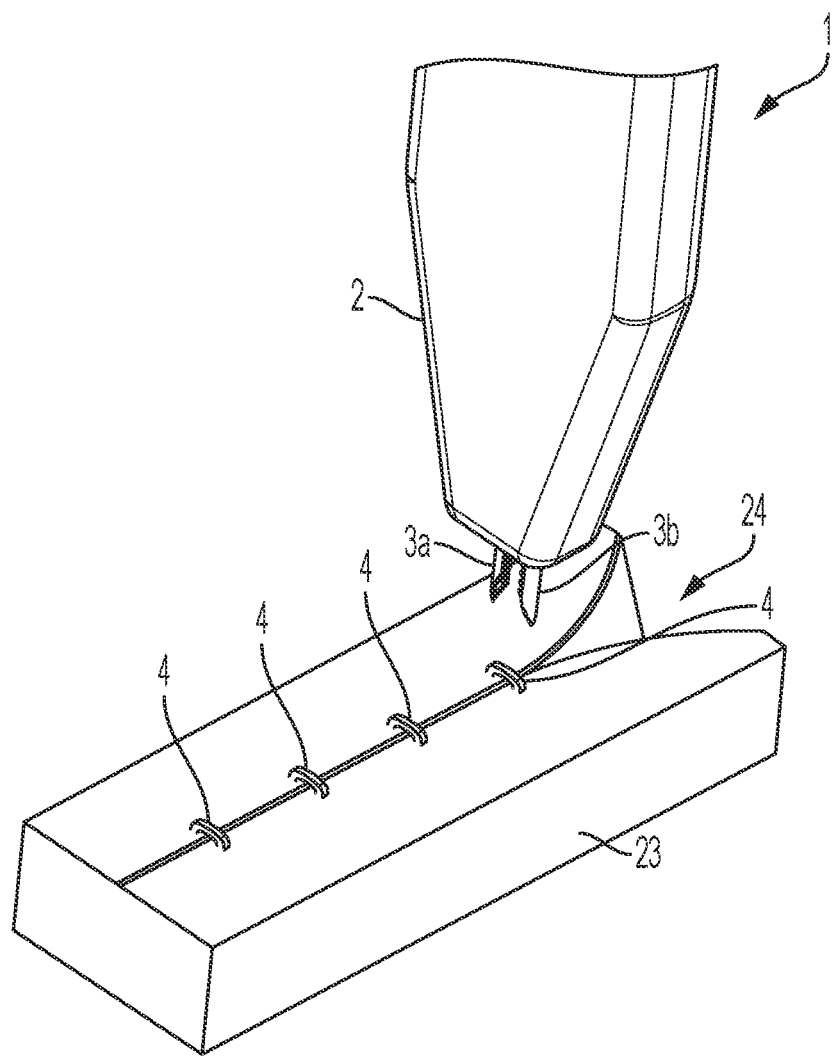
FIG. 17 shows a lateral perspective view of a flexible surgical staple and staple insertion device in accordance with one embodiment of the invention, positioned over a schematic of an approximated tissue having staples placed therein.

FIG. 17 shows a lateral perspective view of a surgical staple 21 and staple insertion device 1 in accordance with another embodiment of the invention, positioned as it is withdrawn having inserted into a schematic of an approximated tissue 23 to provide a series of flexible staples, such as staple 4 to maintain the closure of approximated tissue separation 24.

Figure 18:
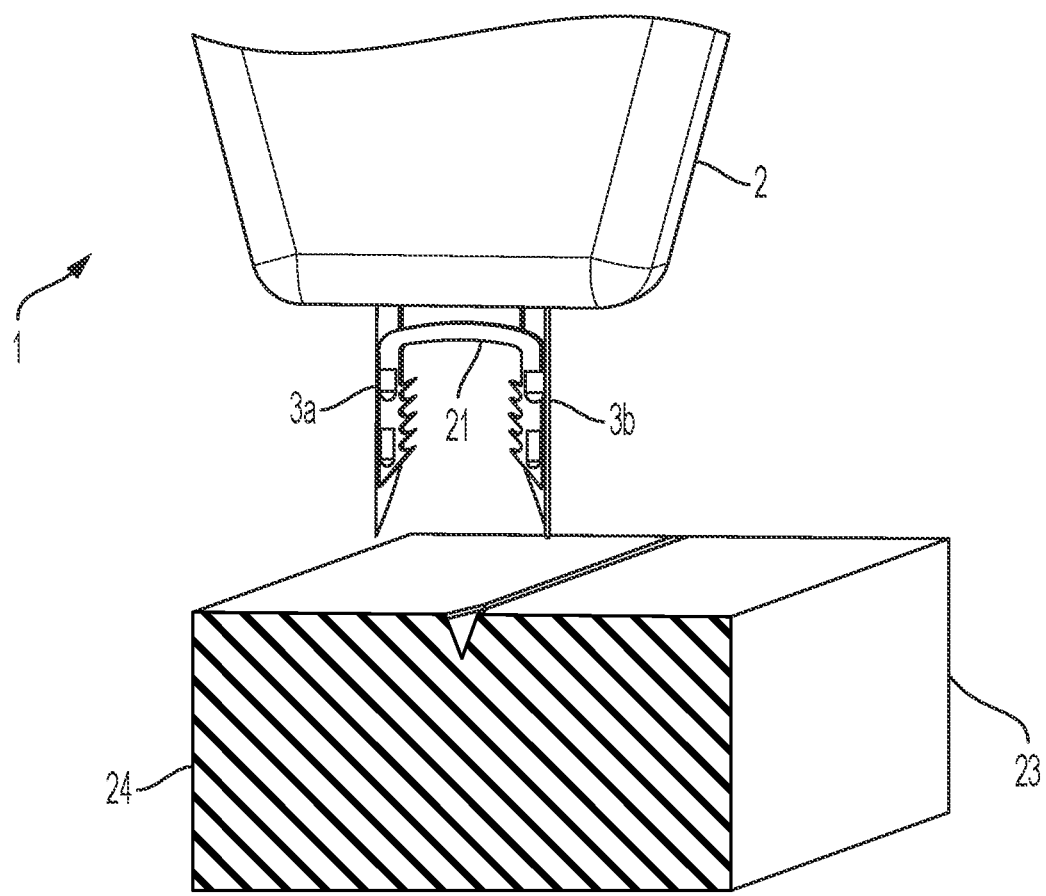
FIG. 18 shows a lateral perspective view of a flexible surgical staple and staple insertion device in accordance with one embodiment of the invention, positioned over a schematic of an approximated tissue.

FIG. 18 shows a lateral perspective view of a flexible surgical staple and staple insertion device in accordance with one embodiment of the invention, positioned over a schematic of an approximated tissue. FIG. 18 shows a lateral perspective view of a compressively flexible surgical staple (such as a compressively flexible variant of staple 21) and staple insertion device 1 in accordance with another embodiment of the invention, positioned over a schematic of an approximated tissue 23 (shown in sectioned view and showing approximated tissue separation 24). This Figure shows the approach of staple insertion device 1 to approximated tissue 23. The staple legs may also be provided with supplemental three-dimensional features, such as cylindrical section portions to permit the opposed channels (such as 3c and 3d or 13c and 13d, that may have rounded interior surfaces) to better accommodate the staple legs to better maintain them in a compressed position prior to release. Likewise, such supplemental three-dimensional features may be used in another variant of the invention wherein the flexible staple with converging staple legs is retained in a relatively tensed and expanded position (such as wherein the staple legs are held substantially parallel in accordance with the position of opposed channels (such as 3c and 3d)), and is released after insertion to return to a closed position to grip the tissue for approximation.

Figure 19:
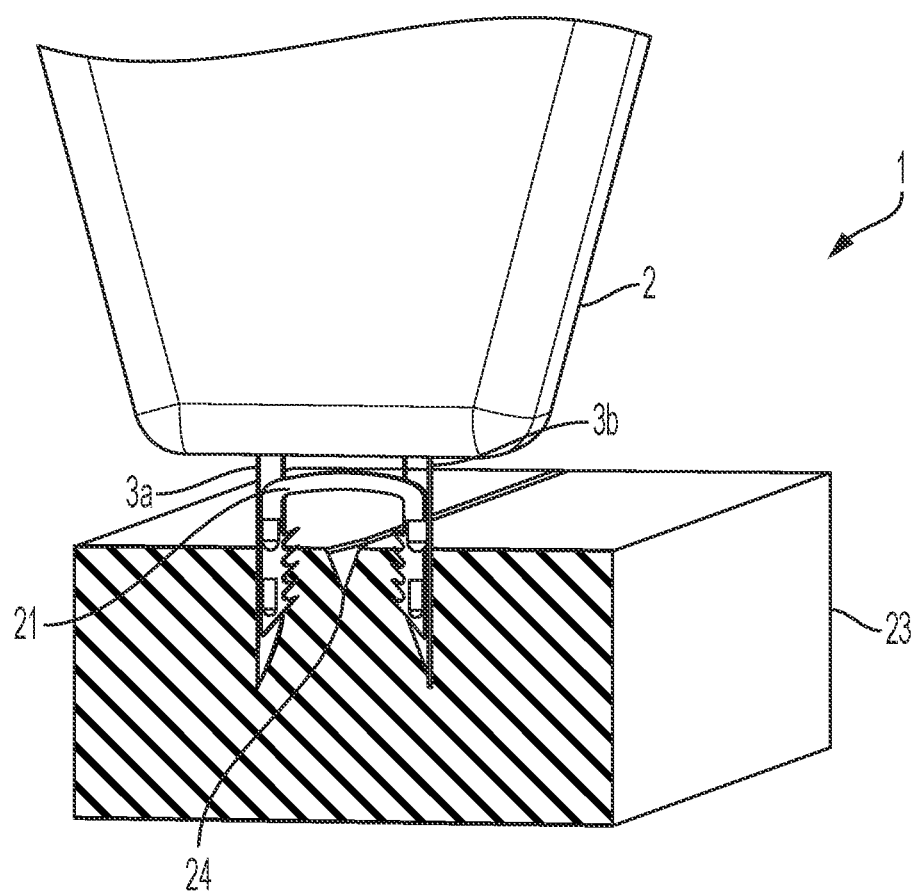
FIG. 19 shows a lateral perspective view of a flexible surgical staple and staple insertion device in accordance with one embodiment of the invention, positioned so as to insert a staple in a schematic of an approximated tissue.

FIG. 19 shows a lateral perspective view of a flexible surgical staple and staple insertion device in accordance with one embodiment of the invention as shown in FIG. 18, and wherein like numerals refer to identified features. This Figure shows staple insertion device 1 positioned upon having partially inserted a compressively flexible surgical staple (such as a compressively flexible variant of staple 21) into an approximated tissue 23 (shown in sectioned view and showing approximated tissue separation 24).

Figure 20:
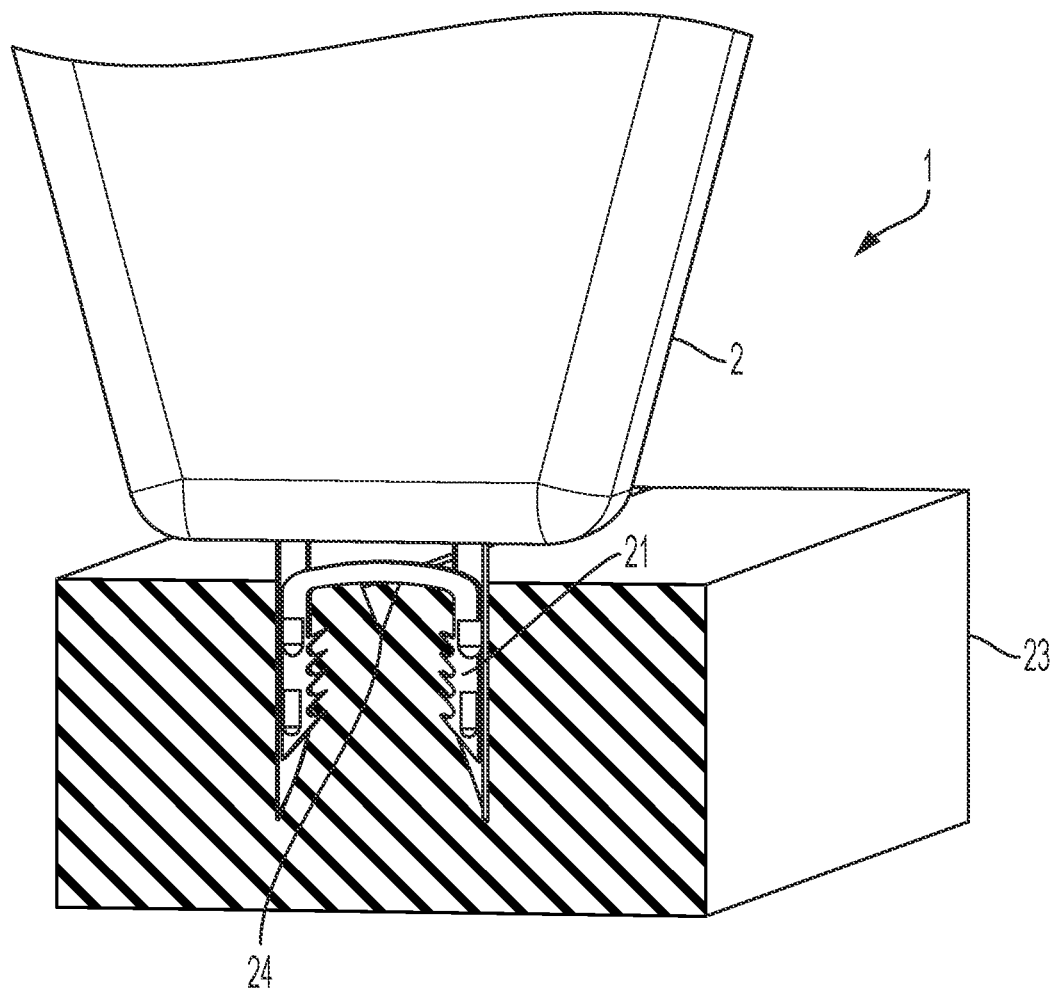
FIG. 20 shows a lateral perspective view of a flexible surgical staple and staple insertion device in accordance with one embodiment of the invention, positioned so as to insert a staple in a schematic of an approximated tissue.

FIG. 20 shows a lateral perspective view of a flexible surgical staple and staple insertion device in accordance with one embodiment of the invention as shown in FIG. 18, and wherein like numerals refer to identified features. This Figure shows staple insertion device 1 positioned upon having fully inserted a compressively flexible surgical staple (such as a compressively flexible variant of staple 21) into an approximated tissue 23 (shown in sectioned view and showing approximated tissue separation 24). This Figure shows the insertion of flexible surgical staple to close approximated tissue separation 24 in tissue 23.

Figure 21:
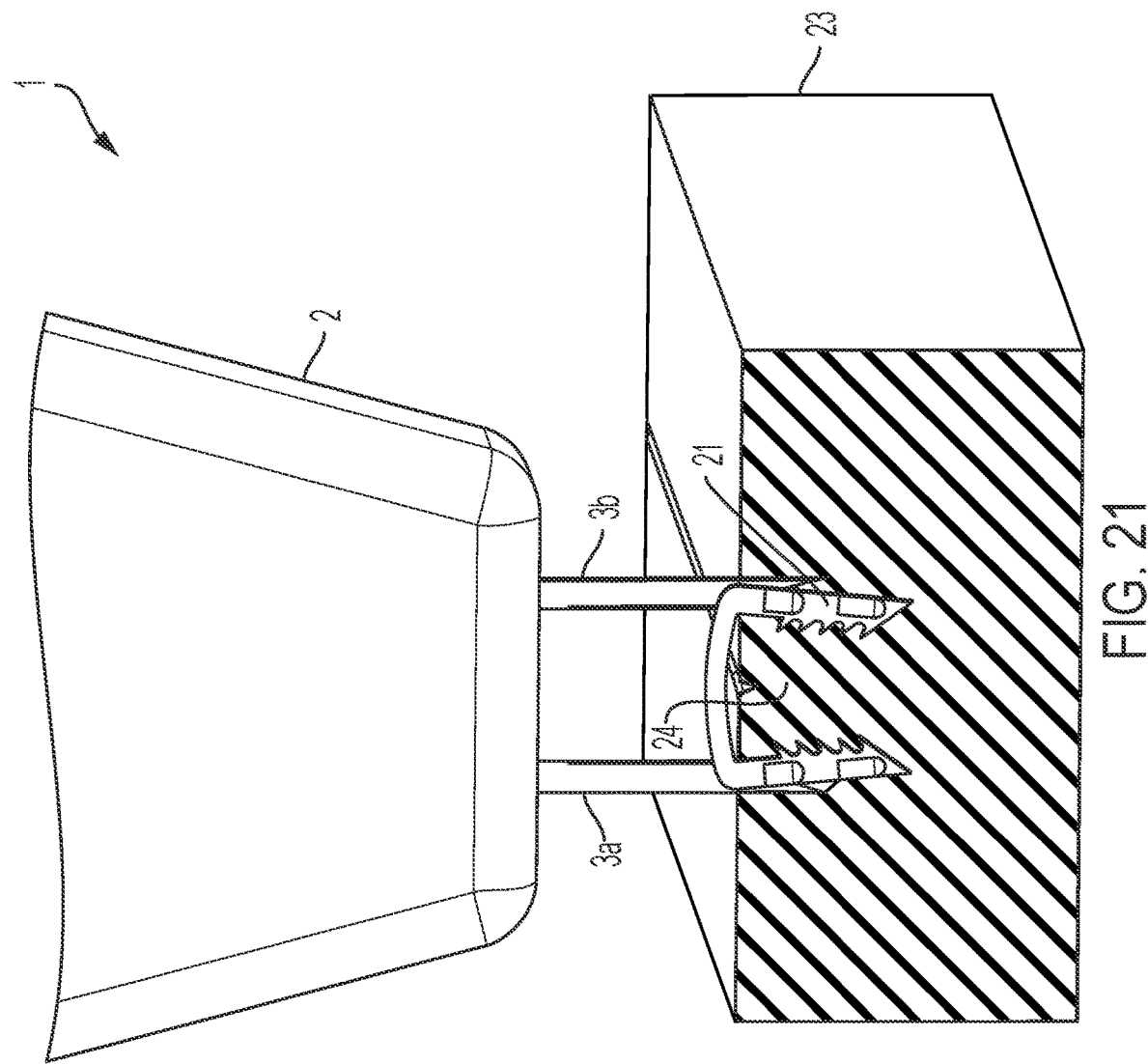
FIG. 21 shows a lateral perspective view of a flexible surgical staple and staple insertion device in accordance with one embodiment of the invention, positioned so as to insert a staple in a schematic of an approximated tissue.

FIG. 21 shows a lateral perspective view of a flexible surgical staple and staple insertion device in accordance with one embodiment of the invention as shown in FIG. 18, and wherein like numerals refer to identified features. This Figure shows staple insertion device 1 positioned as it withdraws having inserted a compressively flexible surgical staple (such as a compressively flexible variant of staple 21) into an approximated tissue 23 (shown in sectioned view and showing approximated tissue separation 24). This Figure shows the partial release of flexible surgical staple to close approximated tissue separation 24 in tissue 23.

Figure 22:
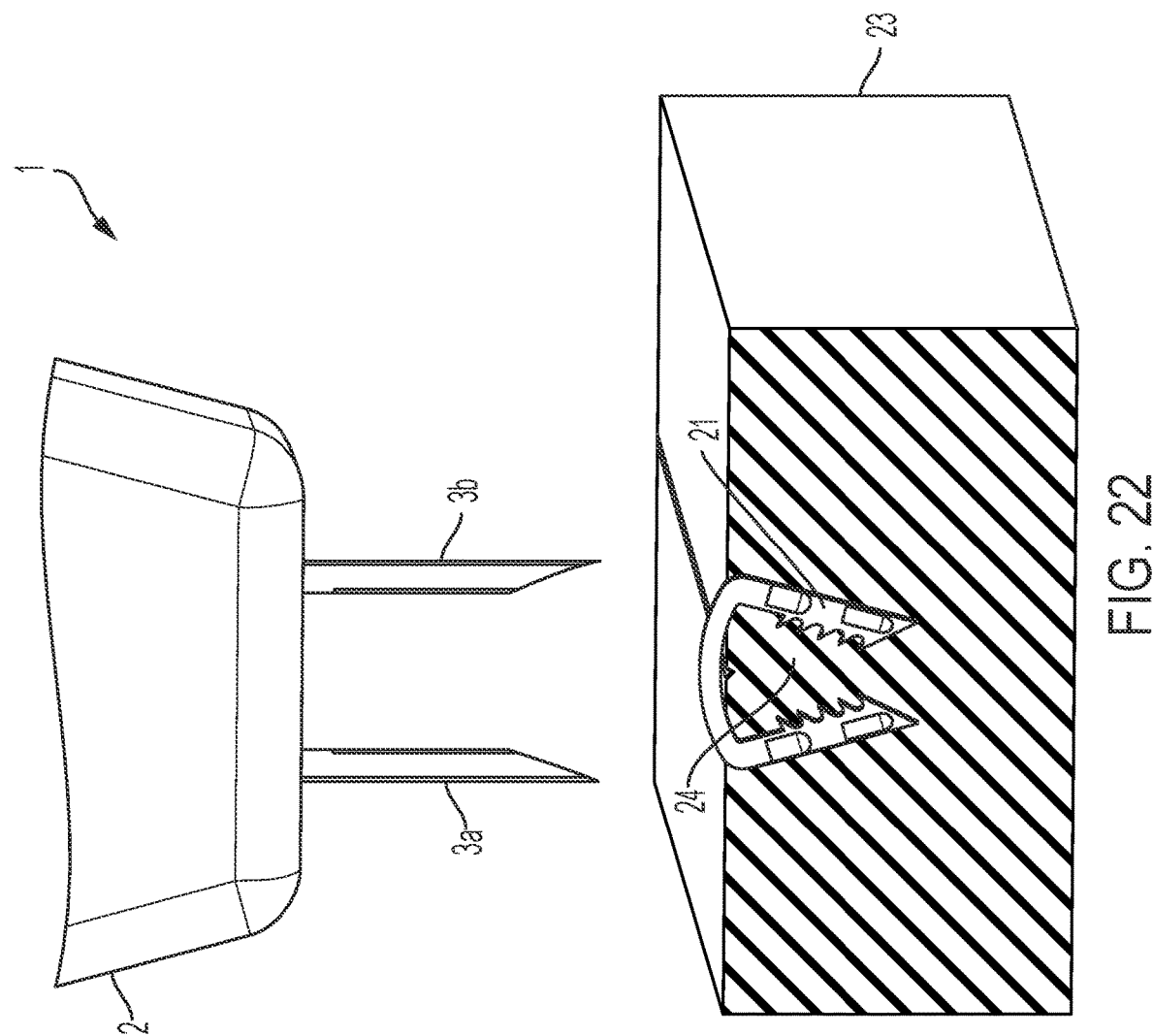
FIG. 22 shows a lateral perspective view of a flexible surgical staple and staple insertion device in accordance with one embodiment of the invention, positioned so as to insert a staple in a schematic of an approximated tissue.

FIG. 22 shows a lateral perspective view of a flexible surgical staple and staple insertion device in accordance with one embodiment of the invention as shown in FIG. 18, and wherein like numerals refer to identified features. This Figure shows staple insertion device 1 positioned after it has been fully withdrawn leaving compressively flexible surgical staple (such as a compressively flexible variant of staple 21) in the approximated tissue 23 (shown in sectioned view and showing approximated tissue separation 24). This Figure shows the complete release and compression of flexible surgical staple to close approximated tissue separation 24 in tissue 23.

Figure 23:
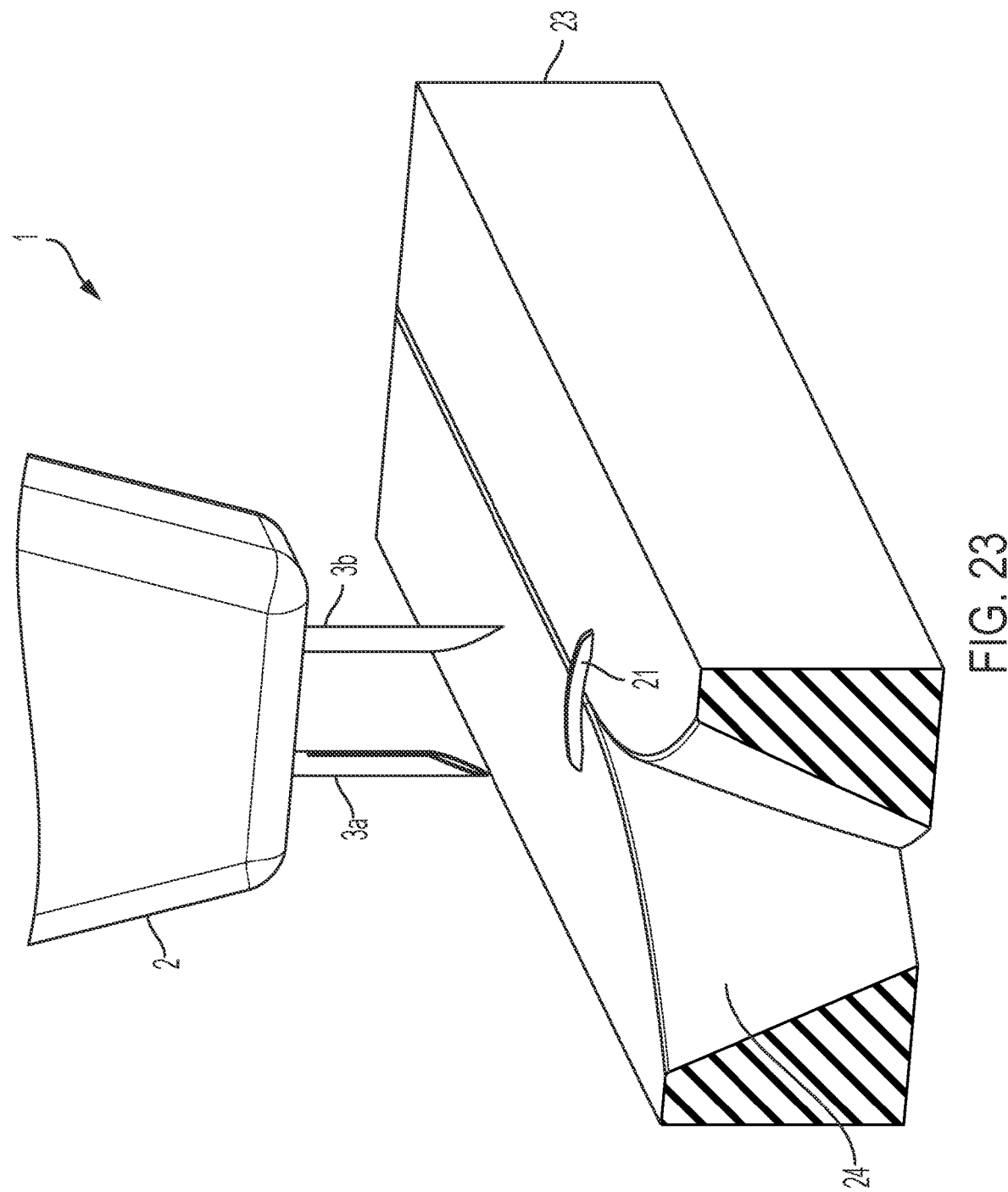
FIG. 23 shows a lateral perspective view of a flexible surgical staple and staple insertion device in accordance with one embodiment of the invention, positioned so as to insert a staple in a schematic of an approximated tissue.

FIG. 23 shows a lateral perspective view of a flexible surgical staple and staple insertion device in accordance with one embodiment of the invention as shown in FIG. 18, and wherein like numerals refer to identified features. This Figure shows the completed closure of approximated tissue separation 24 in tissue 23 by staples, such as staple 21.

Figure 24:
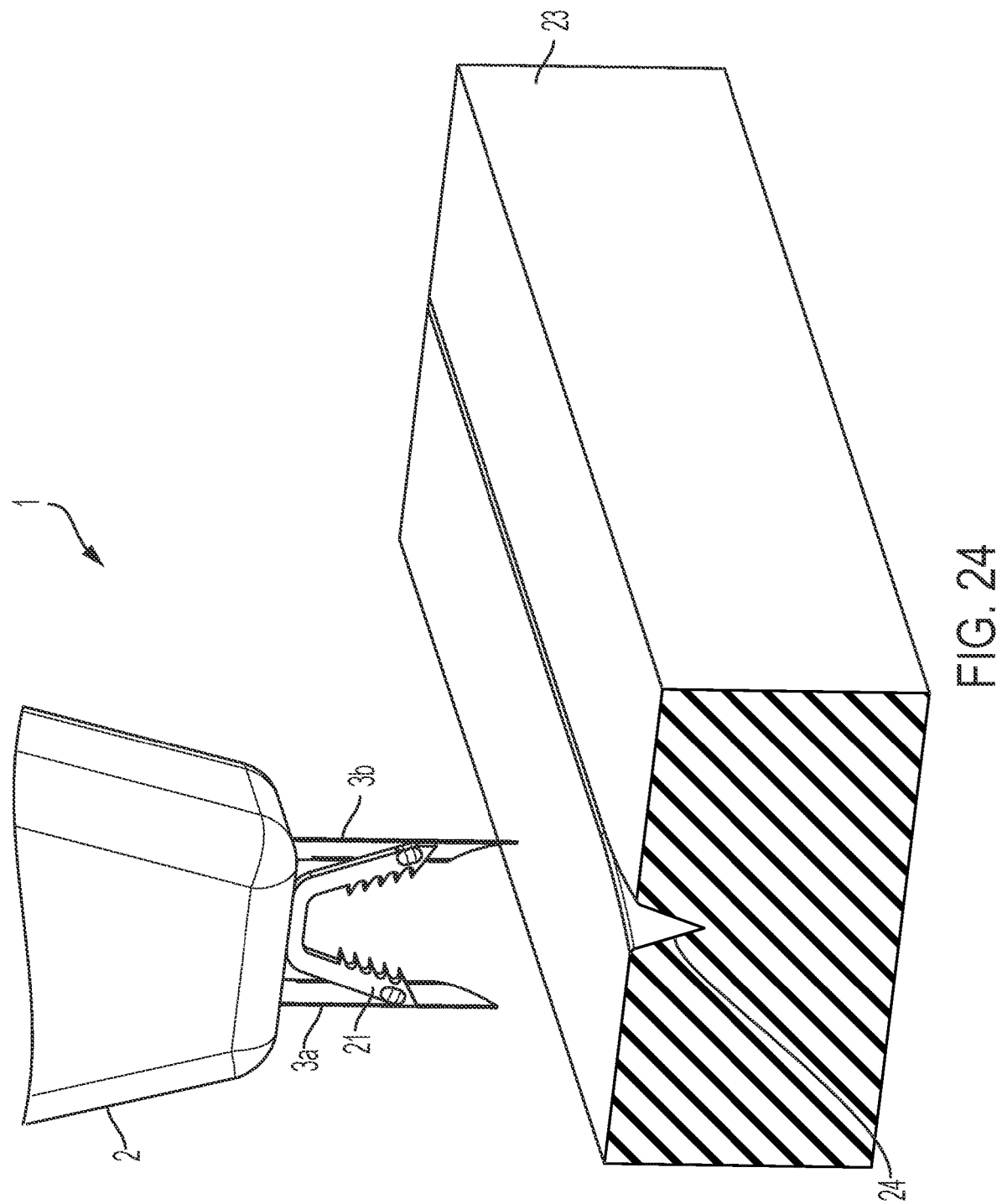
FIG. 24 shows a lateral perspective view of a flexible surgical staple and staple insertion device in accordance with one embodiment of the invention, positioned so as to insert a staple in a schematic of an approximated tissue.

FIG. 24 shows a lateral perspective view of a flexible surgical staple and staple insertion device in accordance with one embodiment of the invention as shown in FIG. 18, and wherein like numerals refer to identified features. This Figure shows the approach of staple insertion device 1 to approximated tissue 23. This Figure also shows how the staple legs may be provided with supplemental three-dimensional features, such as cylindrical section portions to permit the opposed channels (such as parallel 3c and 3d or angled 13c and 13d, that may have rounded interior surfaces) to better accommodate the staple legs to better maintain them in an open relatively tensed and expanded position (such as wherein the staple legs are held substantially parallel in accordance with the position of opposed channels (such as 3c and 3d)), and is released after insertion to return to a closed position to grip the tissue for approximation.

Figure 25:
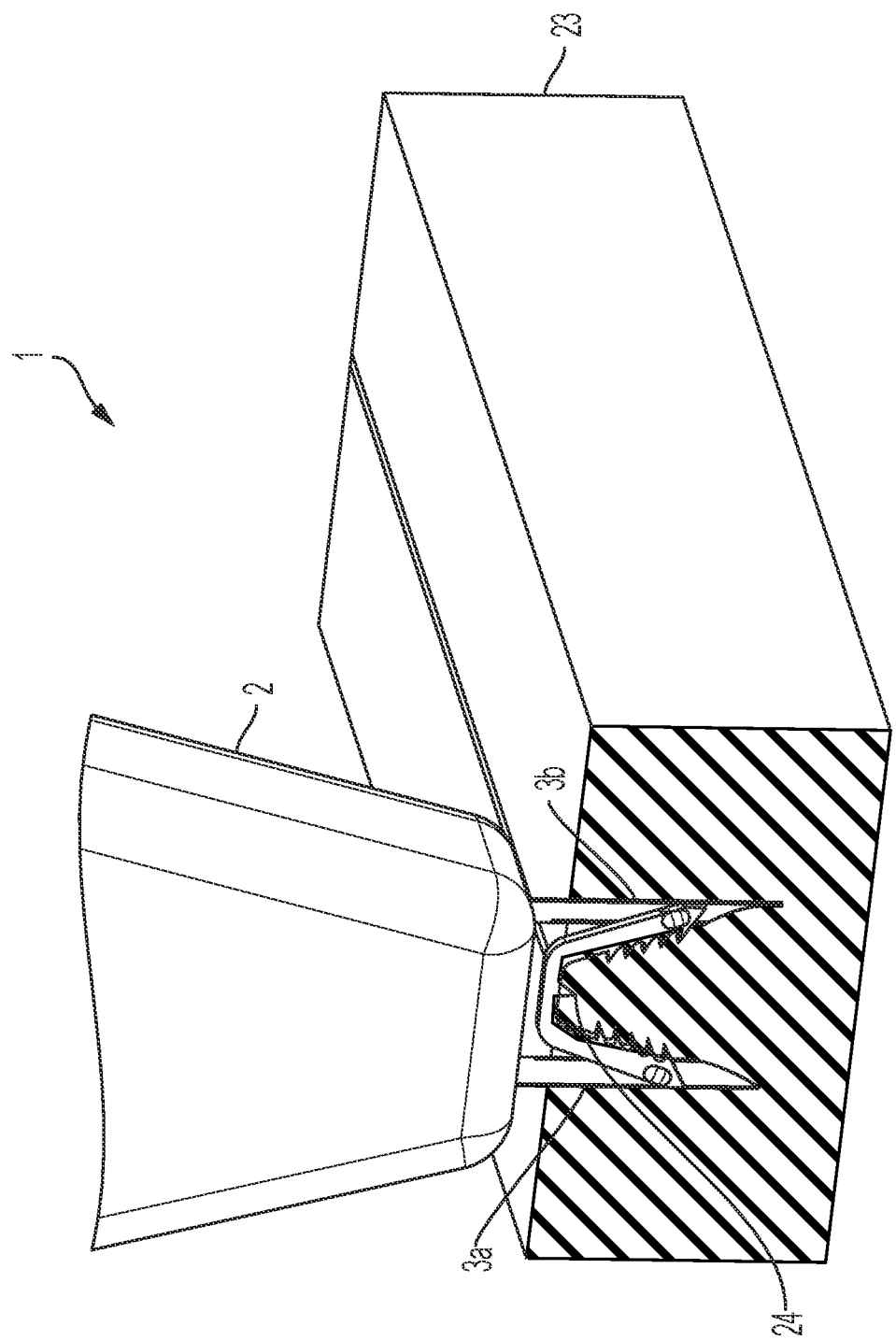
FIG. 25 shows a lateral perspective view of a flexible surgical staple and staple insertion device in accordance with one embodiment of the invention, inserting a staple into a schematic of an approximated tissue.

FIG. 25 shows a lateral perspective view of a flexible surgical staple and staple insertion device in accordance with one embodiment of the invention as shown in FIG. 18, and wherein like numerals refer to identified features. This Figure shows the approach of staple insertion device 1 to approximated tissue 23. This Figure also shows how the staple legs may be provided with supplemental three-dimensional features, such as cylindrical section portions to permit the opposed channels (such as parallel 3c and 3d or angled 13c and 13d, that may have rounded interior surfaces) to better accommodate the staple legs to better maintain them in an open relatively tensed and expanded position (such as wherein the staple legs are held substantially parallel in accordance with the position of opposed channels (such as 3c and 3d)), and is released after insertion to return to a closed position to grip the tissue for approximation.

Figure 26:
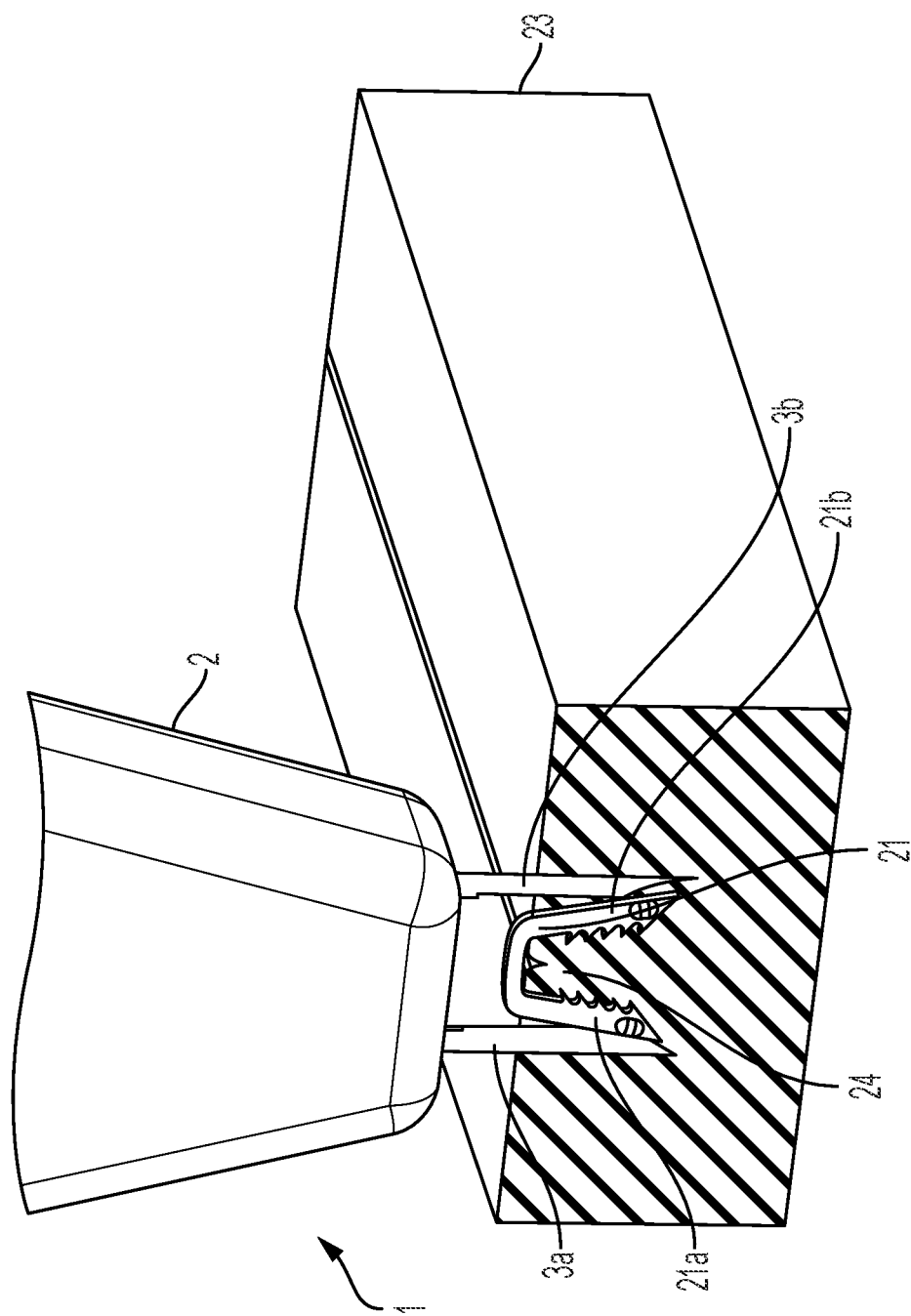
FIG. 26 shows a lateral perspective view of a flexible surgical staple and staple insertion device in accordance with one embodiment of the invention, inserting a staple into a schematic of an approximated tissue.

FIG. 26 shows a lateral perspective view of a flexible surgical staple and staple insertion device in accordance with one embodiment of the invention as shown in FIG. 18, and wherein like numerals refer to identified features. This Figure shows the release of a staple 21 from staple insertion device 1 to remain in approximated tissue 23. This Figure also shows how the supplemental three-dimensional features on staple legs 21a and 21b release from the parallel opposed channels 3c and 3d after insertion to return to the staple a closed position to grip the tissue for approximation.

Figure 27:
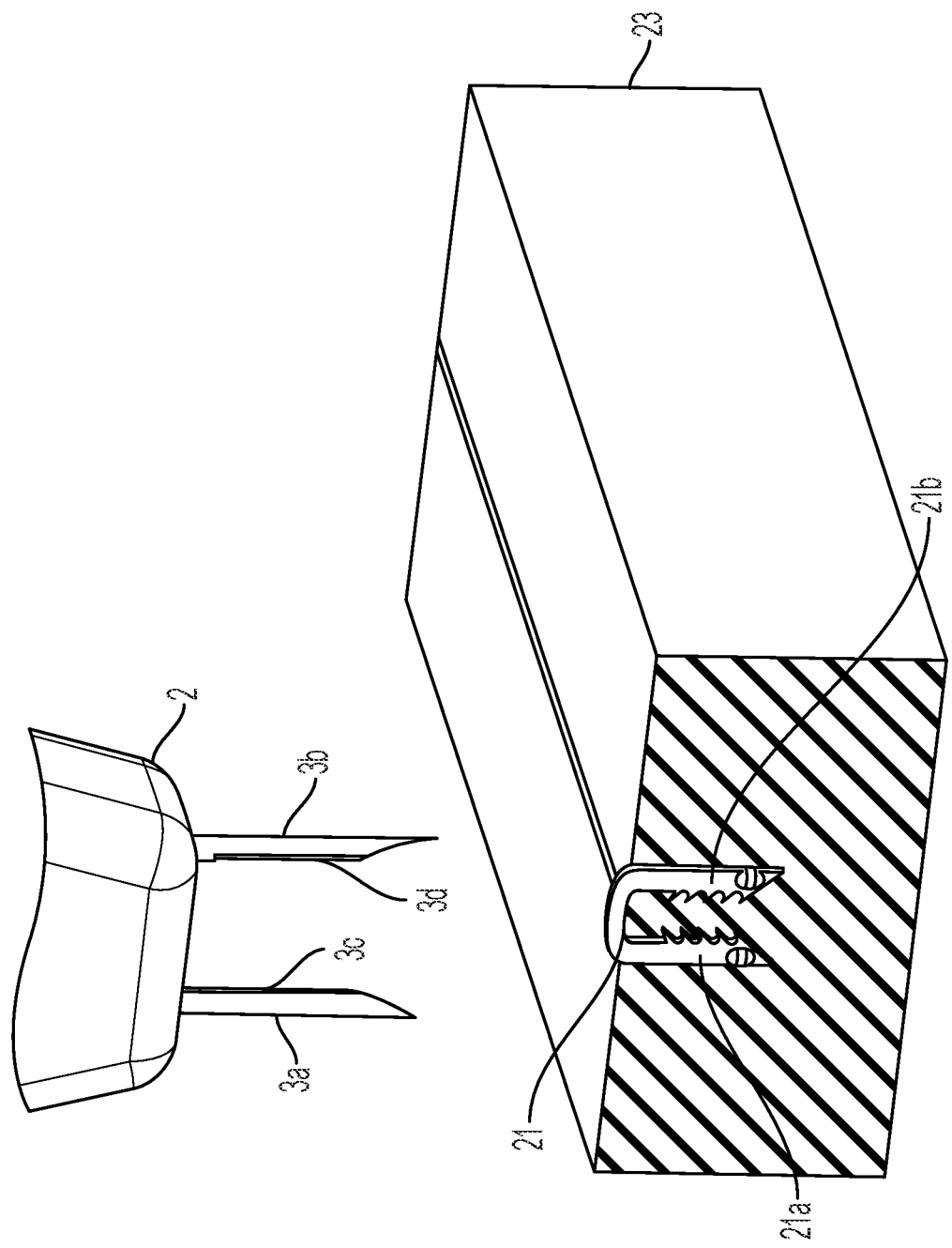
FIG. 27 shows a lateral perspective view of a flexible surgical staple and staple insertion device in accordance with one embodiment of the invention, withdrawing from a schematic of an approximated tissue.

FIG. 27 shows a lateral perspective view of a flexible surgical staple and staple insertion device in accordance with one embodiment of the invention as shown in FIG. 18, and wherein like numerals refer to identified features. This Figure shows the completed closure of approximated tissue separation 24 in tissue 23 by staples, such as staple 21.

Figure 28:
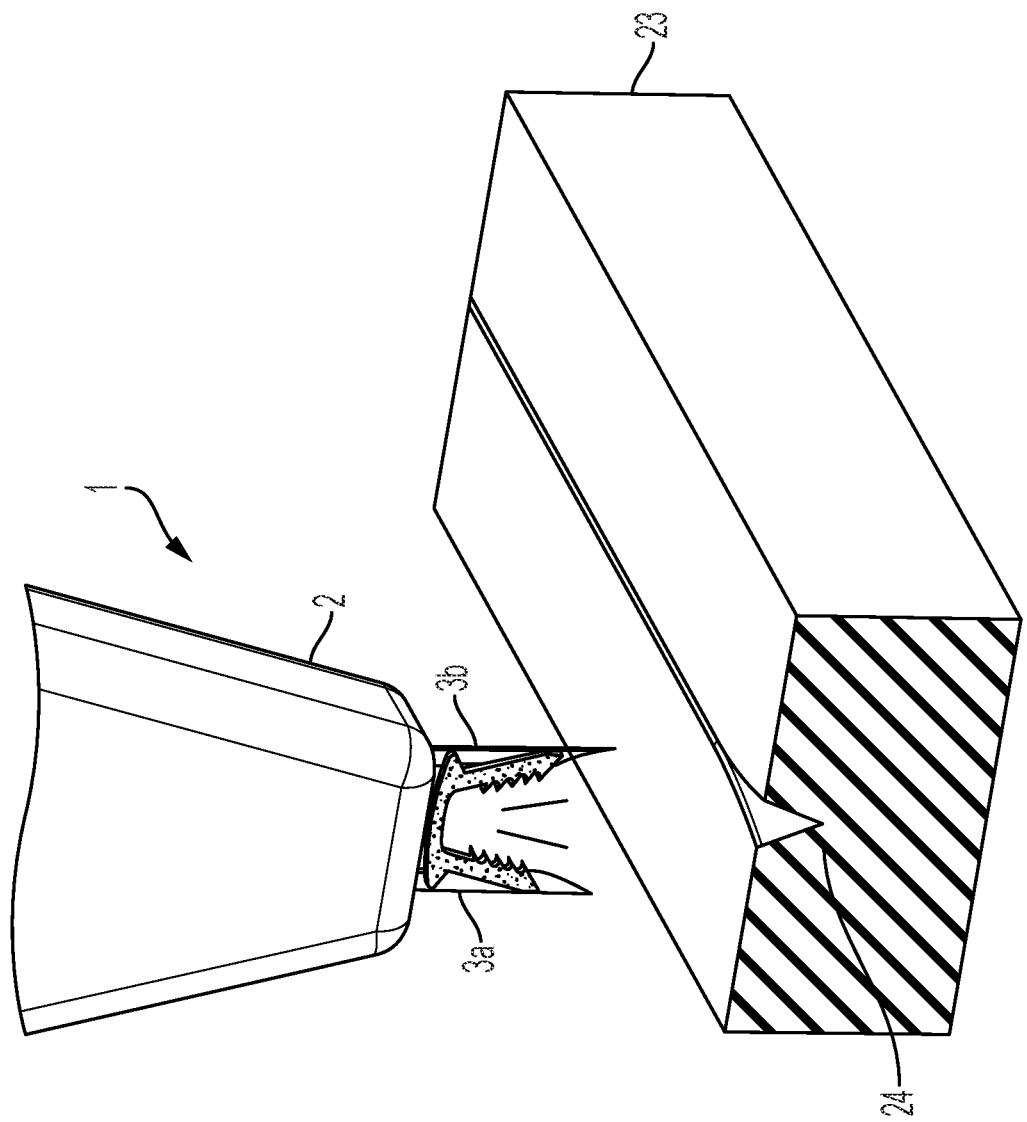
FIG. 28 shows a lateral perspective view of a flexible surgical staple and staple insertion device in accordance with one embodiment of the invention, positioned so as to insert a staple in a schematic of an approximated tissue.

FIG. 28 shows a lateral perspective view of a flexible surgical staple 25 and staple insertion device 1 in accordance with one embodiment of the invention, otherwise similar to that shown in FIG. 18, with the staple insertion device 1 positioned over a schematic of an approximated tissue 23. FIG. 28 shows a lateral perspective view of a staple insertion device 1 holding a slightly different compressively flexible surgical staple 25 that features a tapered geometry that permits the staple to be more securely held in the opposed channels (such as 3c and 3d) of insertions needles 3a and 3b to better accommodate the staple legs to better maintain them in a compressed position prior to release, and facilitate their release from the insertion needle similar to that shown in FIGS. 18-27. Another feature of flexible surgical staple 25 is the inclusion of lateral extensions of the staple at or near the staple bridge and staple legs, that may be applied to provide additional dimensional stability and strength to the flexible surgical staple as well as to provide additional surface to which may be applied an urging force from the staple insertion device 1 (including those comprising a sliding driver) to better facilitate insertion.

Figure 29:
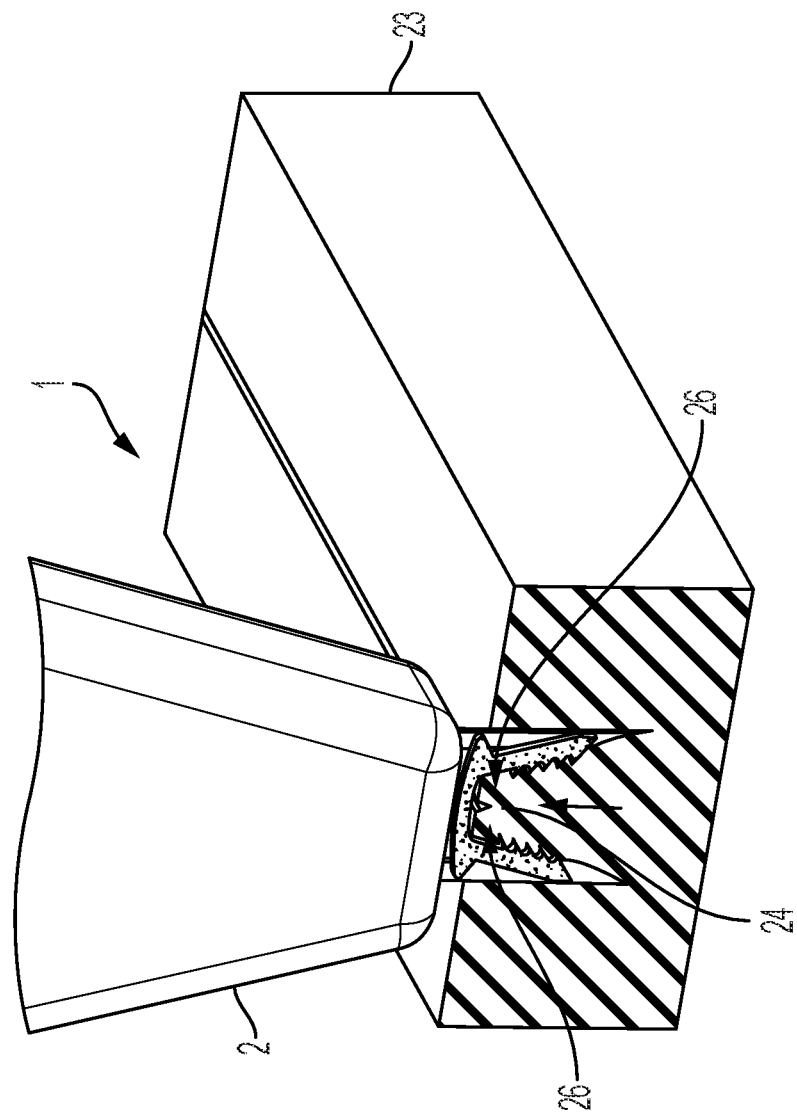
FIG. 29 shows a lateral perspective view of a flexible surgical staple and staple insertion device in accordance with one embodiment of the invention, inserting a staple into a schematic of an approximated tissue.

FIG. 29 shows a lateral perspective view of a flexible surgical staple 25 and staple insertion device 1 in accordance with one embodiment of the invention as shown in FIG. 28, and wherein like numerals refer to identified features. This Figure shows staple insertion device 1 positioned upon having fully inserted a compressively flexible surgical staple 25 into an approximated tissue 23 (shown in sectioned view and showing approximated tissue separation 24). This Figure shows how the tapered geometry of the flexible surgical staple 25 aids in the physical approximation of the opposed tissue portion during the insertion of flexible surgical staple to close approximated tissue separation 24 in tissue 23, as indicated by the directional arrows 26.

Figure 30:
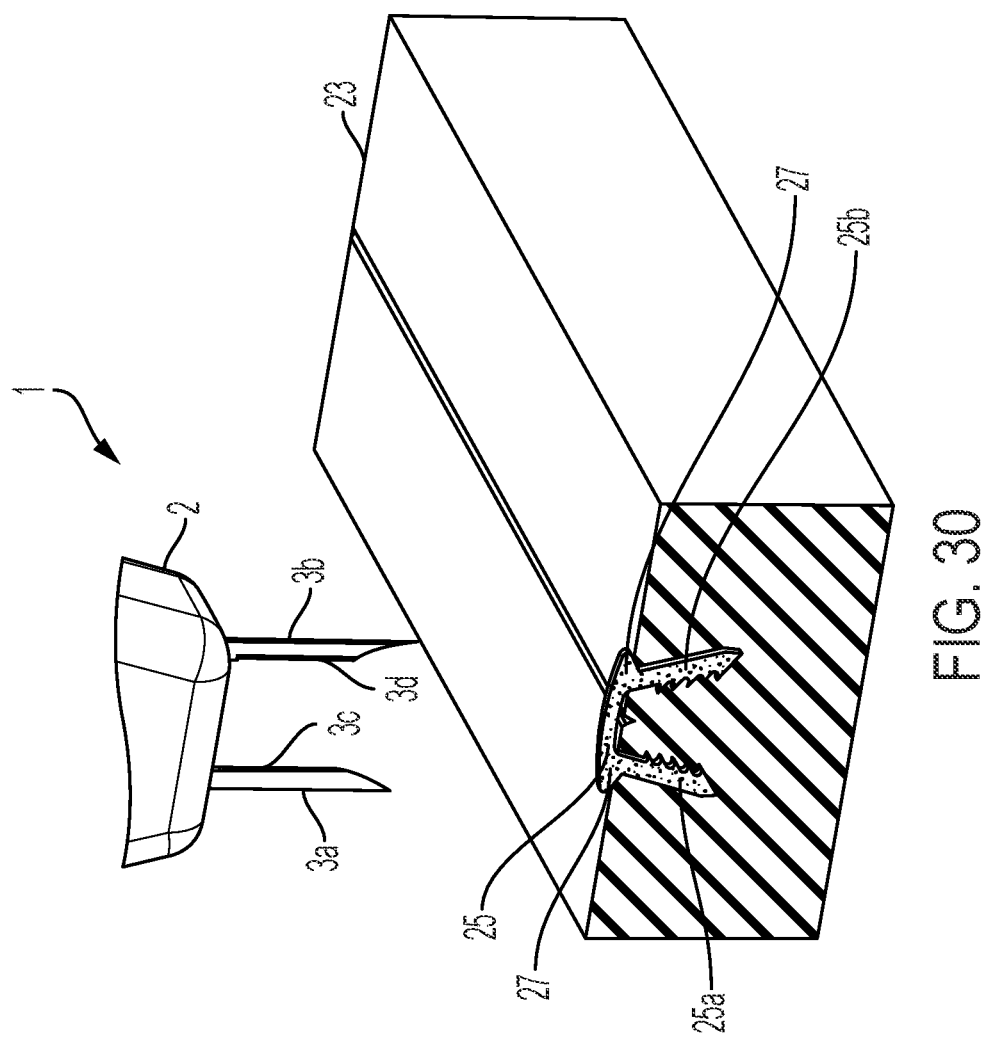
FIG. 30 shows a lateral perspective view of a flexible surgical staple and staple insertion device in accordance with one embodiment of the invention, withdrawing from a schematic of an approximated tissue.

FIG. 30 shows a lateral perspective view of a flexible surgical staple 25 and staple insertion device 1 in accordance with one embodiment of the invention as shown in FIG. 28, and wherein like numerals refer to identified features. This Figure shows the completed closure of approximated tissue separation 24 in tissue 23 by staples, such as staple 25. This Figure also shows the above-described internally tapered geometry of staple legs 25a and 25b, and the above-described lateral extensions 27 of the staple at or near the staple bridge and staple legs, that may be applied to provide additional dimensional stability and strength to the flexible surgical staple as well as to provide additional surface to which may be applied an urging force from the staple insertion device 1 (including those comprising a sliding driver) to better facilitate insertion.

It will be appreciated that this same method may be used to insert flexible surgical staples designed and formed to be expansively flexible (such as staples 4 or 14).

Figure 31:
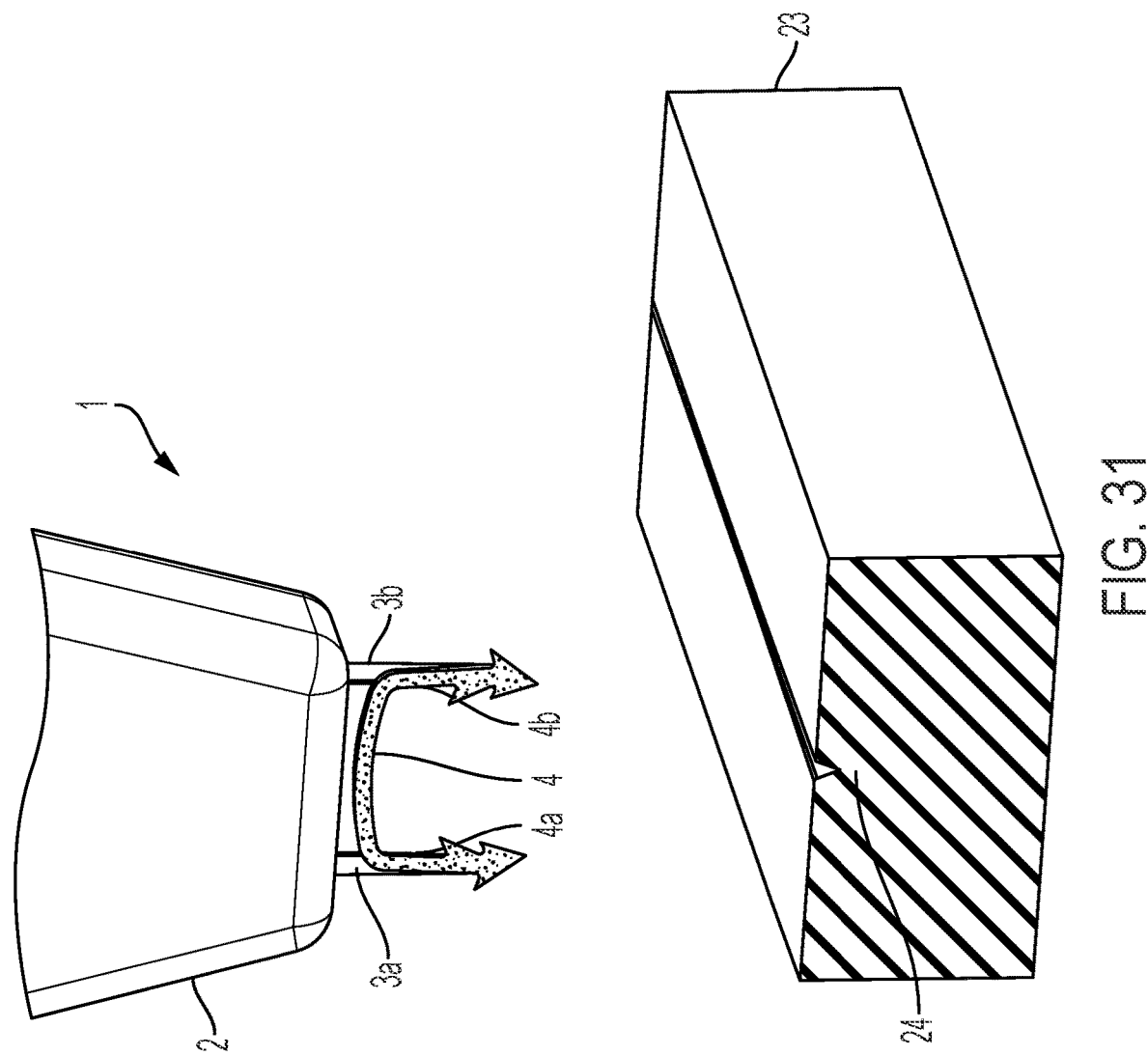
FIG. 31 shows a lateral perspective view of a flexible surgical staple and staple insertion device in accordance with one embodiment of the invention, positioned so as to insert a staple in a schematic of an approximated tissue.

FIG. 31 shows a lateral perspective view of a flexible surgical staple 4 and staple insertion device 1 in accordance with one embodiment of the invention, positioned over a schematic of an approximated tissue. FIG. 31 shows a lateral perspective view of an expansively flexible surgical staple (such as an expansively flexible variant of staple 4) and staple insertion device 1 positioned over a schematic of an approximated tissue 23 (shown in sectioned view and showing approximated tissue separation 24). This Figure shows the approach of staple insertion device 1 to approximated tissue 23. The staple legs may also be provided with supplemental three-dimensional features, such as cylindrical section portions to permit the opposed channels (such as 3c and 3d that may have rounded interior surfaces) to better accommodate the staple legs to better maintain them in a compressed position prior to release. Likewise, such supplemental three-dimensional features may be used in another variant of the invention wherein the flexible staple with converging staple legs is retained in a relatively compressed position (such as wherein the staple legs are held substantially parallel in accordance with the position of opposed channels (such as 3c and 3d)), and is released after insertion to return to a relatively opened position to grip the tissue 23 for approximation.

Figure 32:
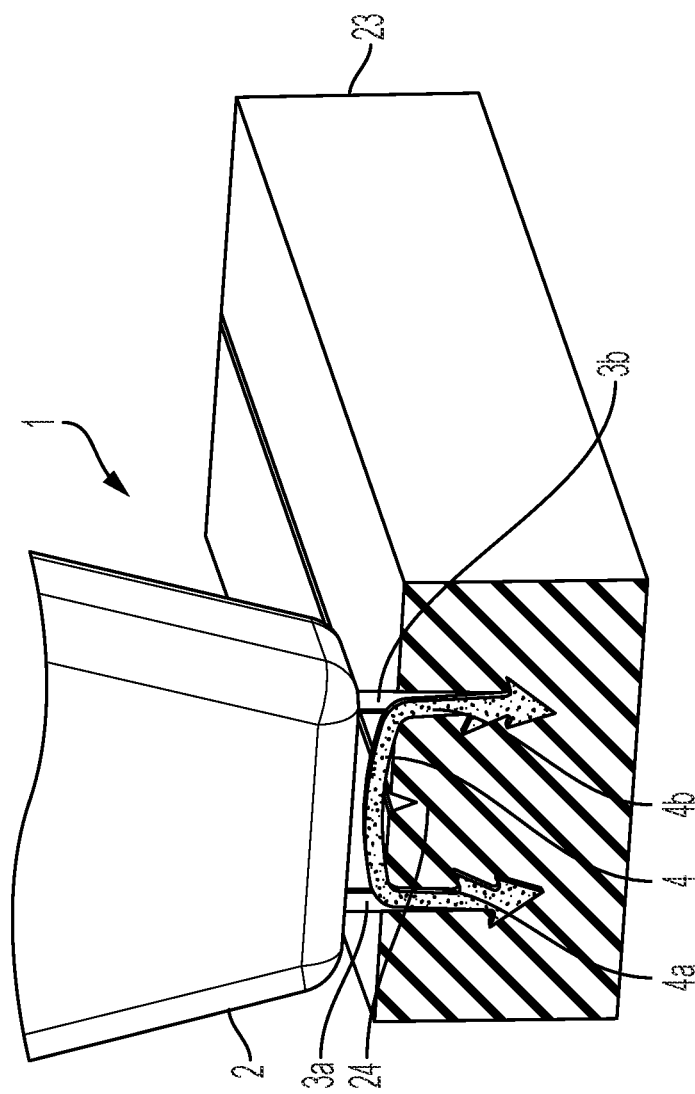
FIG. 32 shows a lateral perspective view of a flexible surgical staple and staple insertion device in accordance with one embodiment of the invention, inserting a staple into a schematic of an approximated tissue.

FIG. 32 shows a lateral perspective view of a flexible surgical staple and staple insertion device in accordance with one embodiment of the invention as shown in FIG. 31, and wherein like numerals refer to identified features. This Figure shows staple insertion device 1 positioned upon having fully inserted an expansively flexible surgical staple 4 into an approximated tissue 23 (shown in sectioned view and showing approximated tissue separation 24). This Figure shows the insertion of flexible surgical staple to close approximated tissue separation 24 in tissue 23.

Figure 33:
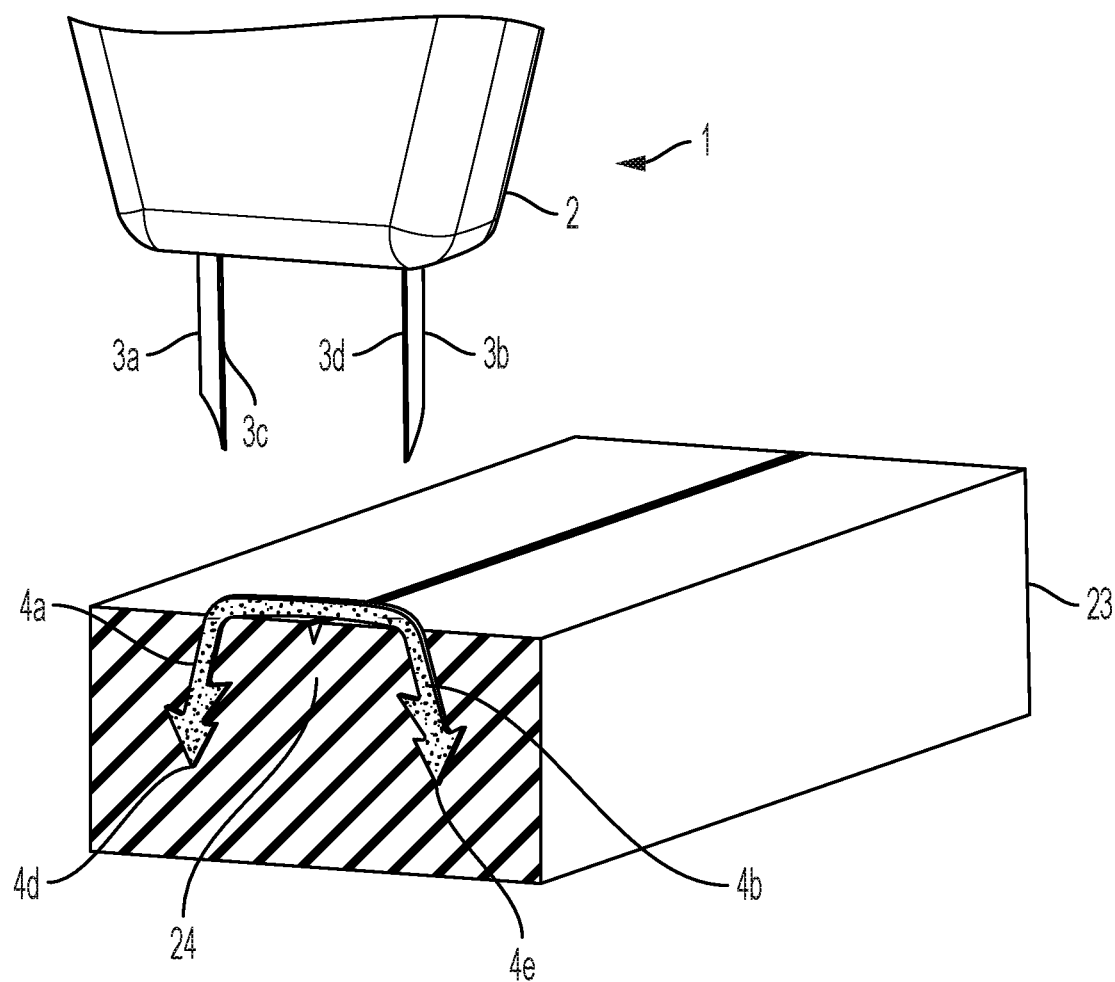
FIG. 33 shows a lateral perspective view of a flexible surgical staple and staple insertion device in accordance with one embodiment of the invention, withdrawing from a schematic of an approximated tissue.

FIG. 33 shows a lateral perspective view of a flexible surgical staple and staple insertion device in accordance with one embodiment of the invention as shown in FIG. 31, and wherein like numerals refer to identified features. This Figure shows staple insertion device 1 positioned after it has been fully withdrawn leaving expansively flexible surgical staple 4 in the approximated tissue 23 (shown in sectioned view and showing approximated tissue separation 24). This Figure shows the complete release and compression of flexible surgical staple to close approximated tissue separation 24 in tissue 23, as expansively flexible surgical staple 4 expand after disengagement from opposed channels 3c and 3d of respective insertion needles 3a and 3b. Staple barbs 4d and 4e are thereby urged into the neighboring tissue to urge it toward approximation, as indicated by the directional arrows.

Figure 34:
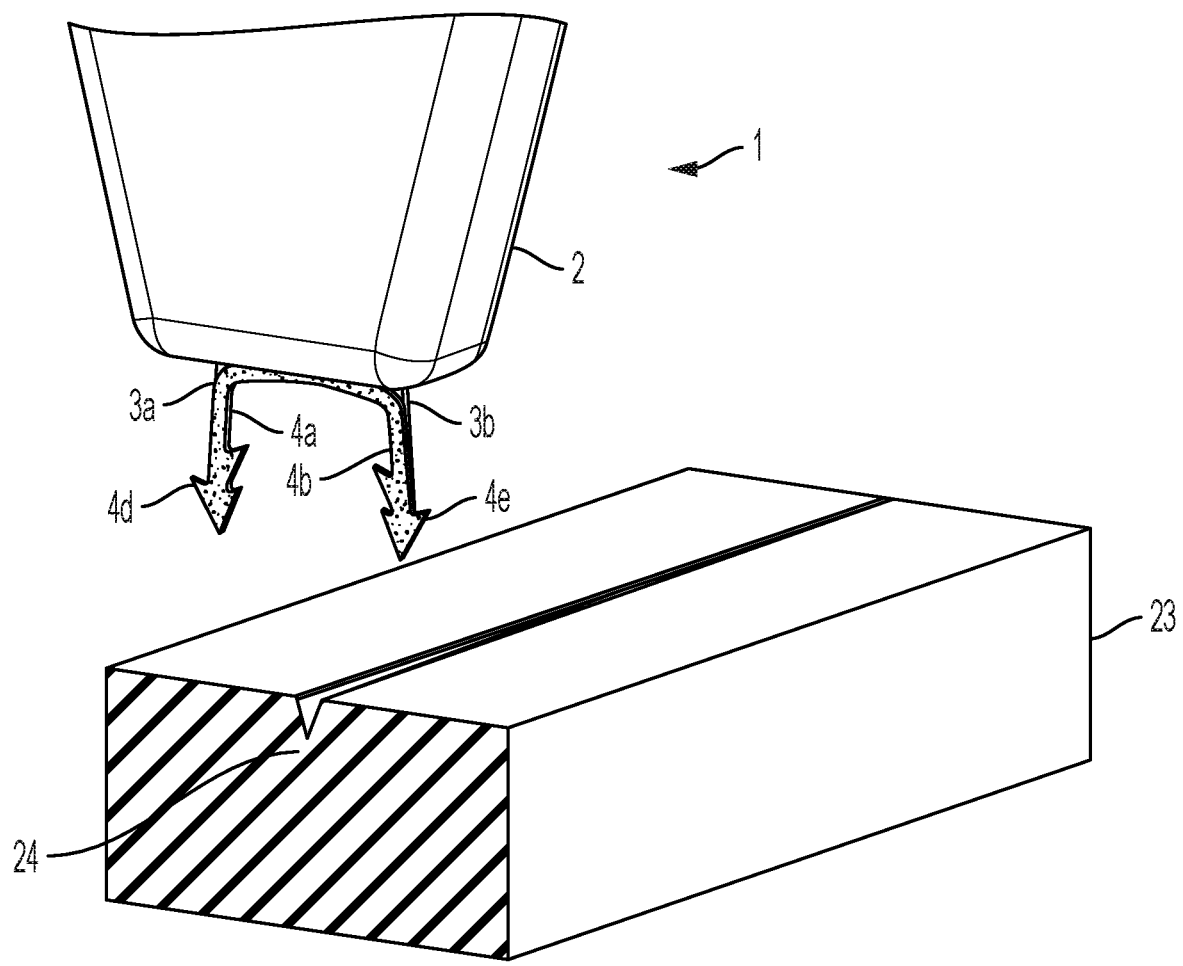
FIG. 34 shows a lateral perspective view of a flexible surgical staple and staple insertion device in accordance with one embodiment of the invention, positioned so as to insert a staple in a schematic of an approximated tissue.

FIG. 34 shows a lateral perspective view of a flexible surgical staple 4 and staple insertion device 1 in accordance with one embodiment of the invention, positioned over a schematic of an approximated tissue. FIG. 34 shows a lateral perspective view of an expansively flexible surgical staple (such as an expansively flexible variant of staple 4) and staple insertion device 1 positioned over a schematic of an approximated tissue 23 (shown in sectioned view and showing approximated tissue separation 24).

Figure 35:
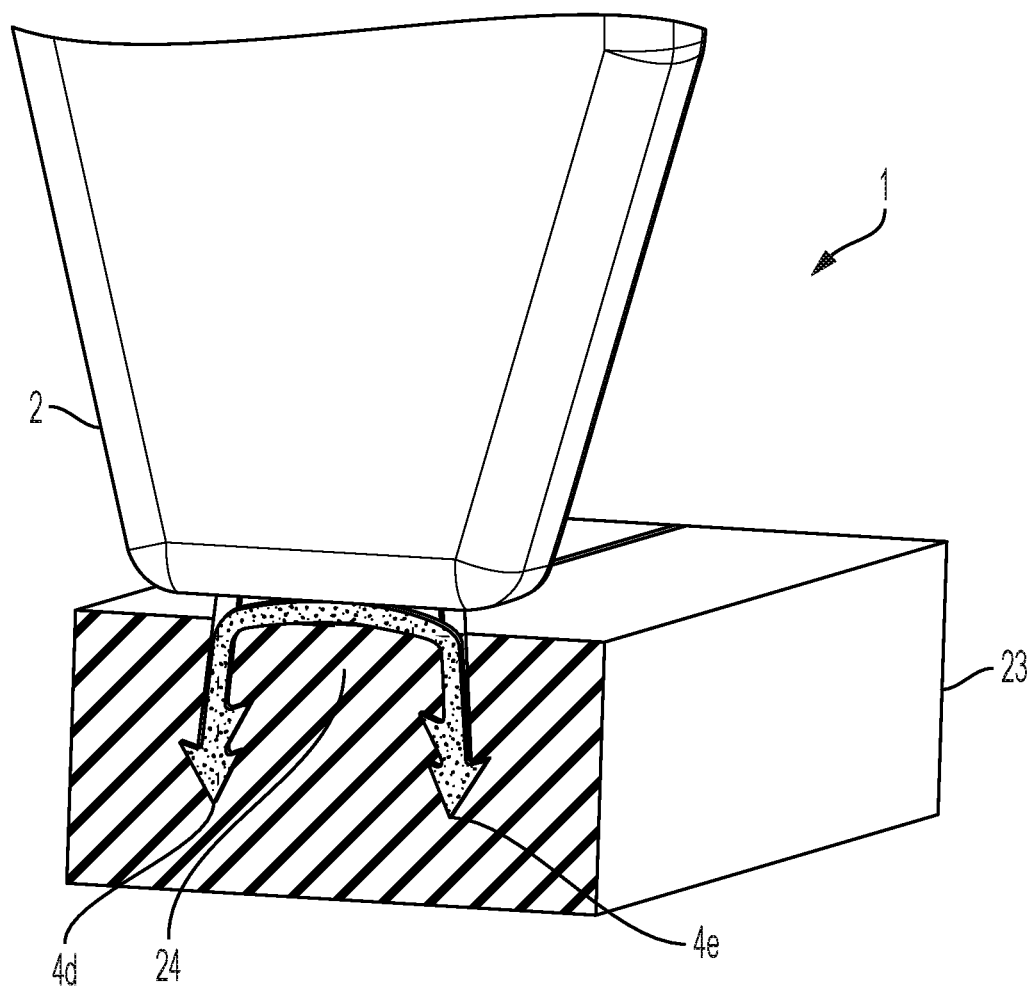
FIG. 35 shows a lateral perspective view of a flexible surgical staple and staple insertion device in accordance with one embodiment of the invention, inserting a staple into a schematic of an approximated tissue.

FIG. 35 shows a lateral perspective view of a flexible surgical staple and staple insertion device in accordance with one embodiment of the invention as shown in FIG. 31, and wherein like numerals refer to identified features. This Figure shows staple insertion device 1 positioned upon having fully inserted an expansively flexible surgical staple 4 into an approximated tissue 23 (shown in sectioned view and showing approximated tissue separation 24). This Figure shows the insertion of flexible surgical staple to close approximated tissue separation 24 in tissue 23.

Figure 36:
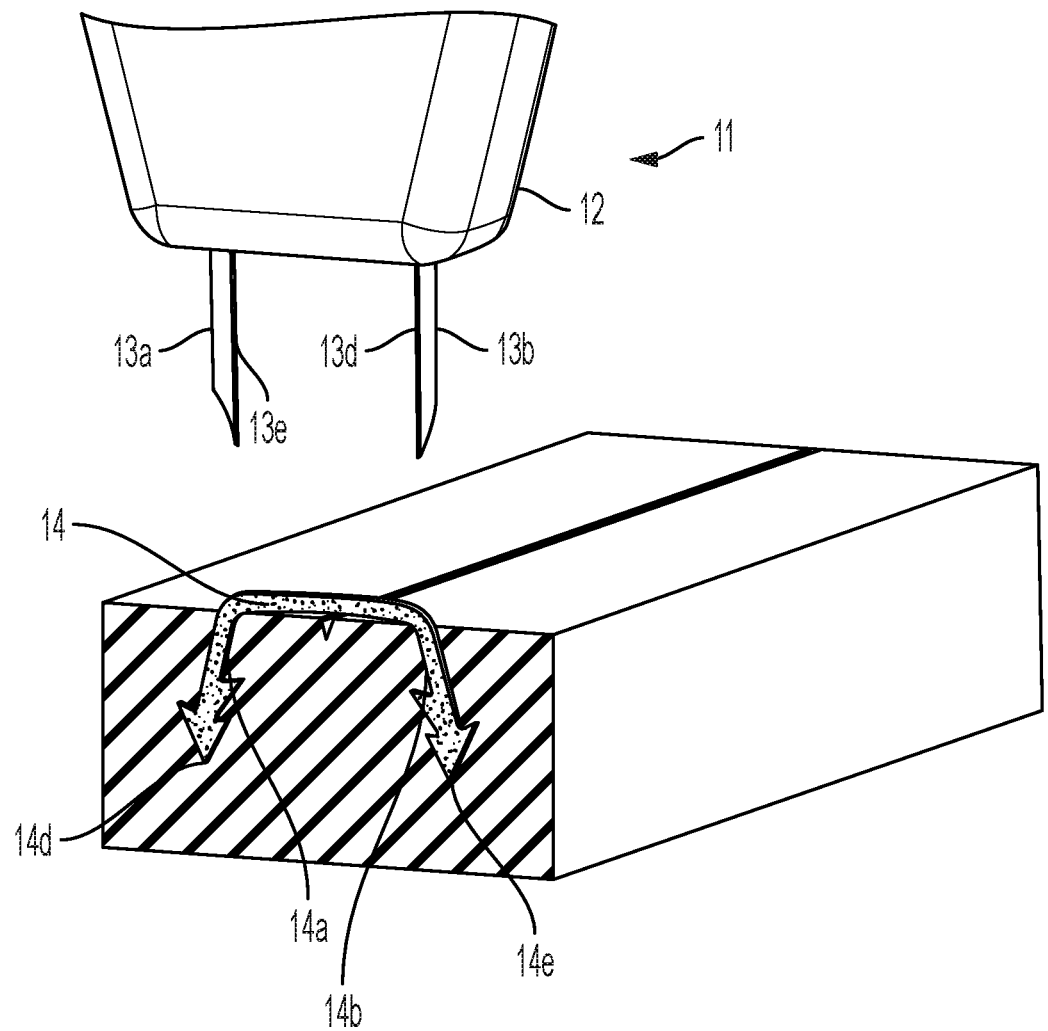
FIG. 36 shows a lateral perspective view of a flexible surgical staple and staple insertion device in accordance with one embodiment of the invention, withdrawing from a schematic of an approximated tissue.

FIG. 36 shows a lateral perspective view of a flexible surgical staple 14 and staple insertion device 11 in accordance with one embodiment of the invention as shown in FIG. 4, and wherein like numerals refer to identified features. This Figure shows staple insertion device 11 positioned after it has been fully withdrawn leaving expansively flexible surgical staple 14 in the approximated tissue 23 (shown in sectioned view and showing approximated tissue separation 24). This Figure shows the complete release and compression of flexible surgical staple 14 to close approximated tissue separation 24 in tissue 23, as expansively flexible surgical staple 14 expand after disengagement from opposed channels 13c and 13d of respective insertion needles 13a and 13b. Staple barbs 14d and 14e are thereby urged into the neighboring tissue to urge it toward approximation, as indicated by the directional arrows.

Figure 37:
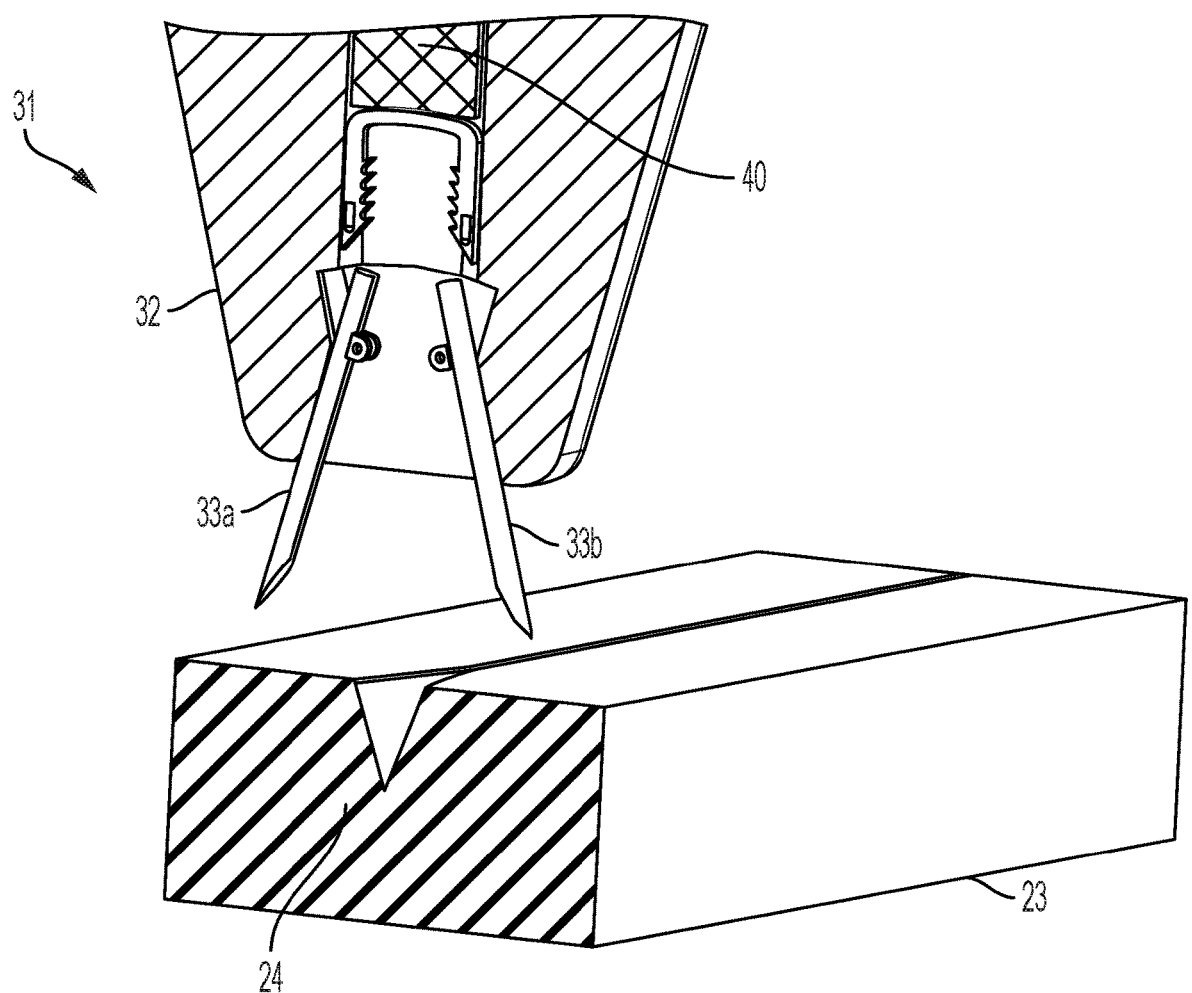
FIG. 37 shows a sectioned lateral perspective view of a flexible surgical staple and staple insertion device in accordance with one embodiment of the invention, positioned so as to insert a staple in a schematic of an approximated tissue.

FIG. 37 shows a sectioned lateral perspective view of a flexible surgical staple and staple insertion device in accordance with another embodiment of the invention, positioned so as to insert a staple in a schematic of an approximated tissue. This Figure shows a staple insertion device 31 positioned over a schematic tissue 23 (shown in sectioned view and showing approximated tissue separation 24).

FIG. 37 shows staple insertion device 31 similar to staple insertion device 11 except that it features moveable insertion needles. Insertion device 31 comprises a handle portion 32 and angled insertion needle portions 33a and 33b having opposed channels 33c and 33d. The insertion needle portions 33a and 33b assist in facilitating tissue approximation during insertion, and in this embodiment are moveable between a converging position to a diverging position by action of manual controller. These manually articulating needle portions 33a and 33b may be used to approximate tissue prior to and or during staple insertion. The manually articulating needle portions 33a and 33b also may be used to hold the staple in an open or closed state prior to release (depending upon whether an expanding or compression staple is used). approximate tissue prior to and or during staple insertion. Articulating needle portions 33a and 33b also may be used to float the articulating needle portions 33a and 33b upon removal in order to minimize tissue damage upon withdrawal of the needles from the insertion site.

Handle portion 31 is provided with a channel 40 that accepts and guides a staple such as staple 21 toward the articulating needle portions 33a and 33b. The staples 21 may be contained in a staple array, such as array 20, and may be serially dispensed through the device by a slider or other actuator.

Opposed channels 33c and 33d hold in sliding engagement flexible staple 21 by engaging staple legs 21a and 21b, while staple bridge portion 21c is held in a relatively expanded state such that the staple legs 21a and 21b are maintained aligned with respective insertion needle portions 33a and 33b once placed into a parallel position.

Figure 38:
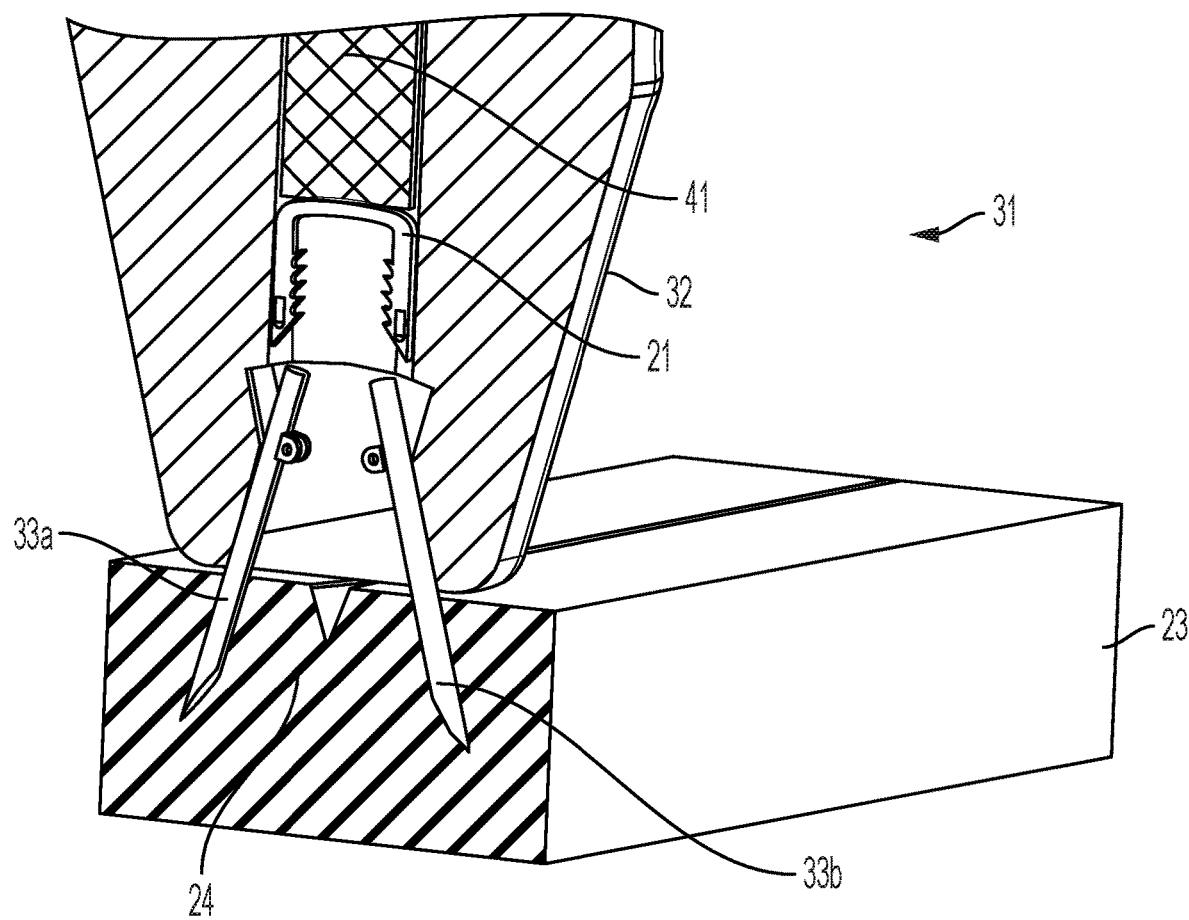
FIG. 38 shows a sectioned lateral perspective view of a flexible surgical staple and staple insertion device in accordance with one embodiment of the invention, inserting a staple into a schematic of an approximated tissue.

FIG. 38 shows a sectioned lateral perspective view of a flexible surgical staple and staple insertion device in accordance with one embodiment of the invention, inserting a staple into a schematic of an approximated tissue.

Figure 39:
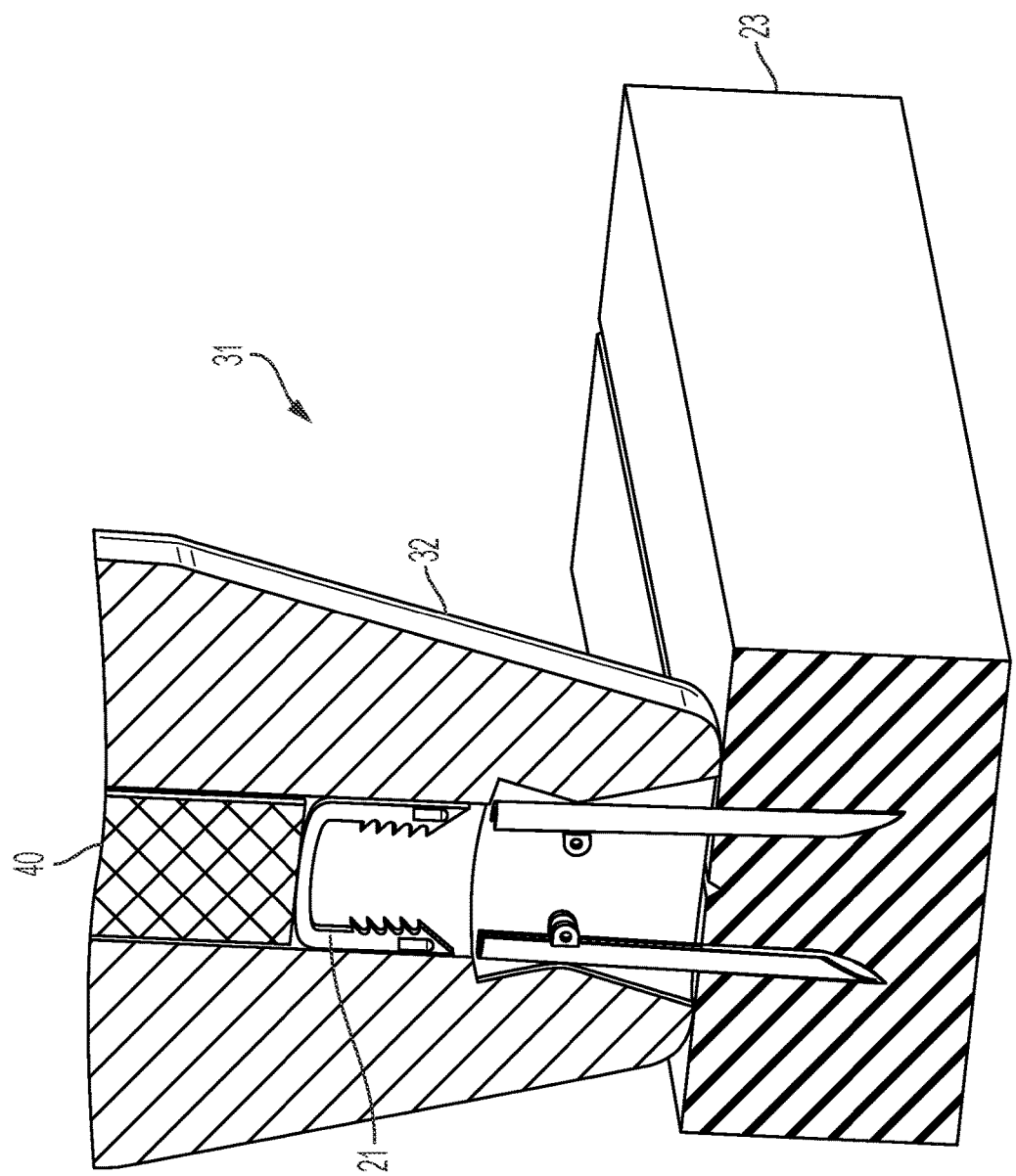
FIG. 39 shows a sectioned lateral perspective view of a flexible surgical staple and staple insertion device in accordance with one embodiment of the invention, inserting a staple into a schematic of an approximated tissue.
Figure 40:
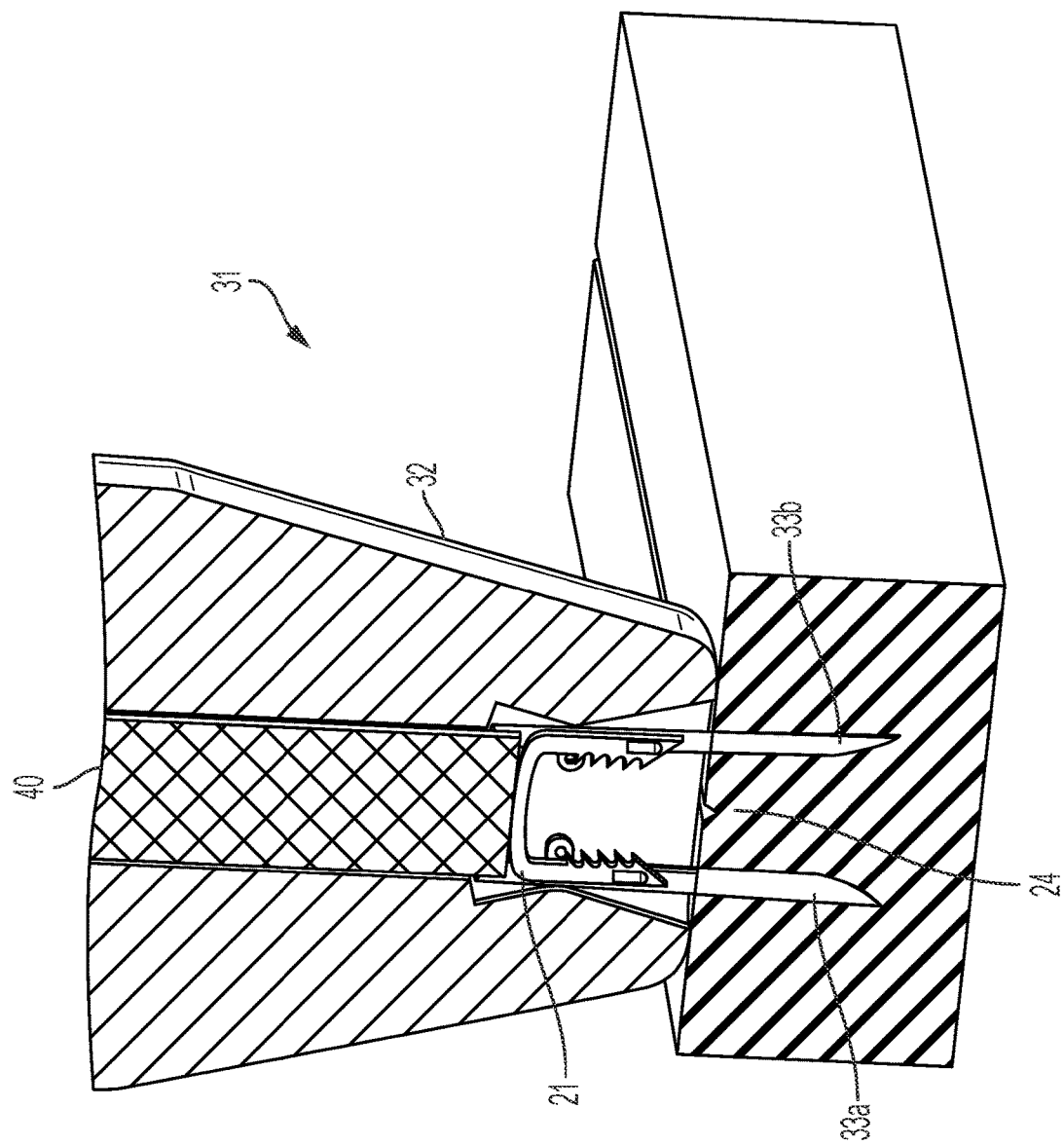
FIG. 40 shows a sectioned lateral perspective view of a flexible surgical staple and staple insertion device in accordance with one embodiment of the invention, inserting a staple into a schematic of an approximated tissue.
Figure 41:
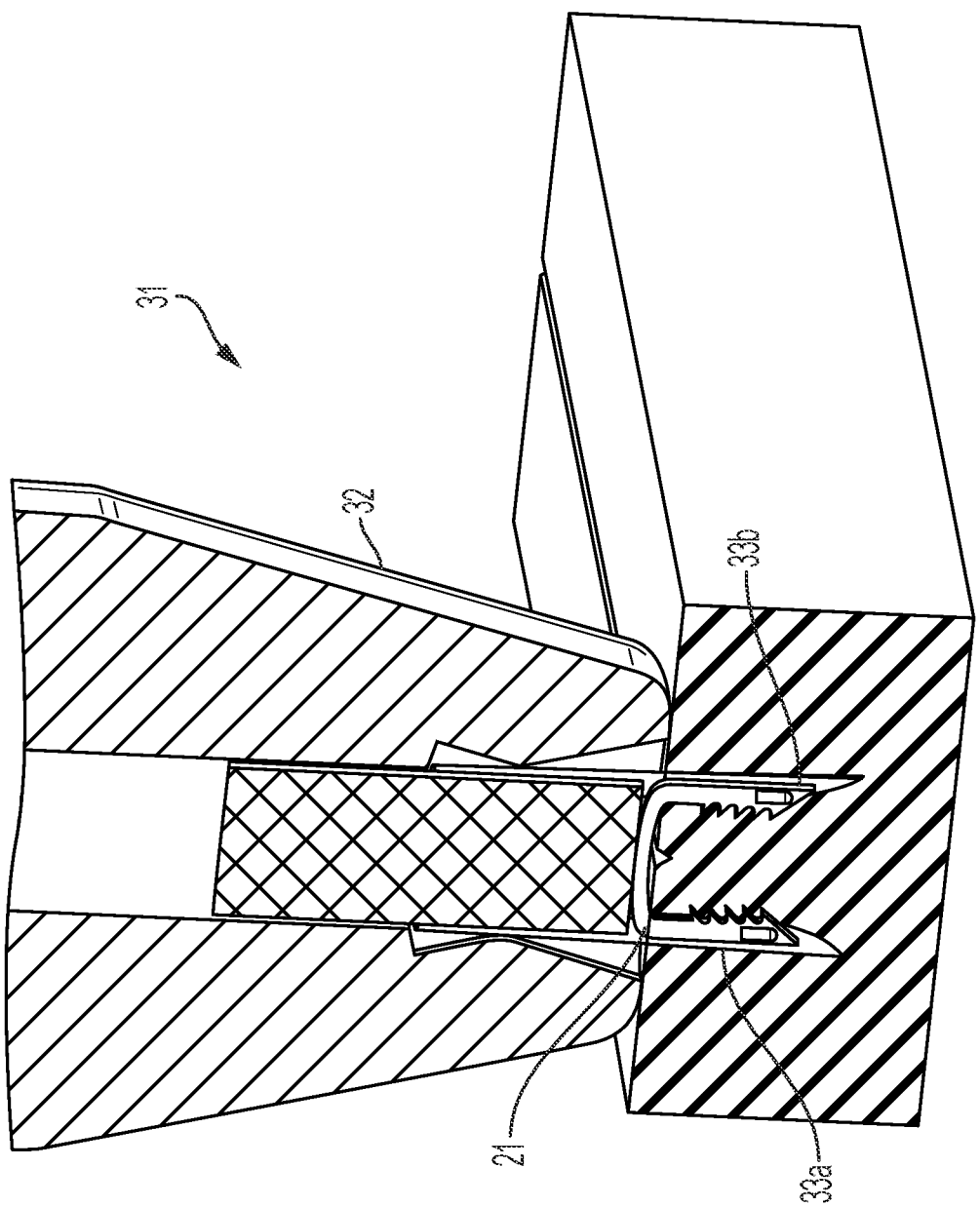
FIG. 41 shows a sectioned lateral perspective view of a flexible surgical staple and staple insertion device in accordance with one embodiment of the invention, inserting a staple into a schematic of an approximated tissue.

FIG. 38 shows staple insertion device 31 whose moveable insertion portions 33a and 33b are moved from a divergent position once inserted as shown in FIG. 38 to a relatively parallel position, thus approximating the tissue 32, as shown by the directional arrows. Once the angled insertion needle portions 33a and 33b are brought parallel, staple 21 is urged forward to engage opposed channels 33c and 33d and is thereby guided through the channels into the tissue, as shown in series in FIGS. 39, 40 and 41.

Figure 42:
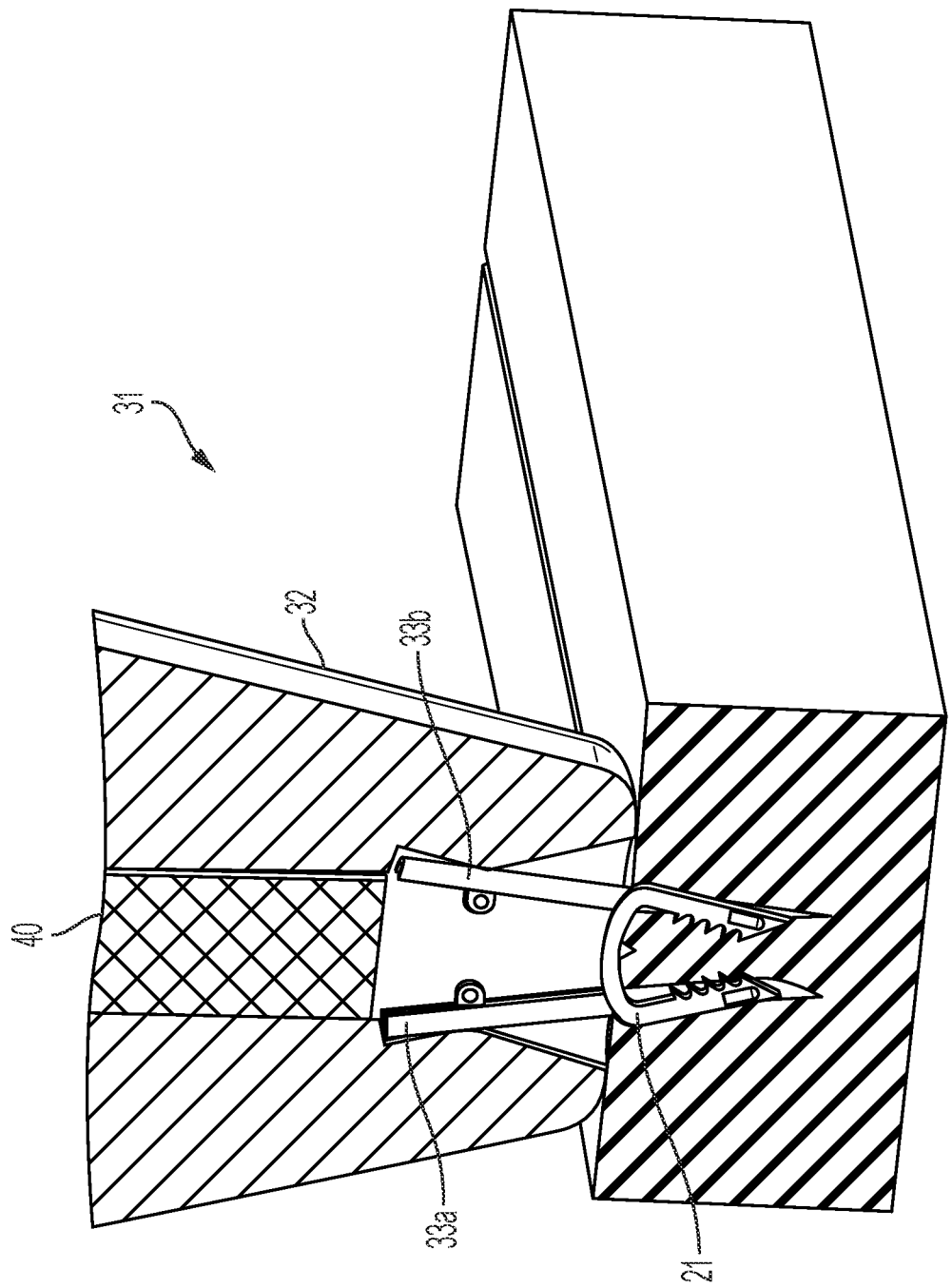
FIG. 42 shows a sectioned lateral perspective view of a flexible surgical staple and staple insertion device in accordance with one embodiment of the invention, inserting a staple into a schematic of an approximated tissue.

FIG. 42 then shows how staple 21, once inserted into tissue 23 is permitted to relax to its compressed state by inward movement of moveable insertion portions 33a and 33b.

Figure 43:
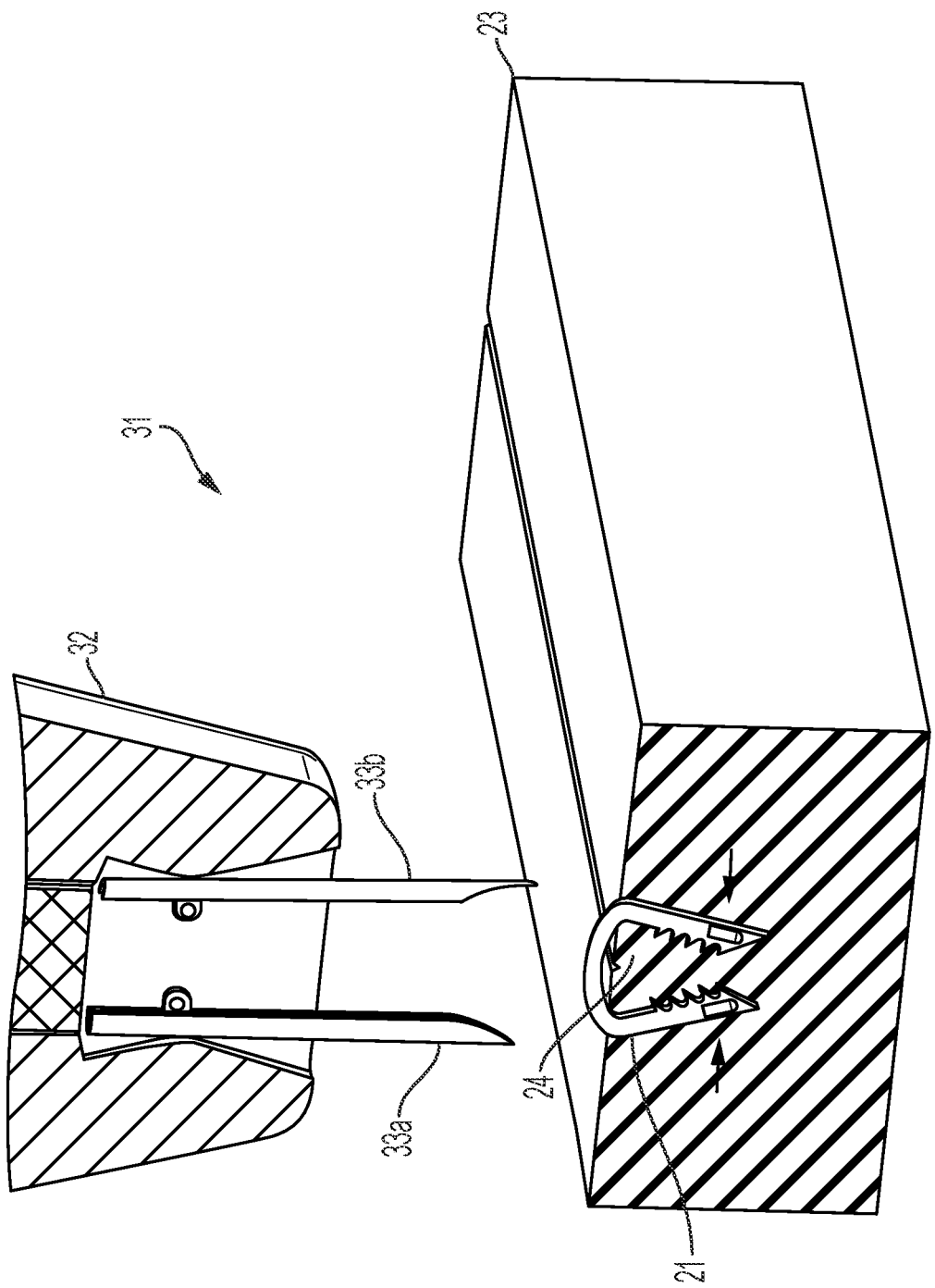
FIG. 43 shows a sectioned lateral perspective view of a flexible surgical staple and staple insertion device in accordance with one embodiment of the invention, withdrawing from a schematic of an approximated tissue.

FIG. 43 shows insertion portions 33a and 33b having been fully withdrawn leaving compressively flexible surgical staple 21 in the approximated tissue 23, having completely released the compressing flexible surgical staple 21 to close approximated tissue separation 24 in tissue 23.

Figure 44:
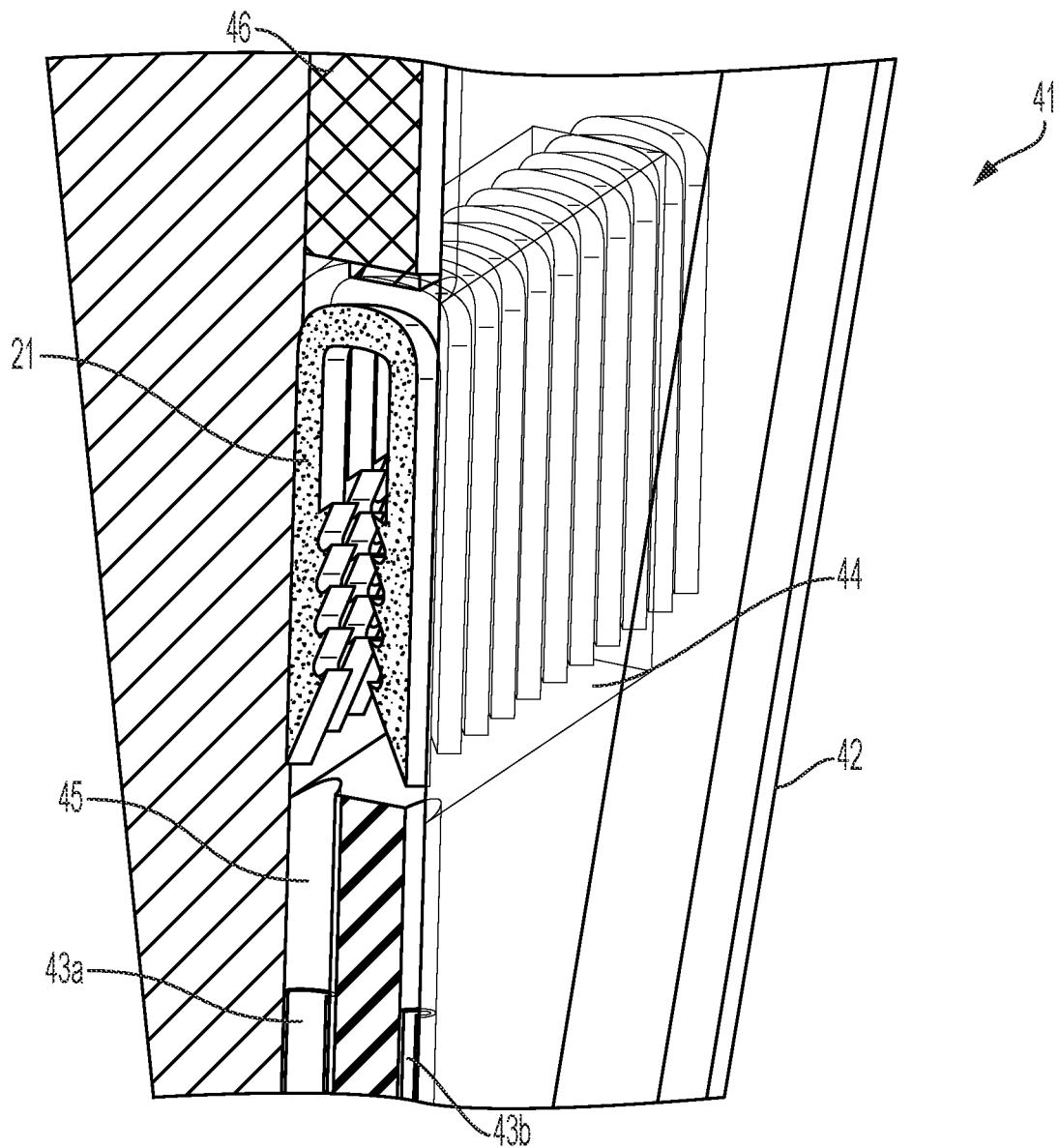
FIG. 44 shows a detailed sectioned lateral perspective view of a magazine of flexible surgical staples in a staple insertion device in accordance with one embodiment of the invention.

FIG. 44 shows a detailed sectioned lateral perspective view of a magazine of flexible surgical staples in a staple insertion device in accordance with another embodiment of the invention.

FIG. 44 shows staple insertion device 41 similar to staple insertion device 31 except that it shows a staple cartridge and driver.

Insertion device 41 comprises a handle portion 42 and insertion needle portions (note shown, but may be straight, angled, or moveable, as described above). Insertion device 41 further comprises magazine 44 adapted to hold staple array such as staple array 20 or similar stacked staple arrays. Channel 45 in handle 42 that accepts and guides a staple such as staple 21 toward the parallel needle portions 43a and 43b. The staples 21 may be contained in a staple array, such as array 20, and may be serially dispensed through the device by a slider 46 or another actuator.

Insertion needle portions 43a and 43b have opposed channels 43c and 43d. The insertion needle portions 43a and 43b accept each staple 21 in series as each is sheared from the staple array 20 and urged along channel 45 toward and to engagement with Insertion needle portions 43a and 43b.

Figure 45:
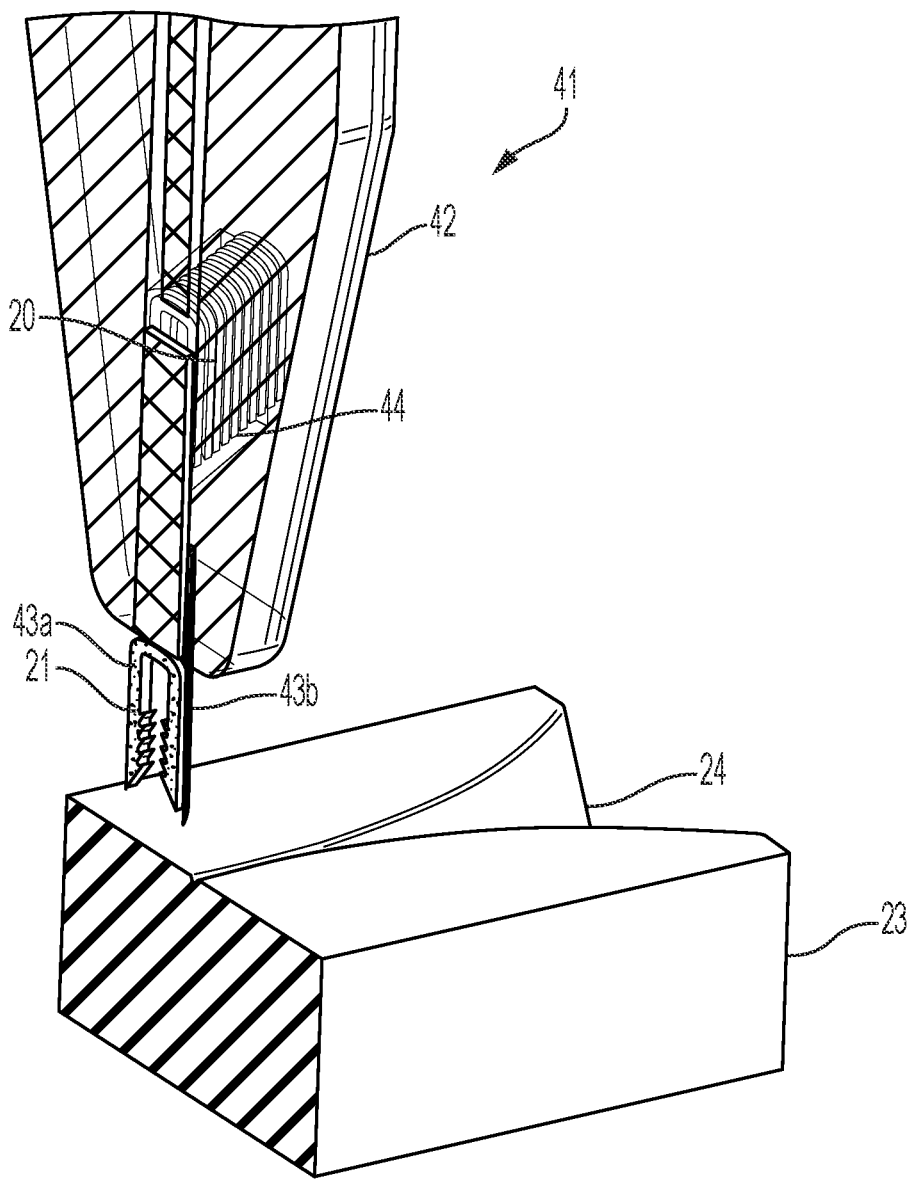
FIG. 45 shows a detailed sectioned lateral perspective view of a magazine of flexible surgical staples in a staple insertion device in accordance with one embodiment of the invention, positioned so as to insert a staple in a schematic of an approximated tissue.

FIG. 45 shows a detailed sectioned lateral perspective view of a magazine 44 of flexible surgical staples 20 in a staple insertion device 41 and showing that the magazine may be spring loaded to urge each staple in the series into the channel position after action of the slider 46 recedes.

Figure 46:
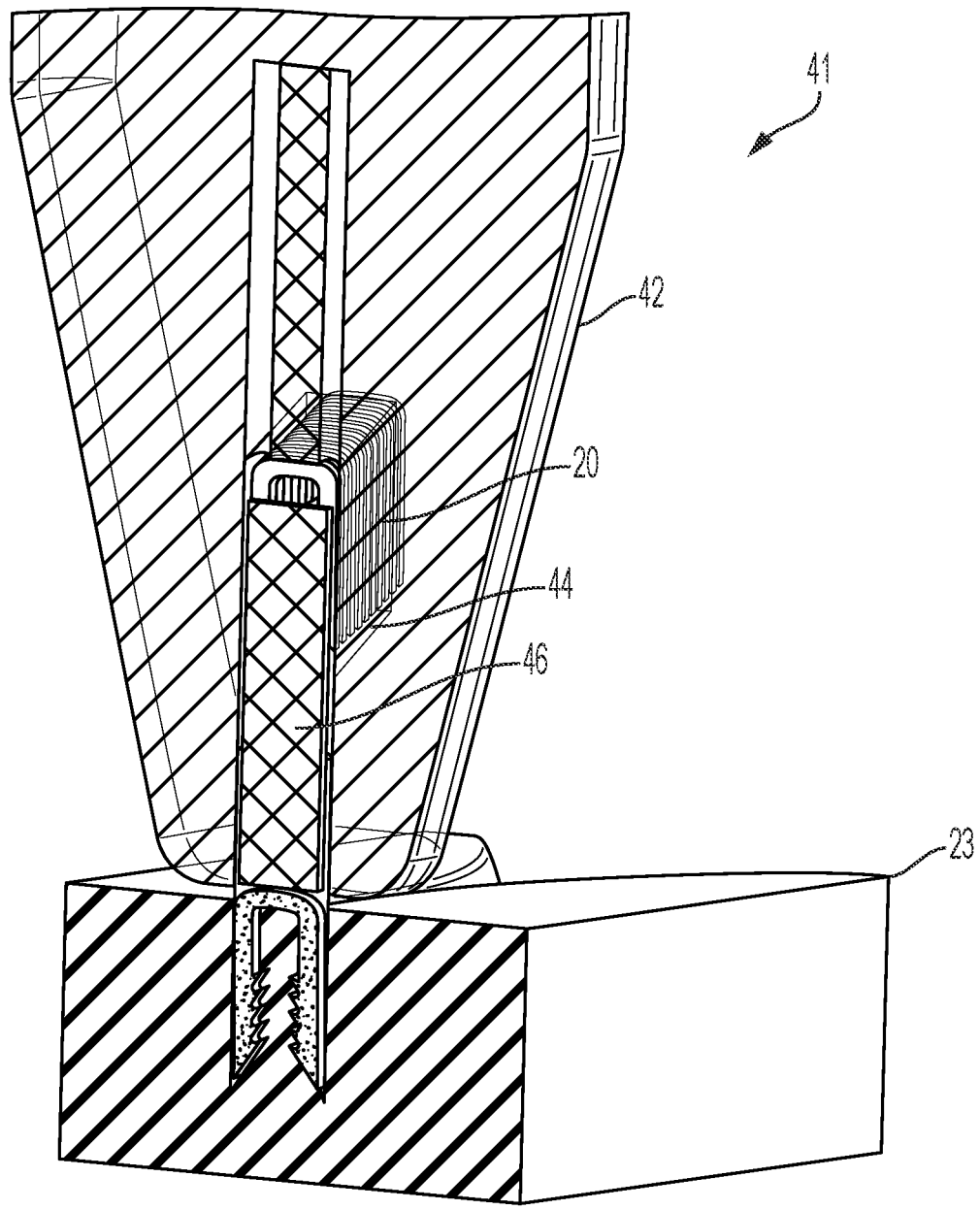
FIG. 46 shows a detailed sectioned lateral perspective view of a magazine of flexible surgical staples in a staple insertion device in accordance with one embodiment of the invention, inserting a staple into a schematic of an approximated tissue.
Figure 47:
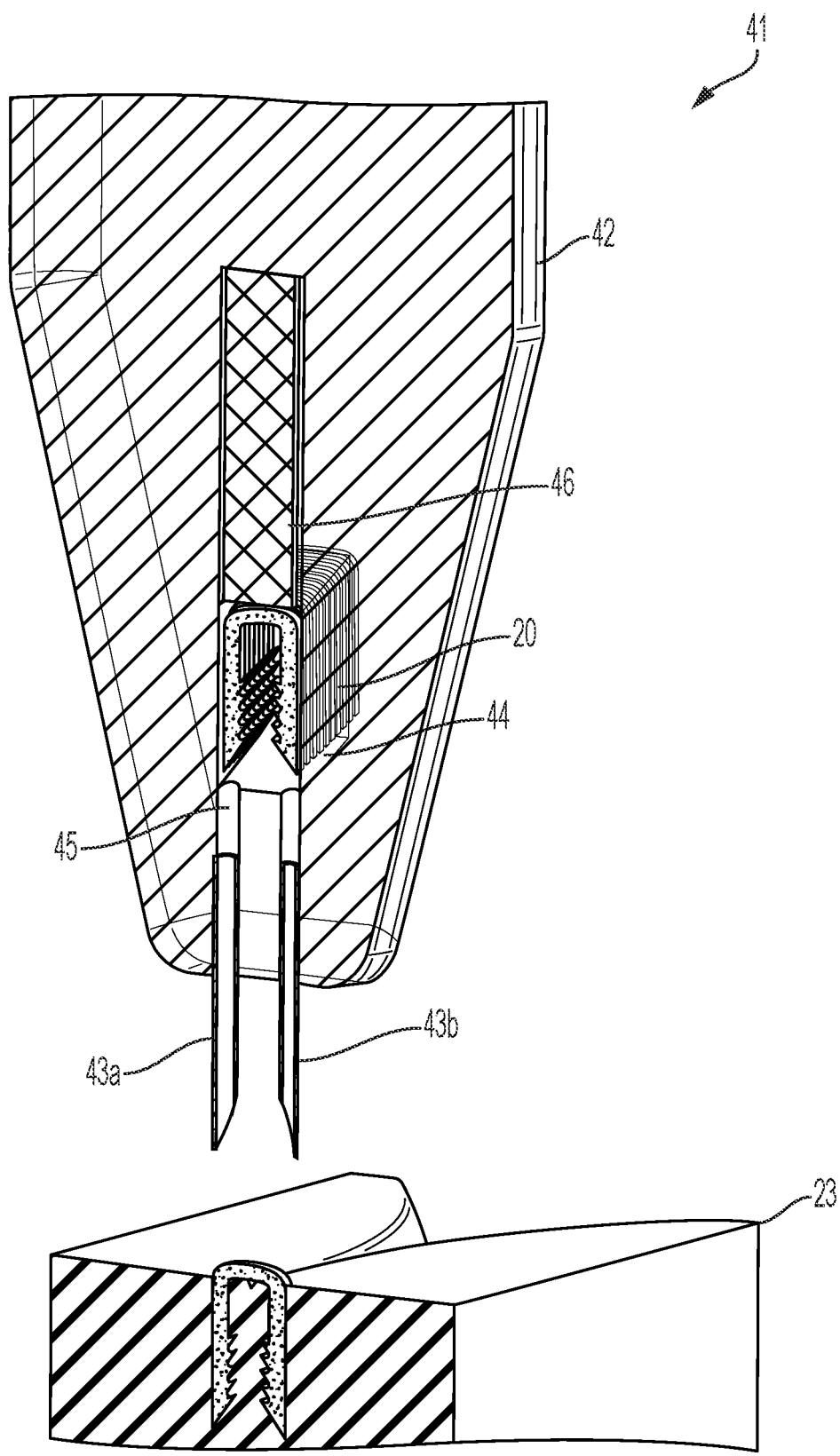
FIG. 47 shows a detailed sectioned lateral perspective view of a magazine of flexible surgical staples in a staple insertion device in accordance with one embodiment of the invention, withdrawing from a schematic of an approximated tissue.
Figure 48:
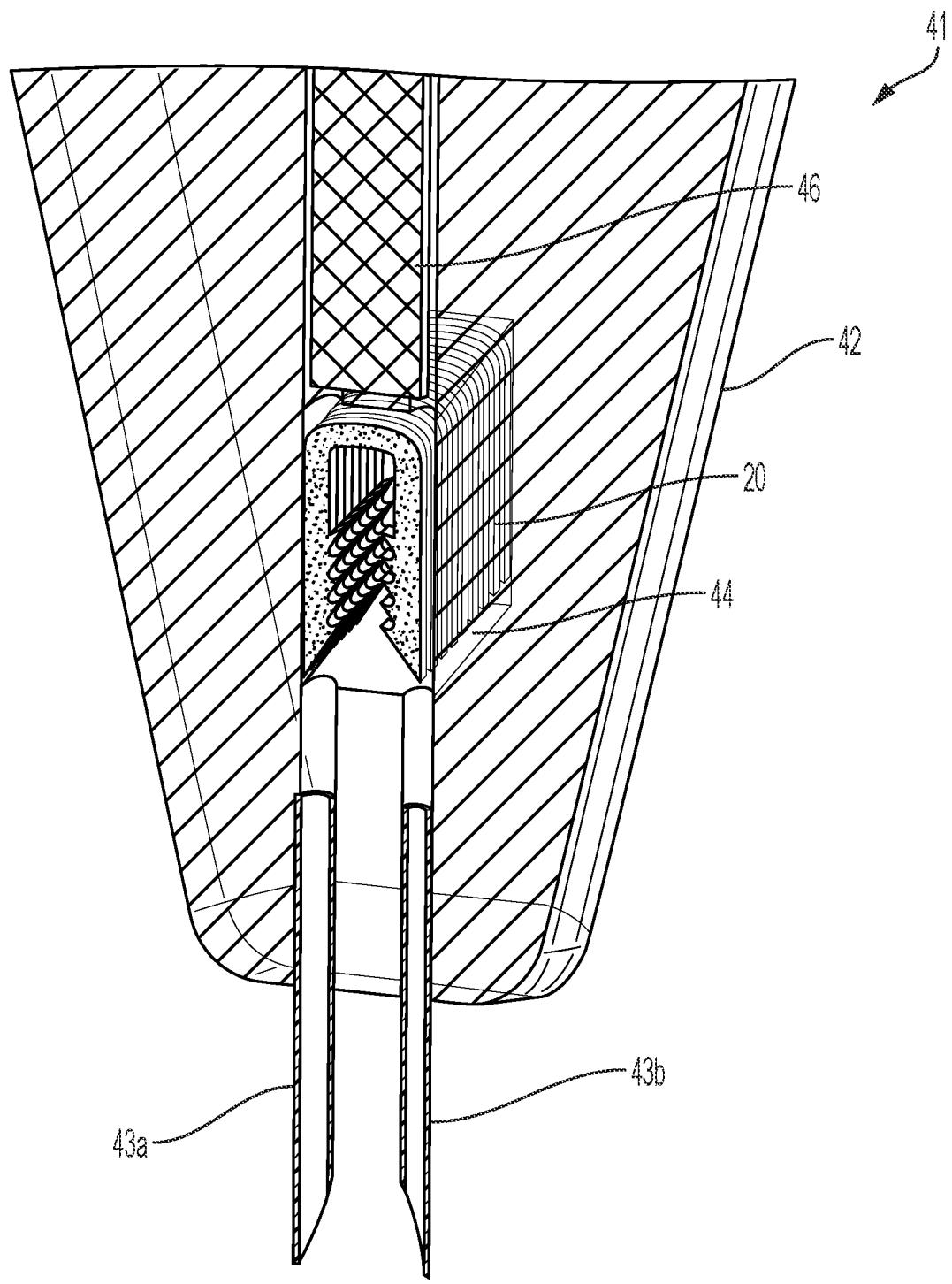
FIG. 48 shows a detailed sectioned lateral perspective view of a magazine of flexible surgical staples in a staple insertion device in accordance with one embodiment of the invention.

The forward action of the slider 46 is shown in FIG. 46 while the rearward action of the slider 46 is shown in FIGS. 47 and 48.

Figure 49:
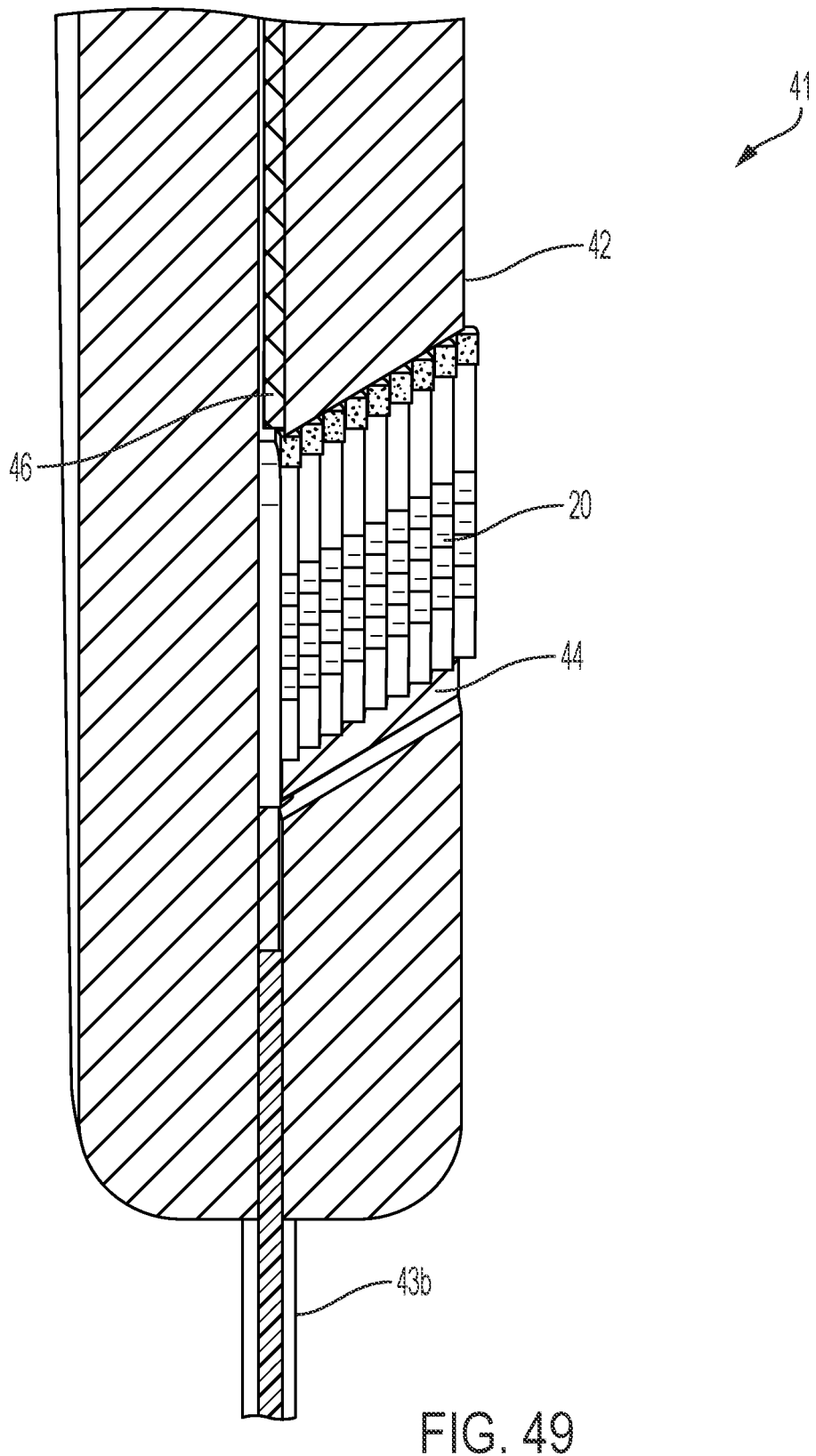
FIG. 49 shows a detailed sectioned lateral view of a magazine of flexible surgical staples in a staple insertion device in accordance with one embodiment of the invention.

FIG. 49 shows a detailed sectioned lateral view of a magazine 44 of flexible surgical staples 20 in a staple insertion device 41 and shows the spring loading of staple array 20 within magazine 44.

Figure 50:
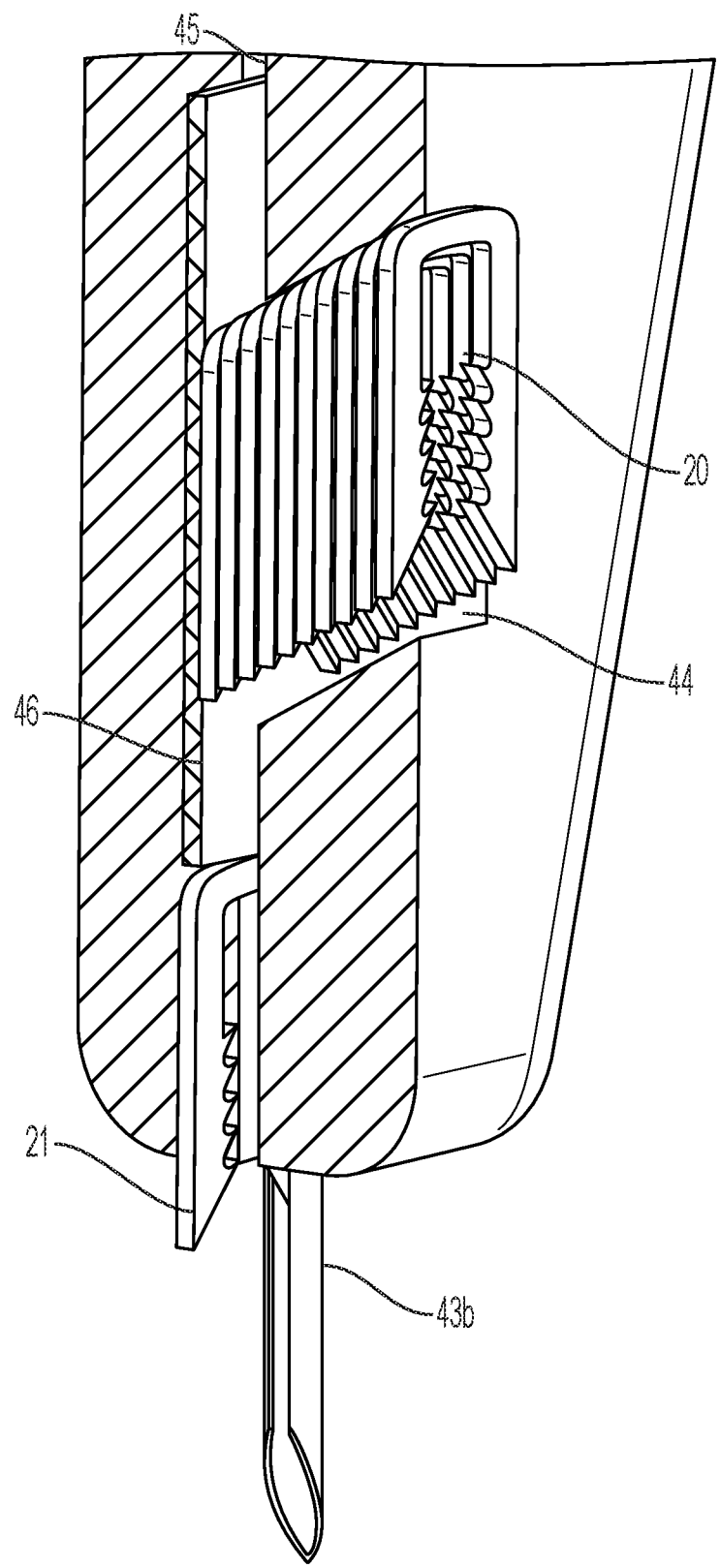
FIG. 50 shows a detailed sectioned lateral view of a magazine of flexible surgical staples in a staple insertion device in accordance with one embodiment of the invention.
Figure 51:
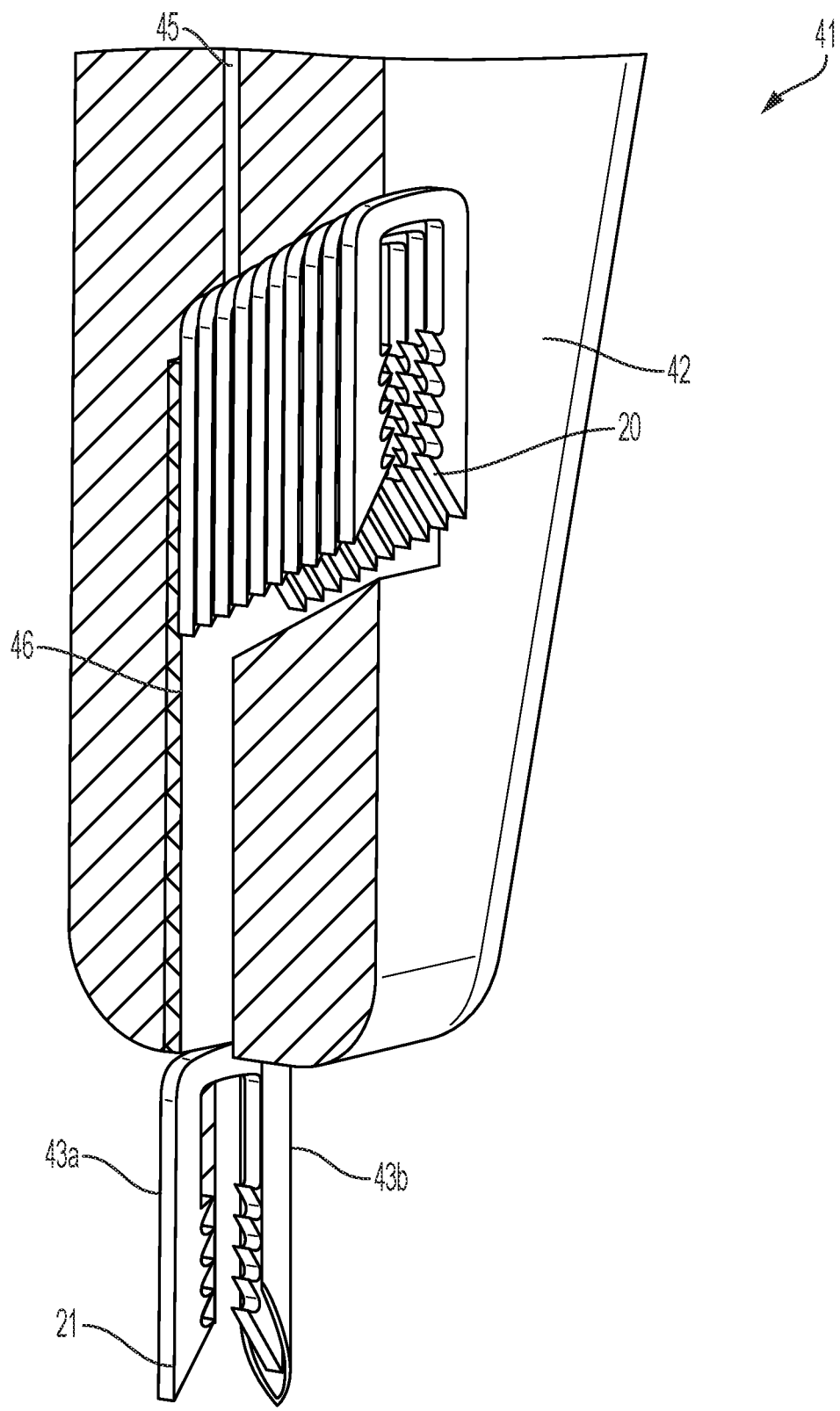
FIG. 51 shows a detailed sectioned lateral view of a magazine of flexible surgical staples in a staple insertion device in accordance with one embodiment of the invention.

FIGS. 50 and 51 shows a detailed sectioned lateral view of a magazine 44 of flexible surgical staples 20 in a staple insertion device 41 and show in additional detail the disposition of the slider 46, staple array 20 and staple 21 as it is urged through the channel 45 to engagement with insertion needle portions 43a and 43b for insertion into the tissue.

Figure 52:
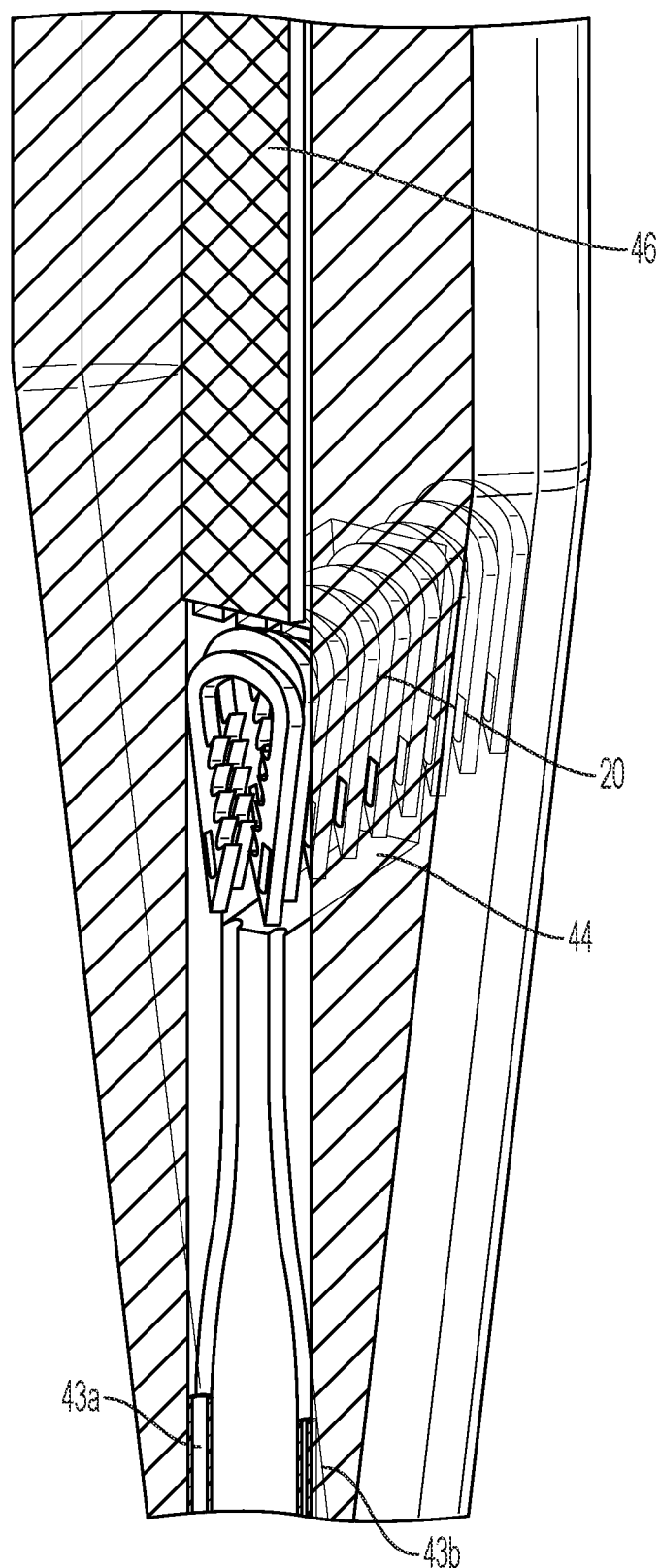
FIG. 52 shows a detailed sectioned lateral view of a magazine of flexible surgical staples in a staple insertion device in accordance with one embodiment of the invention.
Figure 53:
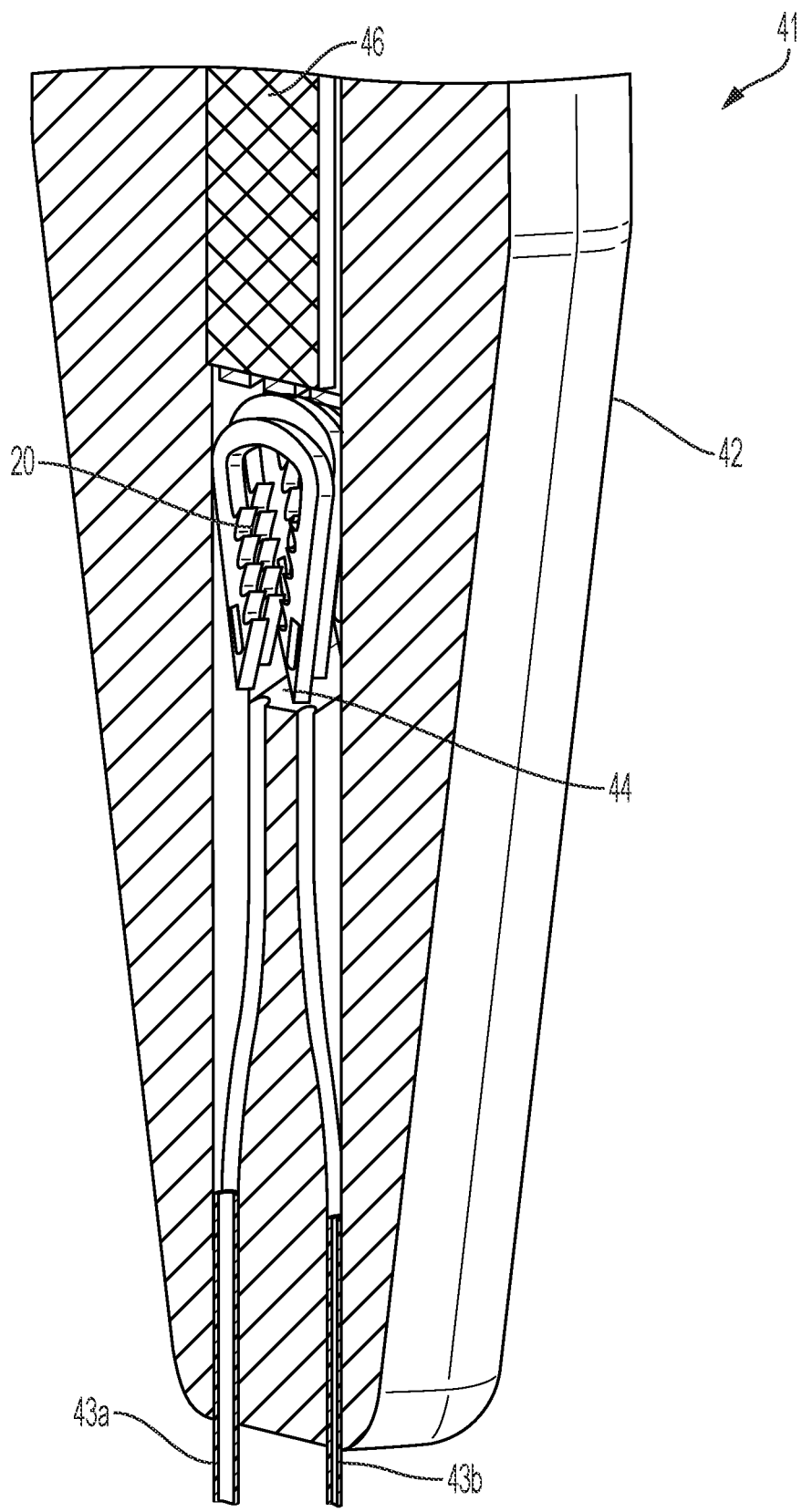
FIG. 53 shows a detailed sectioned lateral view of a magazine of flexible surgical staples in a staple insertion device in accordance with one embodiment of the invention.
Figure 54:
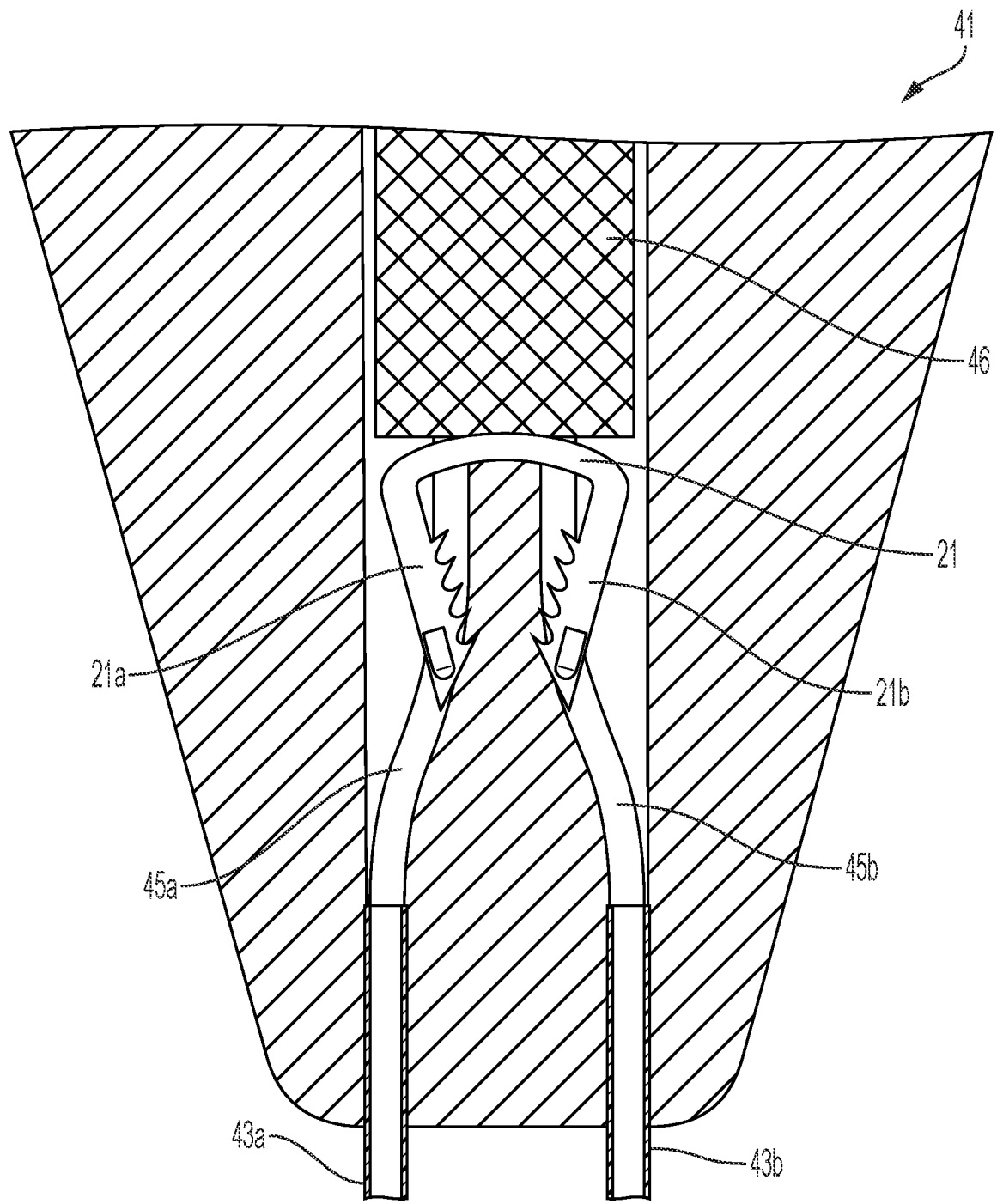
FIG. 54 shows a detailed sectioned lateral view of a flexible surgical staples in a staple insertion device in accordance with one embodiment of the invention.
Figure 55:
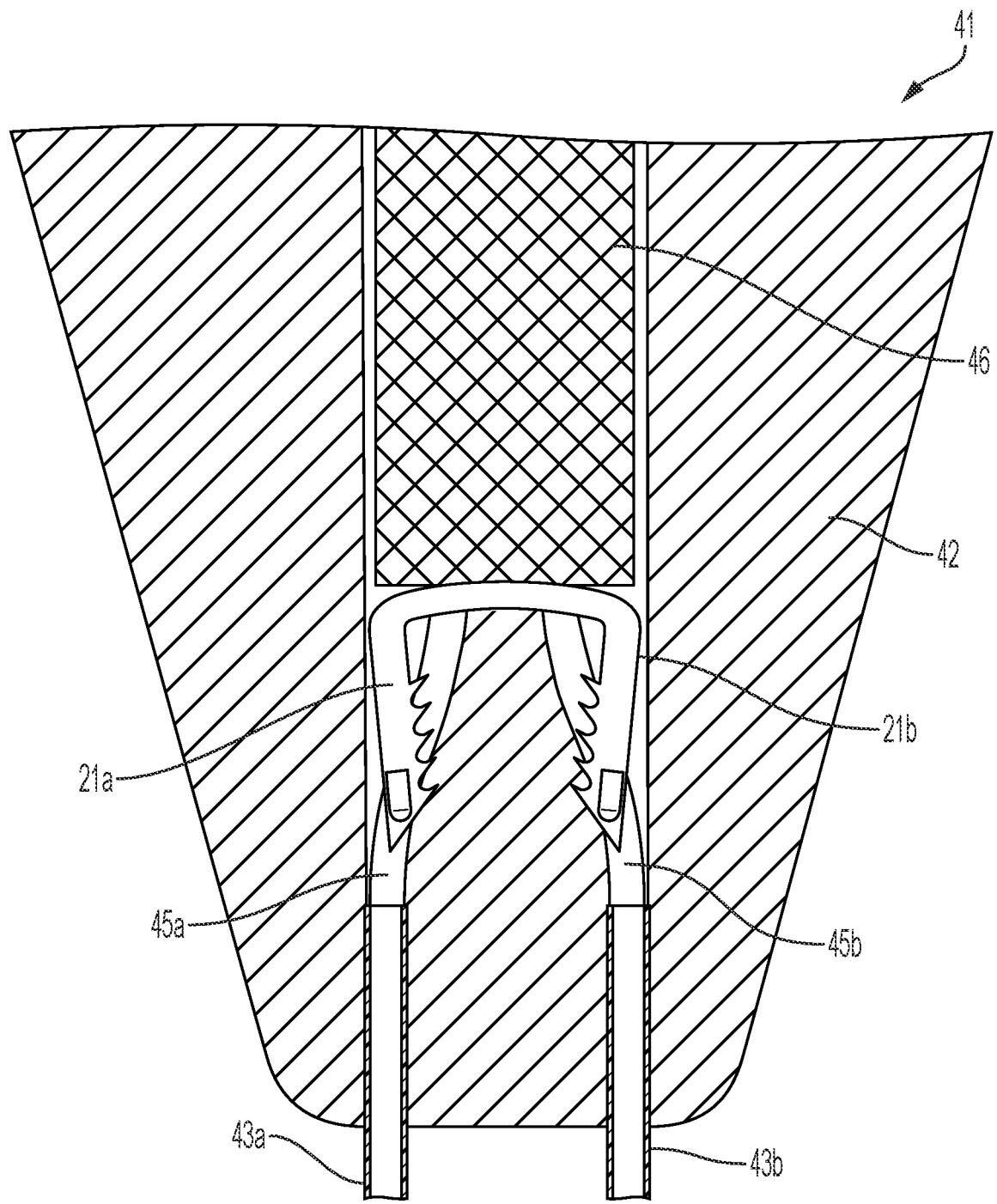
FIG. 55 shows a detailed sectioned lateral view of a flexible surgical staples in a staple insertion device in accordance with one embodiment of the invention.
Figure 56:
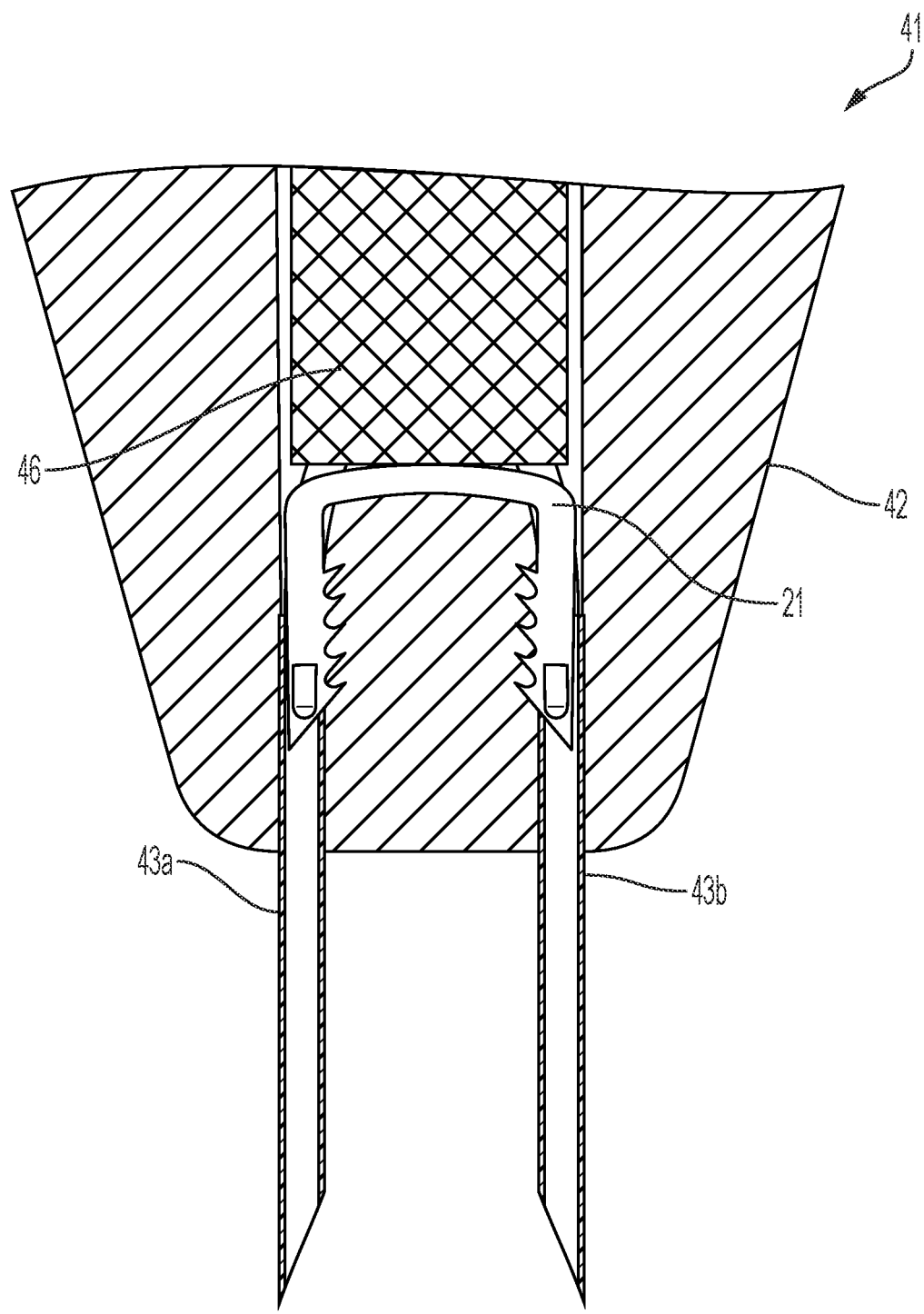
FIG. 56 shows a detailed sectioned lateral view of a flexible surgical staples in a staple insertion device in accordance with one embodiment of the invention.
Figure 57:
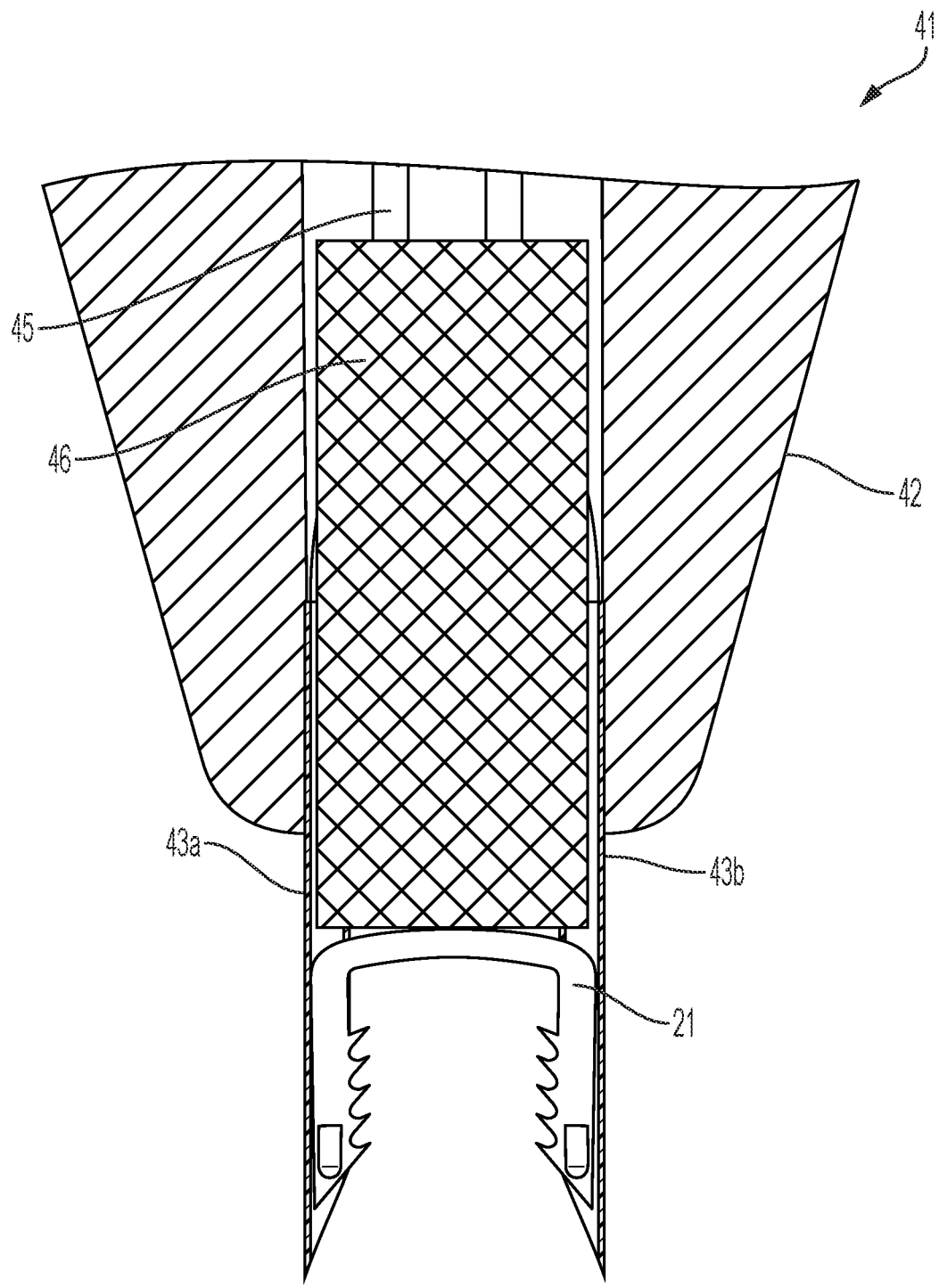
FIG. 57 shows a detailed sectioned lateral view of a flexible surgical staples in a staple insertion device in accordance with one embodiment of the invention.
Figure 58:
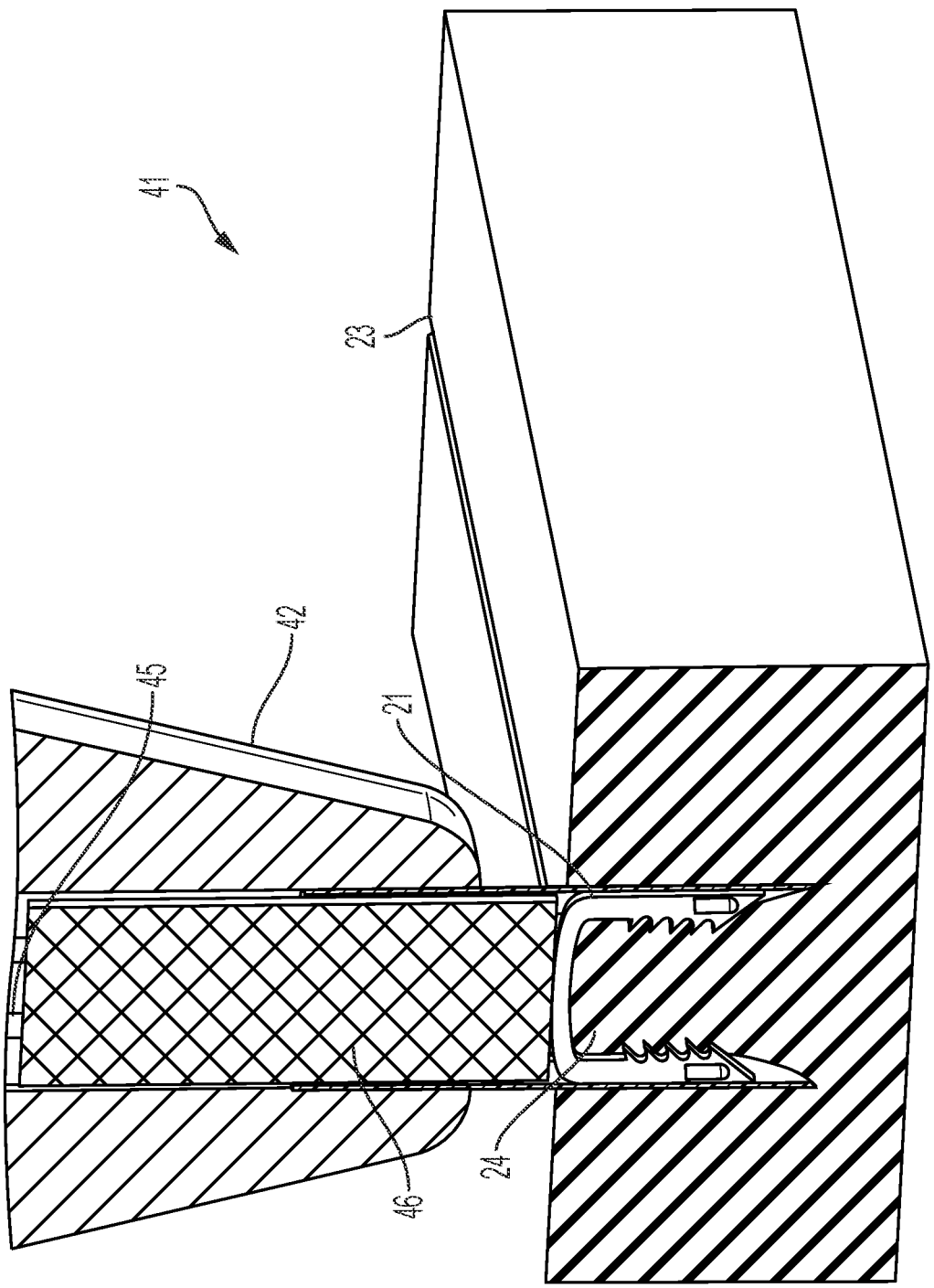
FIG. 58 shows a detailed sectioned lateral perspective view of a magazine of flexible surgical staples in a staple insertion device in accordance with one embodiment of the invention, inserting a staple into a schematic of an approximated tissue.
Figure 59:
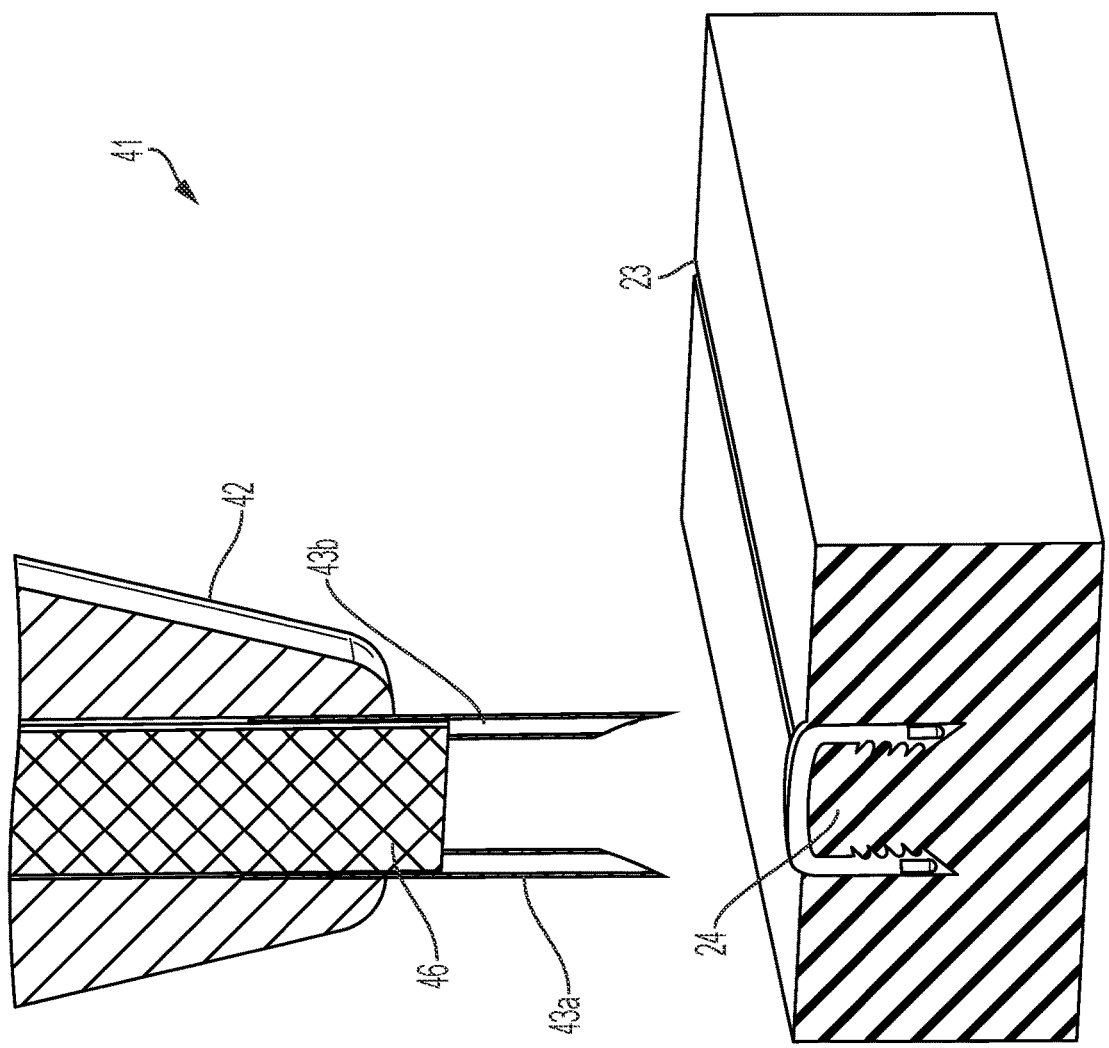
FIG. 59 shows a detailed sectioned lateral perspective view of a magazine of flexible surgical staples in a staple insertion device in accordance with one embodiment of the invention, withdrawing from a schematic of an approximated tissue.

FIG. 52 shows a detailed sectioned lateral view of a magazine of flexible surgical staples in a staple insertion device in accordance with one embodiment of the invention. This Figure shows in additional detail the disposition of the slider 46, staple array 20 and staple 21 as it is urged through the channel 45 to engagement with insertion needle portions 43a and 43b for insertion into the tissue. This Figure shows a variant wherein channel 45 below the staple array may be shaped into tracks 45a and 45b to grip the staple and expand it as it travels along its path to the insertion needle portions 43a and 43b. The staple legs may be supplied with the above-described supplemental three-dimensional features, such as cylindrical section portions to permit the opposed channels 45a and 45b to grip the staple. This is shown in additional detail in FIGS. 53, 54 and 55, showing how staple legs 21a and 21b respectively grip opposed channels 45a and 45b, and deform it as it moves forward toward insertion needle portions 43a and 43b.

FIG. 56-59 show a detailed sectioned lateral view of a flexible surgical staple 21 in a staple insertion device 41 in accordance with one embodiment of the invention, and wherein like numerals refer to identified features. The Figures show the series of steps and the action of the staple insertion device 41 and its slider 46 to urge the staple 21 into position through channels 45a and 45b to its terminal position between insertion needle portions 43a and 43b for insertion into tissue 23.

Figure 60:
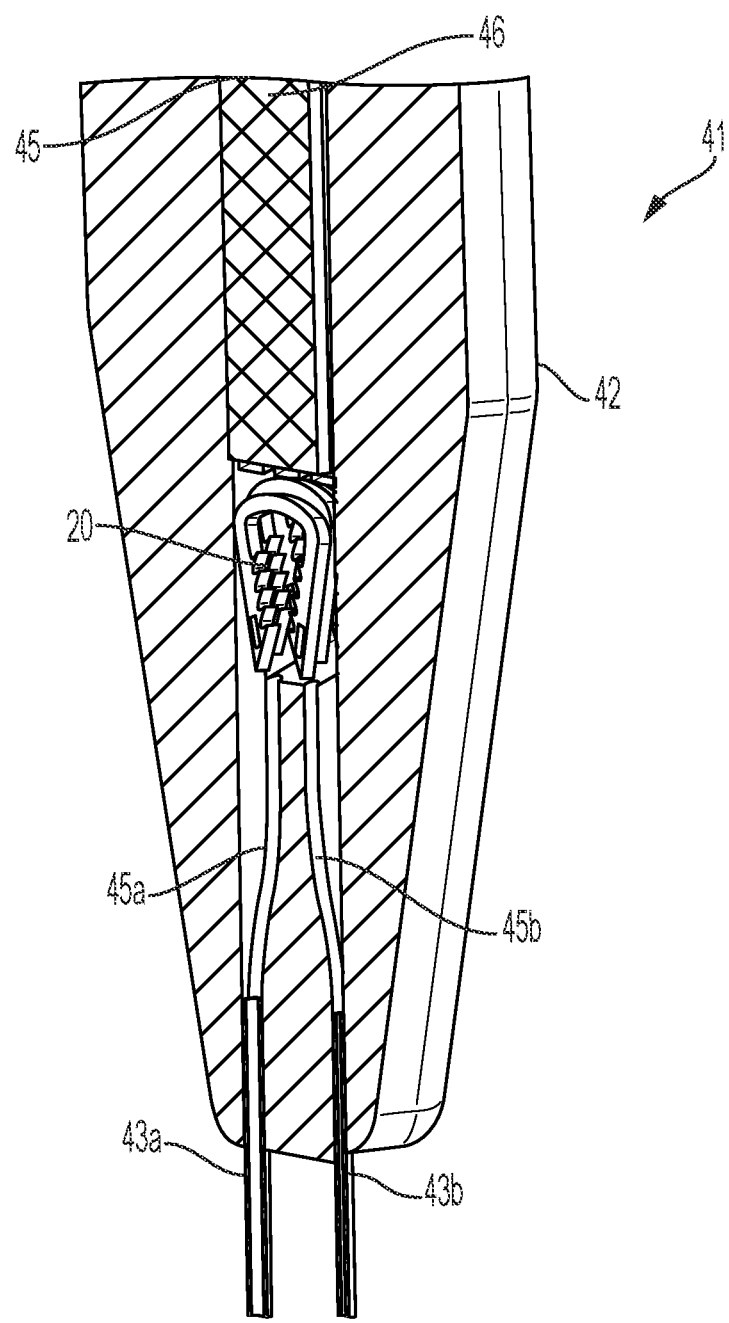
FIG. 60 shows a detailed sectioned lateral view of a flexible surgical staples in a staple insertion device in accordance with one embodiment of the invention.

FIG. 60 shows a detailed sectioned lateral view of a flexible surgical staples in a staple insertion device in accordance with one embodiment of the invention. This Figure shows a variant wherein channel 45 below the staple array may be shaped into tracks 45a and 45b to grip the staple and expand it as it travels along its path to the insertion needle portions 43a and 43b.

Figure 61:
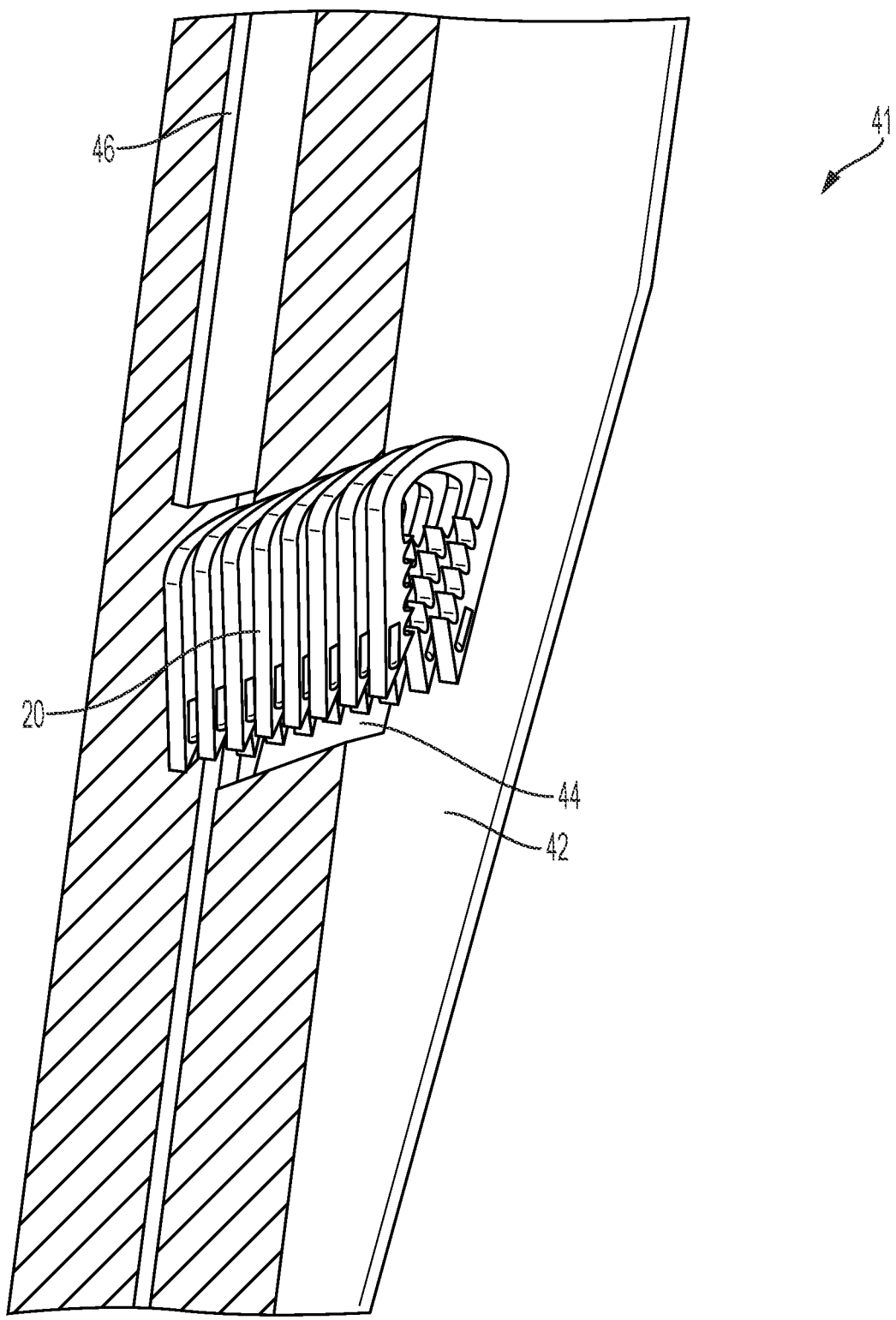
FIG. 61 shows a detailed sectioned lateral view of a flexible surgical staples in a staple insertion device in accordance with one embodiment of the invention.

FIG. 61 shows a detailed sectioned lateral view of a flexible surgical staples in a staple insertion device in accordance with one embodiment of the invention. FIG. 61 shows a detailed sectioned lateral view of a magazine 44 of flexible surgical staples 20 in a staple insertion device 41 and shows the spring loading of staple array 20 within magazine 44.

Figure 62A:
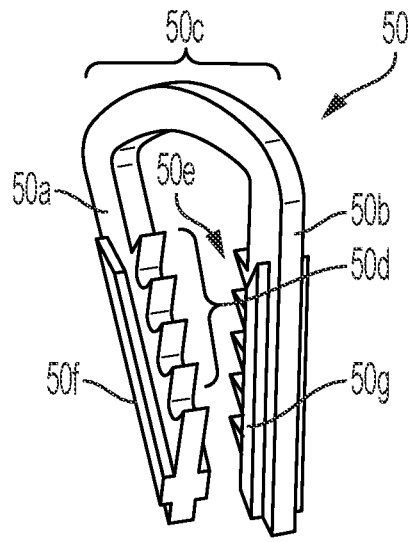
FIGS. 62a and 62b show lateral perspective views of a flexible surgical staple in accordance with one embodiment of the invention.
Figure 62B:
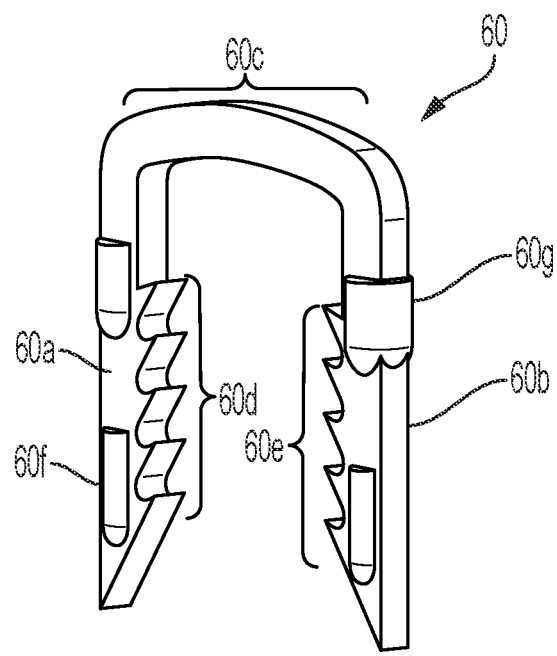

FIGS. 62a and 62b show lateral perspective views of flexible surgical staple 50 and 60 in accordance with embodiment of the invention. FIG. 62a shows surgical staple 50 having staple legs 50a and 50b and staple bridge portion 50c. Flexible staple legs 50a and 50b are provided with one or more inwardly directed barbs 50d and 50e that permit insertion while securing the staple 50 in place in the tissue once the flexible staple 50 is in its relaxed compressed state. The staple legs may also be provided with supplemental three-dimensional features, such as rectangular section portions to permit the opposed channels (such as 3c and 3d or 13c and 13d, that may have squared interior surfaces) to better accommodate the staple legs 50a and 50b to better maintain them in an expanded position prior to release. Likewise, such supplemental three-dimensional features may be used in another variant of the invention wherein the flexible staple with converging staple legs is retained in a relatively tensed and expanded position (such as wherein the staple legs are held substantially parallel in accordance with the position of opposed channels (such as 3c and 3d)), and is released after insertion to return to a closed position to grip the tissue for approximation. FIG. 62b shows surgical staple 60 having staple legs 60a and 60b and staple bridge portion 60c. Flexible staple legs 60a and 60b are provided with one or more inwardly directed barbs 60d and 60e that permit insertion while securing the staple 60 in place in the tissue once the flexible staple 60 is in its relaxed compressed state. The staple legs may also be provided with supplemental three-dimensional features, such as cylindrical section portions 60f and 60g to permit the opposed channels (such as 3c and 3d or 13c and 13d, that may have rounded interior surfaces) to better accommodate the staple legs 60a and 60b to better maintain them in an expanded position prior to release.

Figure 63A:
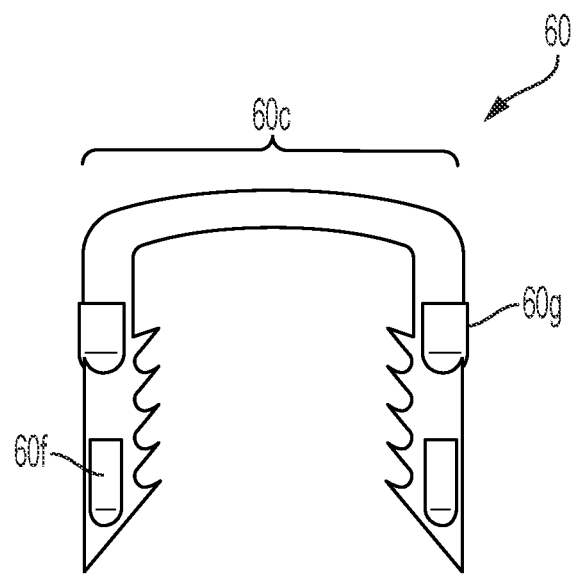
FIGS. 63a and 63b show respectively a frontal view and a lateral view of a flexible surgical staple in accordance with one embodiment of the invention.
Figure 63B:
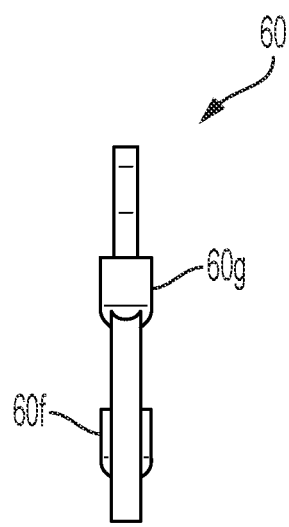
Figure 64A:
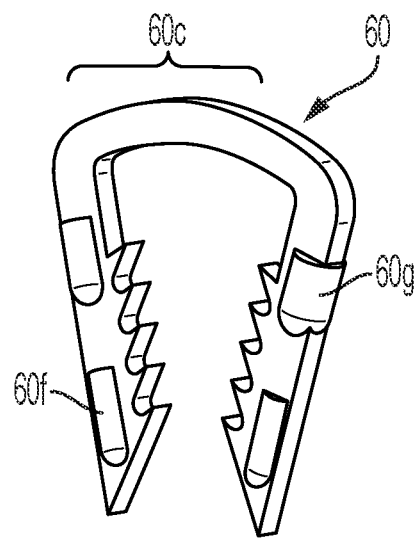
FIGS. 64a and 64b show lateral perspective views of a flexible surgical staple in accordance with one embodiment of the invention.

FIGS. 63a, 63b and 64a show respectively a frontal view, a lateral view, and a perspective view of a flexible surgical staple in accordance with the embodiment of the invention shown in FIG. 62b, and wherein like numerals refer to identified features. FIG. 63a shows how the staple may be retained in an expanded position by using section portions 60f and 60g for insertion prior to release, as indicated by the directional arrows.

Figure 64B:
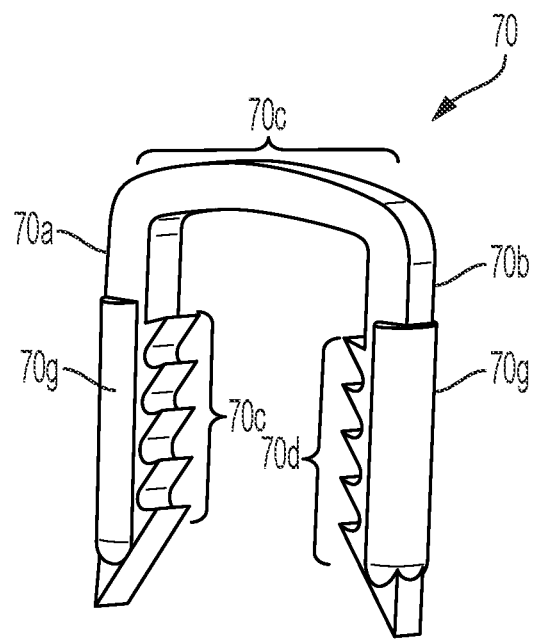
Figure 65A:
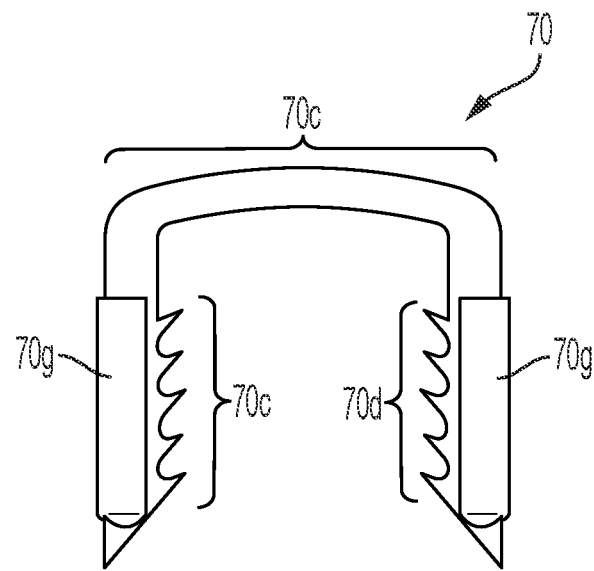
FIGS. 65a and 65b show respectively a frontal view and a top plan view of a flexible surgical staple in accordance with one embodiment of the invention.
Figure 65B:
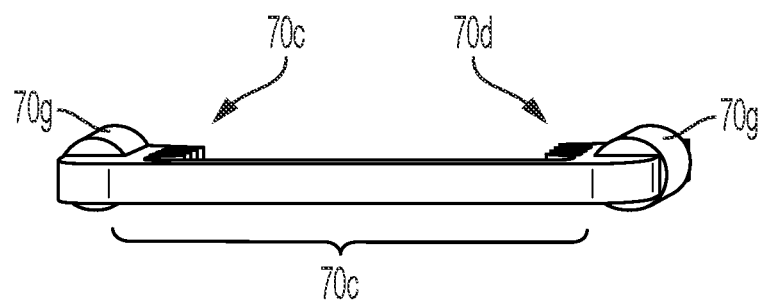

FIGS. 64b, 65a and 65b show lateral perspective, elevation, and plan views of a flexible surgical staple in accordance with one embodiment of the invention. FIG. 64b shows surgical staple 70 having staple legs 70a and 70b and staple bridge portion 70c. Flexible staple legs 70a and 70b are provided with one or more inwardly directed barbs 70d and 70e that permit insertion while securing the staple 70 in place in the tissue once the flexible staple 70 is in its relaxed compressed state. The staple legs may also be provided with supplemental three-dimensional features, such as cylindrical section portions 70g to permit the opposed channels (such as 3c and 3d or 13c and 13d, that may have rounded interior surfaces) to better accommodate the staple legs 60a and 60b to better maintain them in an expanded position prior to release.

Figure 66A:
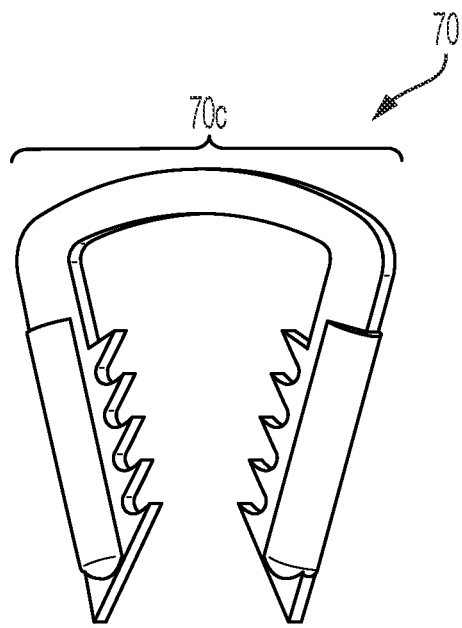
FIG. 66a shows a lateral perspective view of a flexible surgical staple in accordance with one embodiment of the invention.

FIG. 66a shows a lateral perspective view of a flexible surgical staple in accordance with one embodiment of the invention. This Figure shows surgical staple 70 having staple legs 70a and 70b in a compressively relaxed state as would appear once inserted into tissue.

Figure 66B:
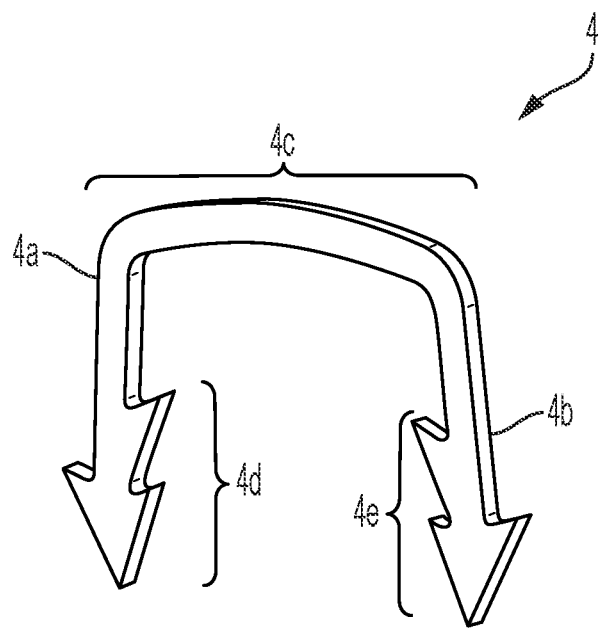
FIG. 66b shows a lateral perspective view of a flexible surgical staple in accordance with one embodiment of the invention.

FIG. 66b shows a lateral perspective view of a flexible surgical staple in accordance with one embodiment of the invention. This Figure shows surgical staple 4 having staple legs staple legs 4a and 4b, while staple bridge portion 4c is held in a relatively compressed state, as shown by directional arrows, such that the staple legs 4a and 4b are maintained aligned with respective insertion needle portions 3a and 3b. In this position the flexible staple is in a loaded compressed state so that it may be inserted into tissue at sufficient depth to approximate the tissue. Flexible staple legs 4a and 4b are provided with one or more outwardly directed barbs 4d and 4e that permit insertion while securing the flexible staple 4 in place in the tissue once the flexible staple 4 is permitted to expand once inserted into tissue.

Figure 67A:
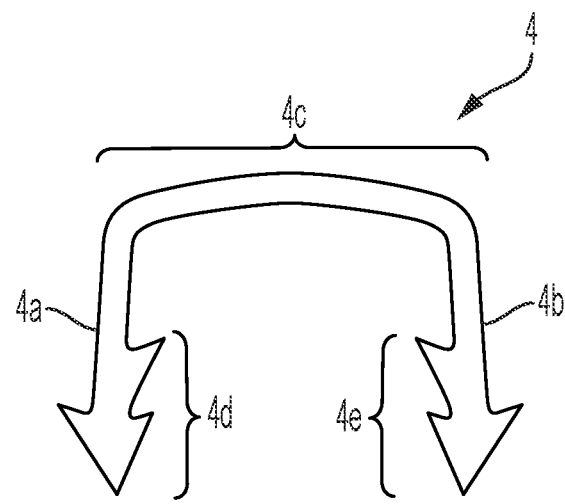
FIGS. 67a and 67b show respectively a frontal view and a lateral perspective view of a flexible surgical staple in accordance with one embodiment of the invention.
Figure 67B:
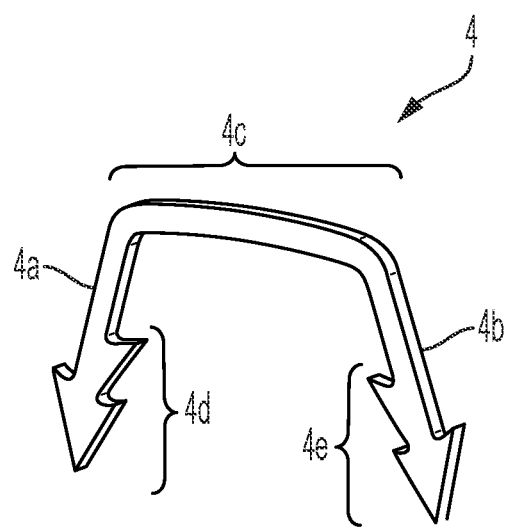
Figure 68A:
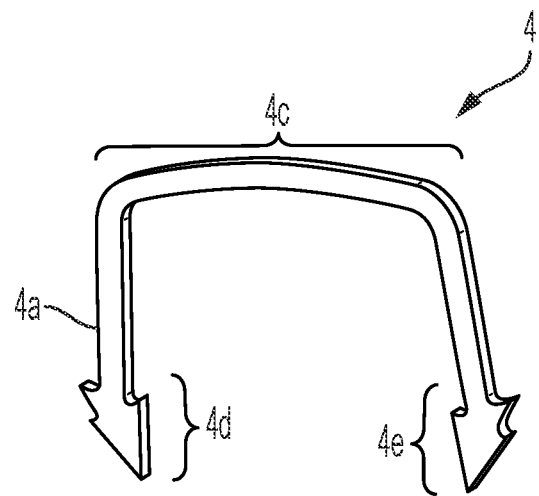
FIGS. 68a and 68b show lateral perspective views of a flexible surgical staple in accordance with one embodiment of the invention.
Figure 68B:
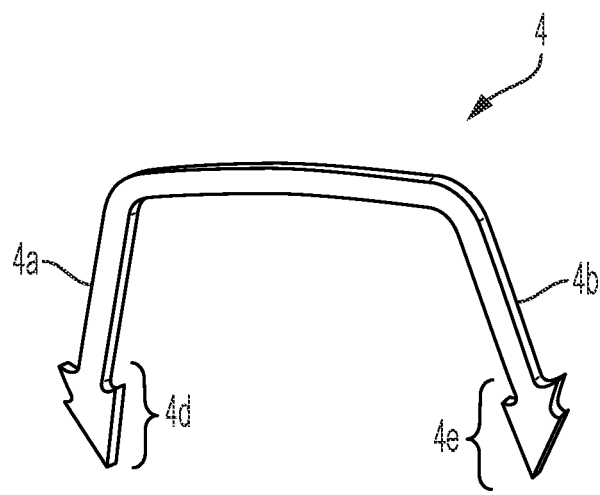

FIGS. 67a and 67b show respectively a frontal view and a lateral perspective view of a flexible surgical staple 4 in accordance with one embodiment of the invention as held compressed during insertion, while FIGS. 68a and 68b show lateral perspective views of a flexible surgical staple 4 (as released following insertion) in accordance with one embodiment of the invention, and wherein like numerals refer to identified features.

It will be appreciated that the handle, insertion portion, the anchor delivery portion, and the anchors may be produced from any material appropriate to the intended use whether sterile or non-sterile (i.e., for uses other than surgery or treatment, such as taxidermy or post-mortem use), and with due regard to disposability where desired. For instance, the handle, insertion portion, and the anchor delivery portion may be produced from metal, such as medical grade aluminum, while the handle portion may be produced from metal or plastics commonly used in medical devices, typically disposable ones.

The surgical staples, surgical staple placement devices and surgical staple placement and tissue approximation methods of the present invention may be applied to any surgical procedure that may include, benefit from or require tissue approximation or fixation, including without limitation procedures prone to seromas including various forms of plastic surgery, large tumor resections, and procedures involving repositioning of major organs. The most common types of surgery that result in seromas include breast procedures, abdominoplasty, body contouring and hernia repair. Other procedures where the present inventions may be advantageously applied include those where tissue approximation is required following the use of a trocar, such as procedures involving trocar placement through the abdomen during laparoscopic surgery. Still other procedures may be those involving tissue approximation associated with securing grafts and implants. In addition to the closure of dead space internally, there also exists a need for rapid and accurate closure of skin and dermis more superficially. The ability to prevent dehiscence of surgical incisions frequently relies upon meticulous repair of the dermal and subcuticular layer, which are the source of strength in surgical closure sites.

There exists a need to be able to apply independent and accurate staple placement in rapid fashion within the dermis and/or subcuticular plane to facilitate quicker and more reliable tissue approximation and wound closure.

The tissues that may be approximated through use of the subject surgical staples, suture placement devices, and suture placement and tissue approximation methods may include tissues of any type having two or more generally opposed or adjacent portions that may be advantageously drawn together to a desired position.

It will be appreciated that the present invention may be applied to other fields for the tissue approximation, adjoining and fixture, such as in veterinary medicine, or providing embalming or taxidermy services, and the like.

Figure 69:
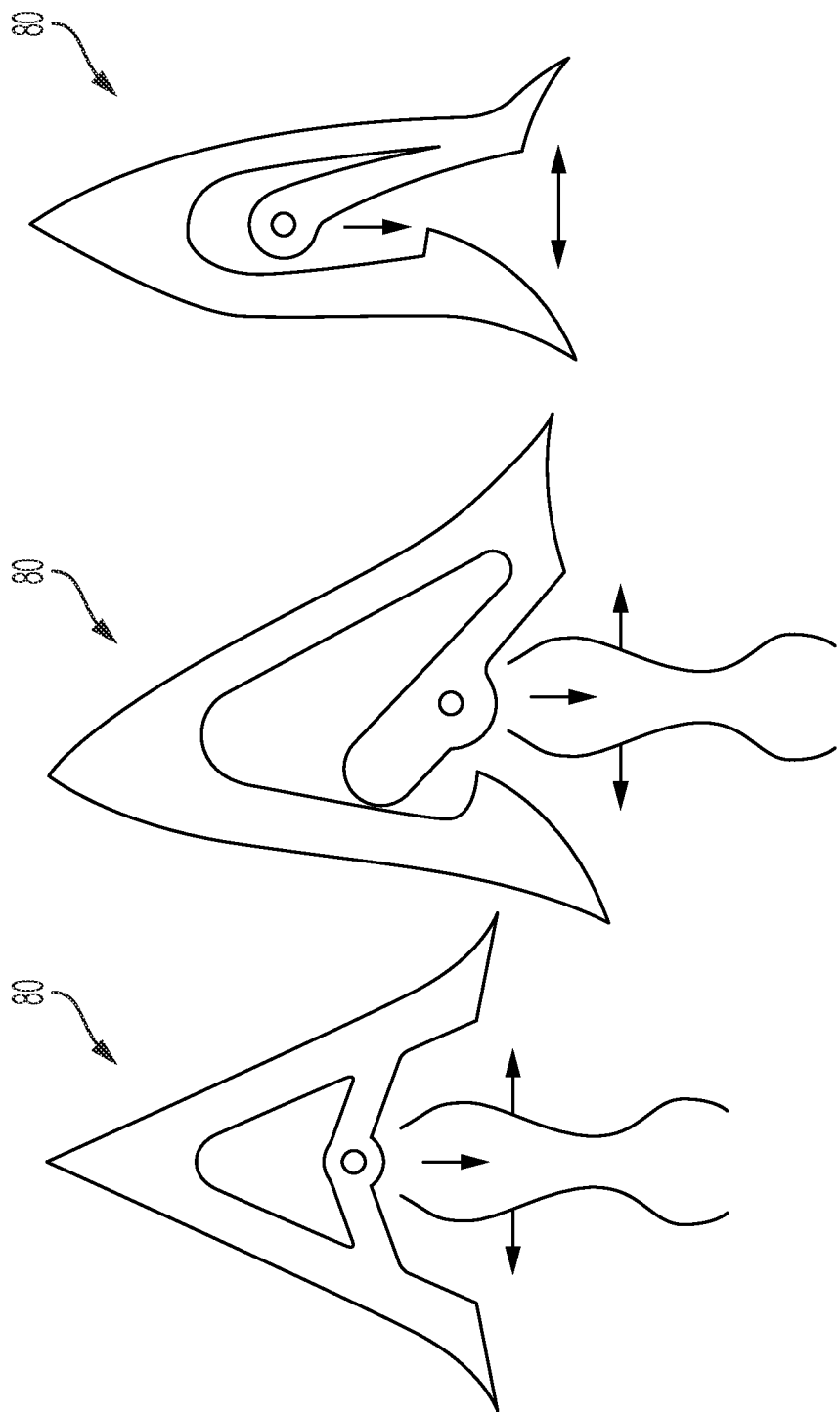
FIG. 69 shows an elevation view of expandable arrows which can be actuated by applying tension to the suture after insertion in the tissue.

FIG. 69 show expandable arrows which can be actuated by applying tension to the suture after insertion in the tissue such as for use with the suture material, such as suture 22, in accordance with the use of the staples for tissue approximation.

The present invention also includes arrangements to address the movement of tissue in respond to the straight and pre-tensioned staples.

Figure 70:
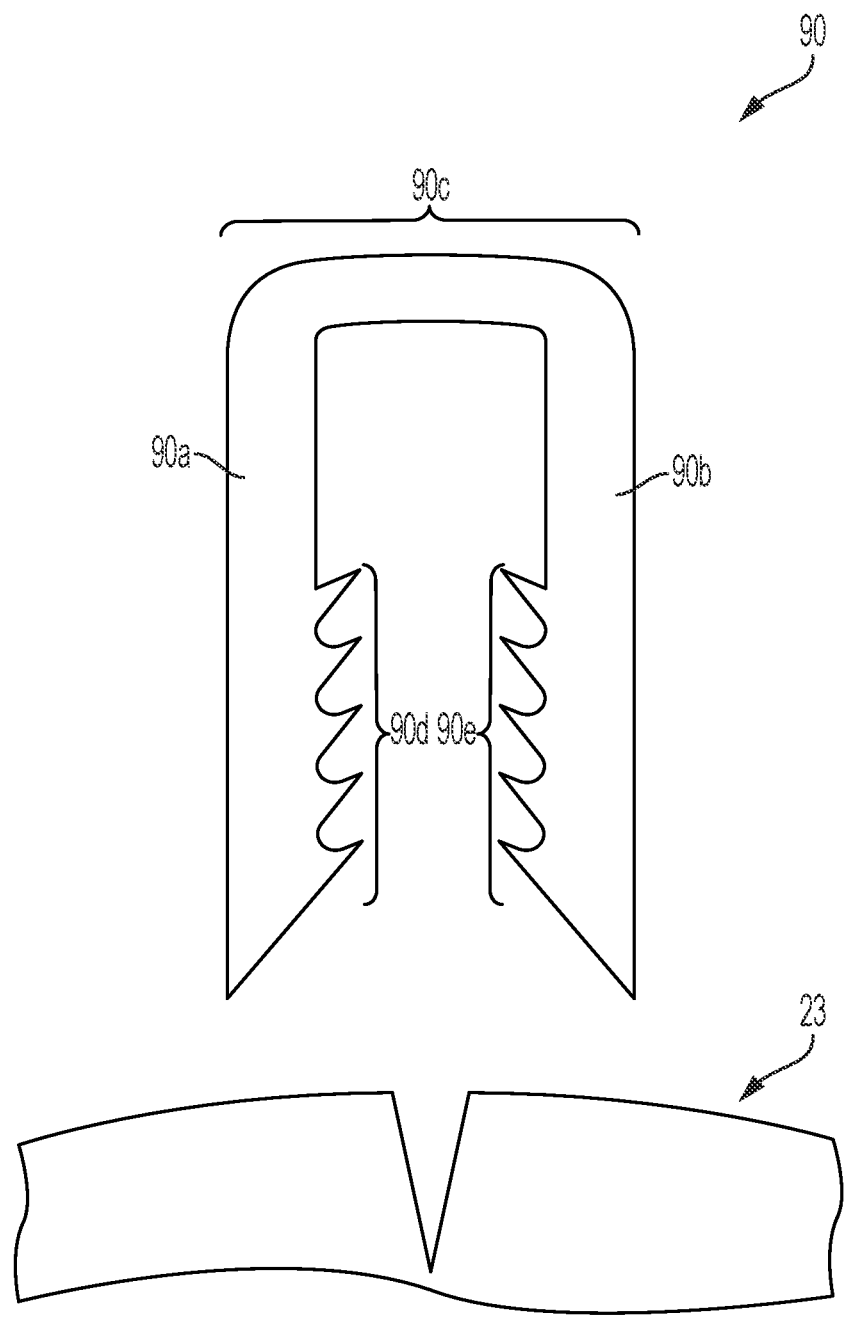
FIG. 70 shows an elevation view of a surgical staple in accordance with one embodiment of the invention.
Figure 71:
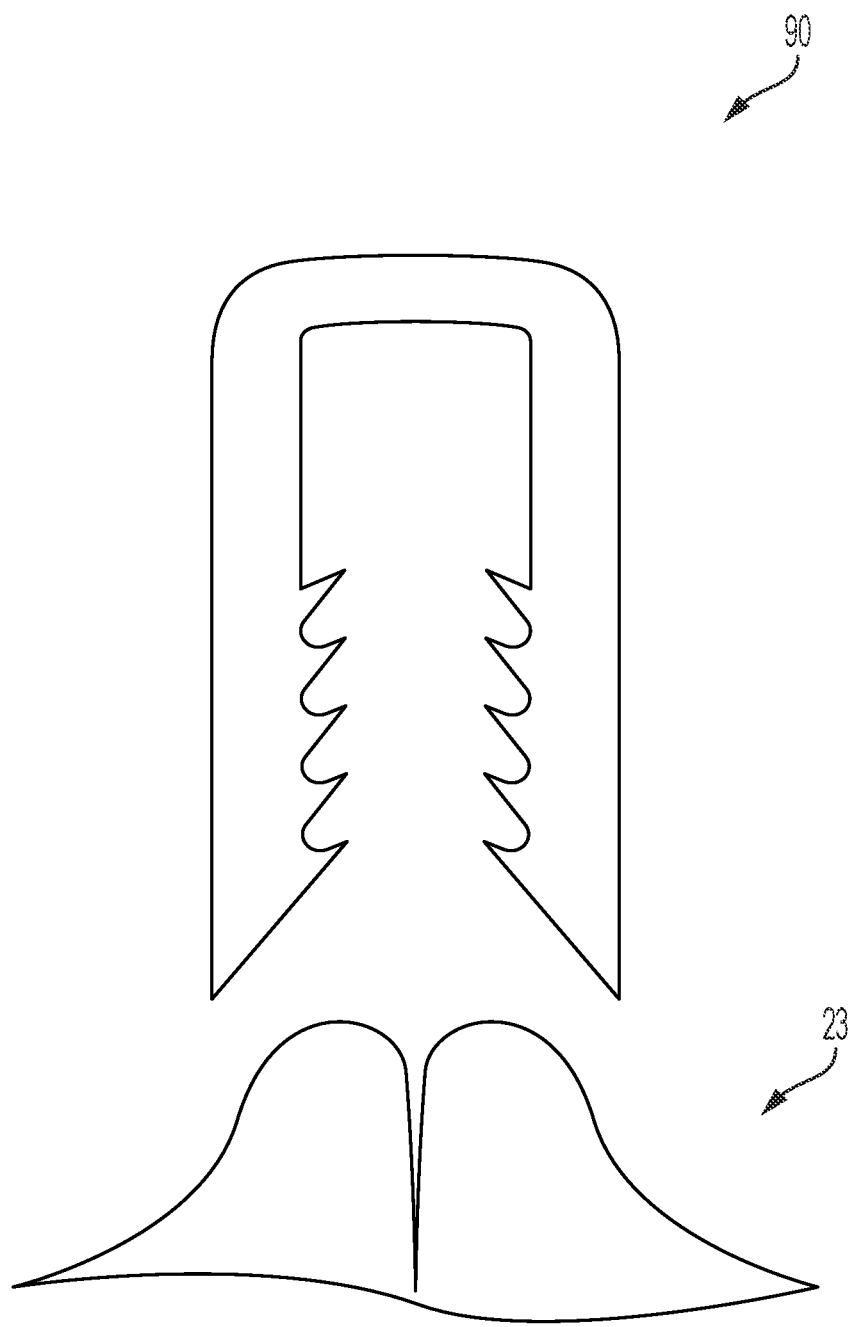
FIG. 71 shows an elevation view of a surgical staple in accordance with one embodiment of the invention.
Figure 72:
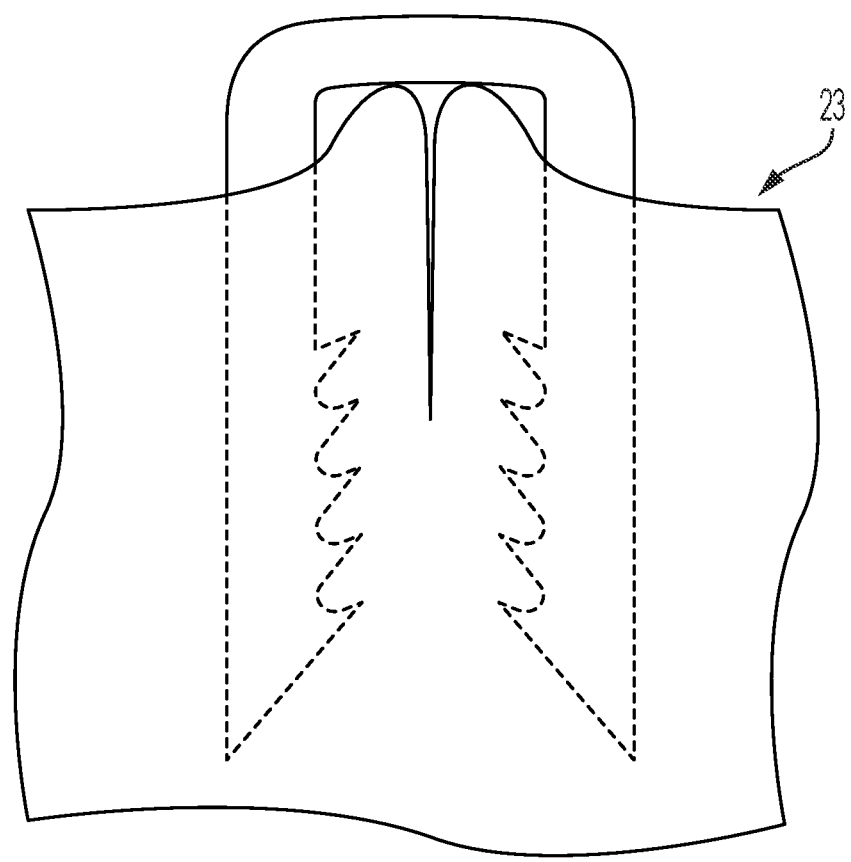
FIG. 72 shows an elevation view of a surgical staple in accordance with one embodiment of the invention.

FIGS. 70-72 are a series of views showing how a straight staple 90 may be inserted into tissue 23 such as through manual or tool manipulation manually or with a tool as is known in the art. These Figures show staple 90 having staple legs 90a and 90b and staple bridge portion 90c. Staple legs 90a and 90b are provided with one or more inwardly directed barbs 90d and 90e that permit insertion while securing the staple 90 in place in the tissue 23 that has been manually approximated.

Figure 73:
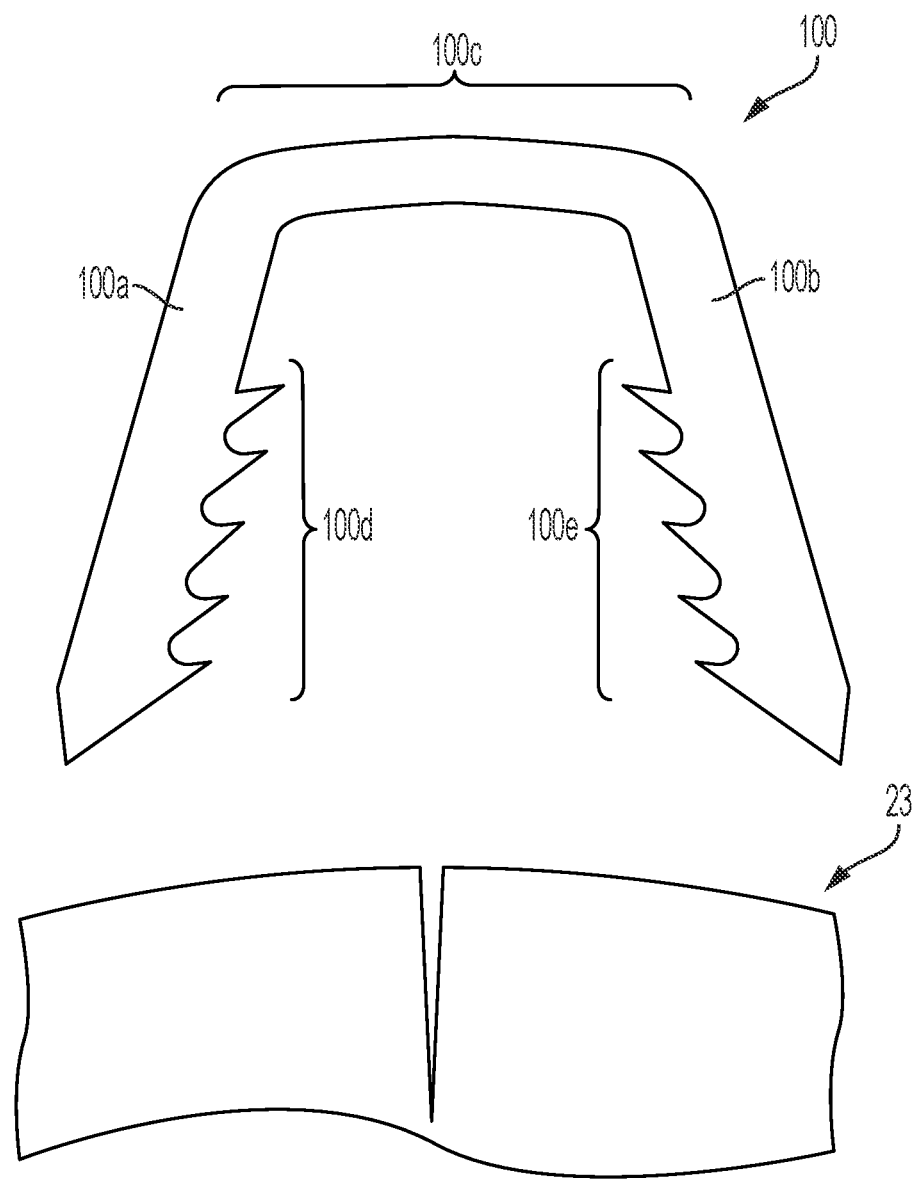
FIG. 73 shows an elevation view of a surgical staple in accordance with one embodiment of the invention.
Figure 74:
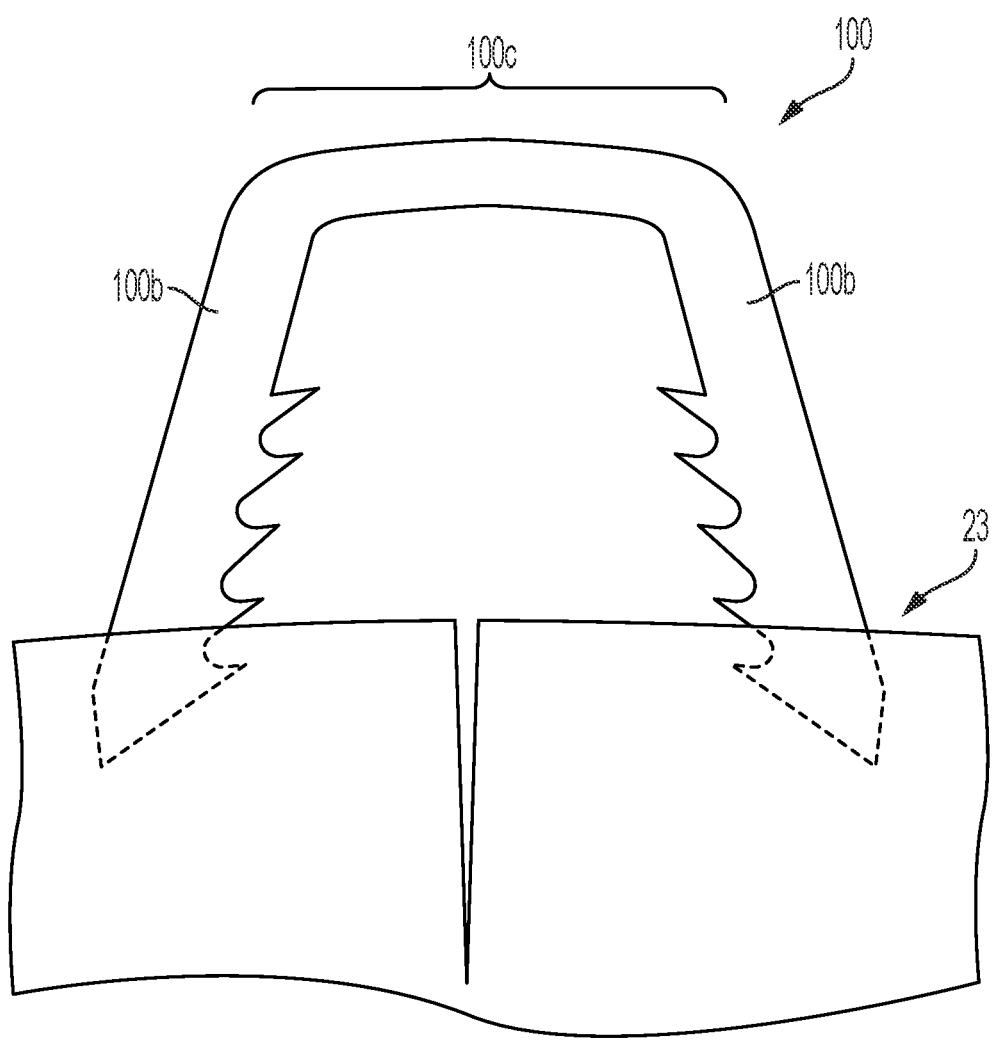
FIG. 74 shows an elevation view of a surgical staple in accordance with one embodiment of the invention.
Figure 75:
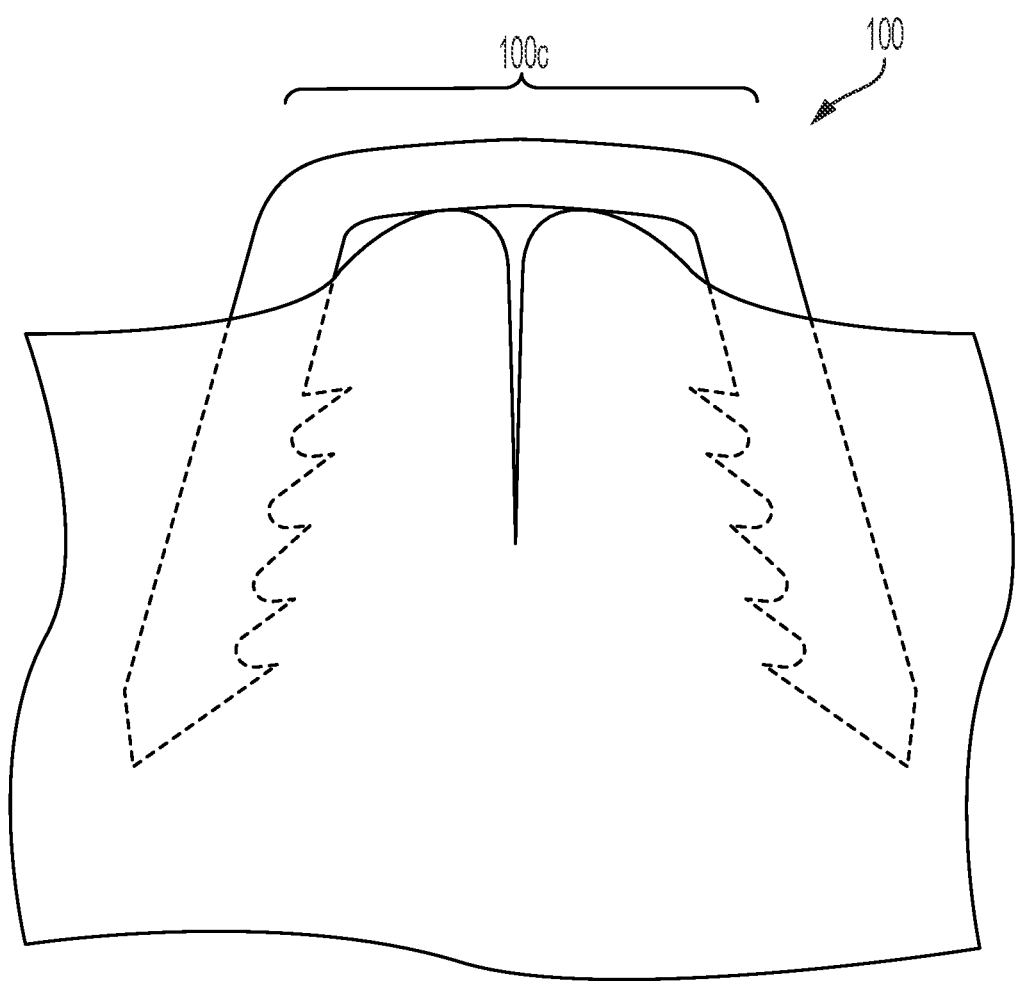
FIG. 75 shows an elevation view of a surgical staple in accordance with one embodiment of the invention.

Progressive FIGS. 73-75 show a tapered self-approximating staple 100 having staple legs 100a and 100b and staple bridge portion 100c. Staple legs 100a and 100b are provided with one or more inwardly directed barbs 100d and 100e that permit insertion while securing the staple 100 in place in the tissue 23 that has been manually approximated. The taper of the staple legs 100a and 100b causes the tissue to approximate as the legs converge during insertion toward the staple bridge portion 100c.

Figure 76:
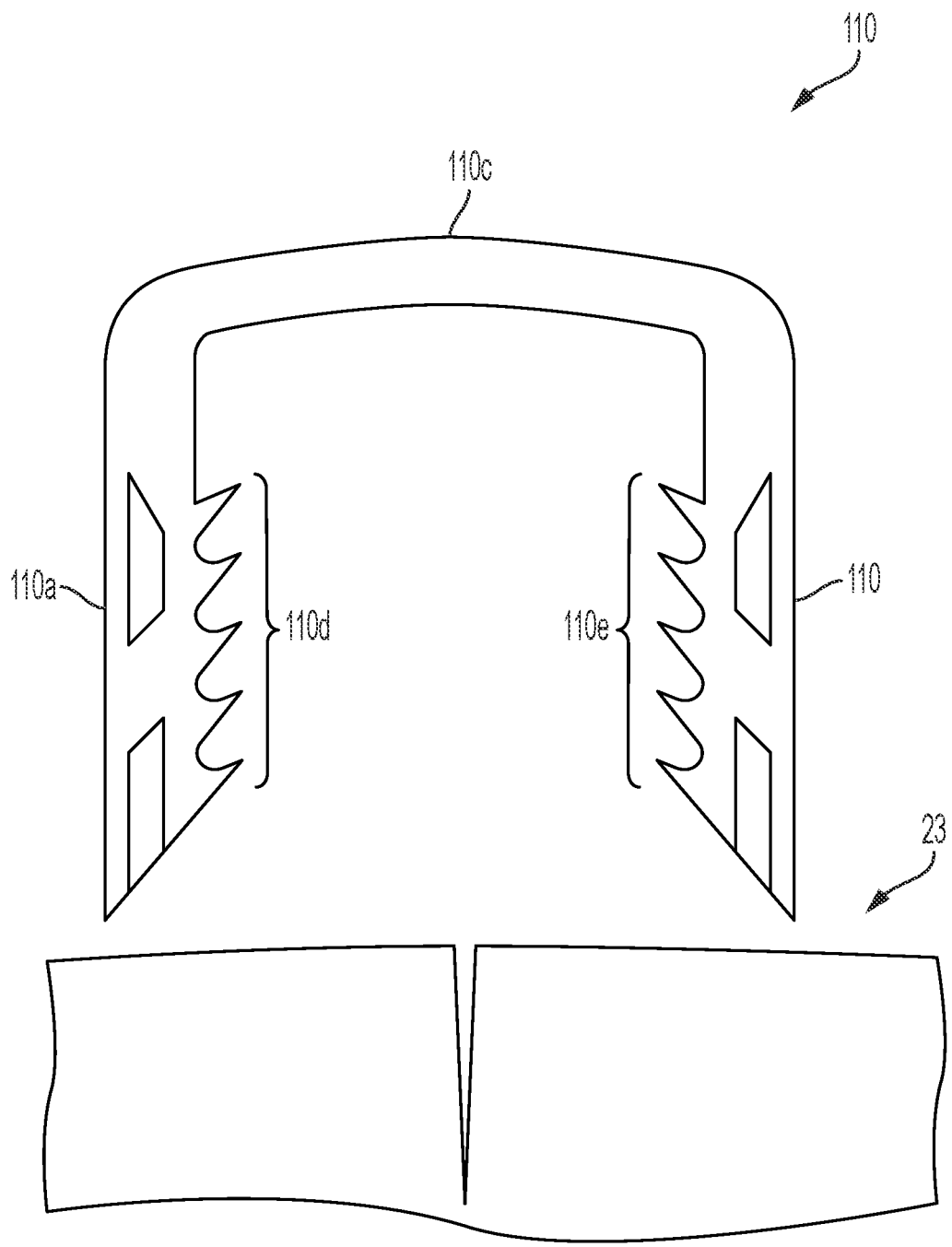
FIG. 76 shows an elevation view of a flexible surgical staple in accordance with one embodiment of the invention.
Figure 77:
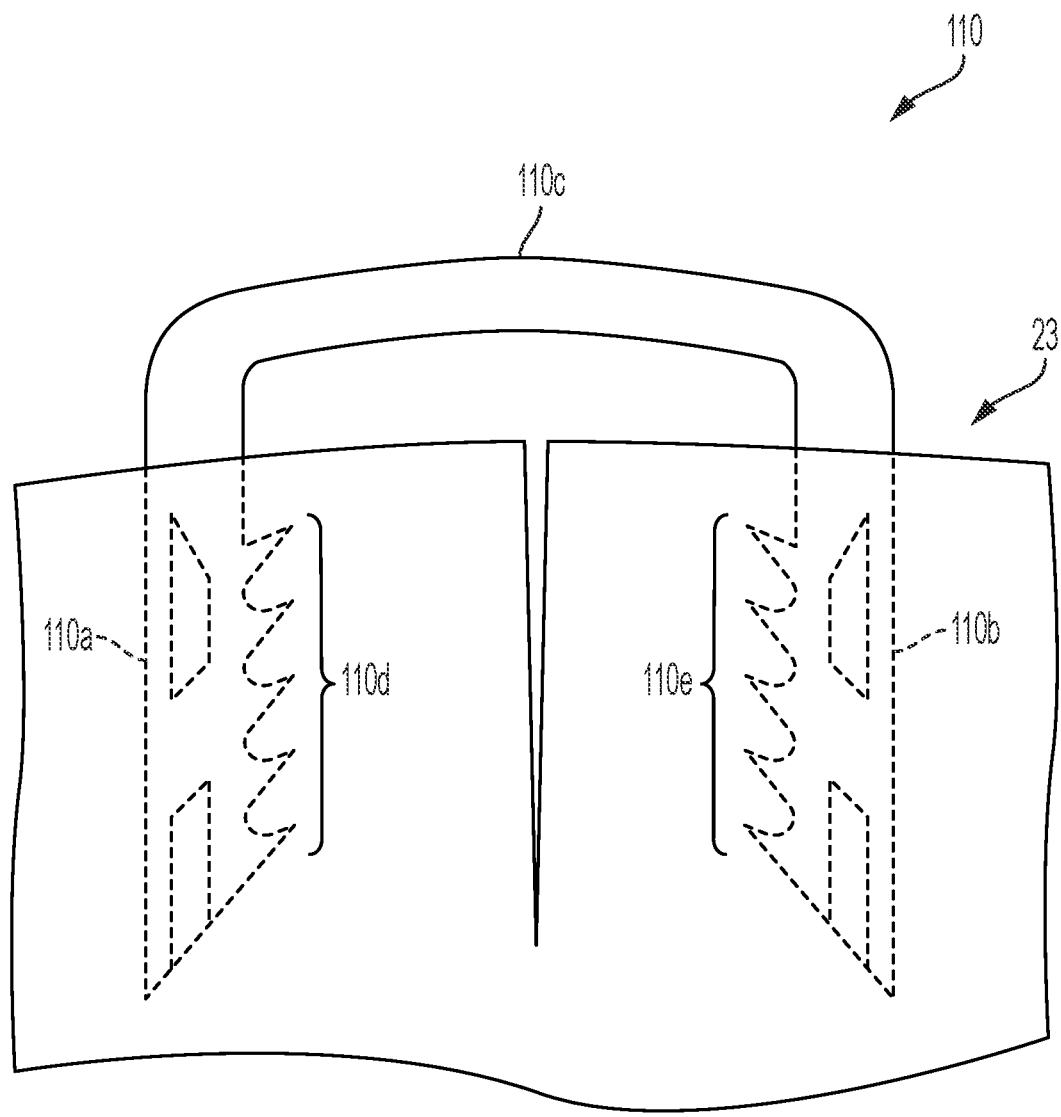
FIG. 77 shows an elevation view of a flexible surgical staple in accordance with one embodiment of the invention.
Figure 78:
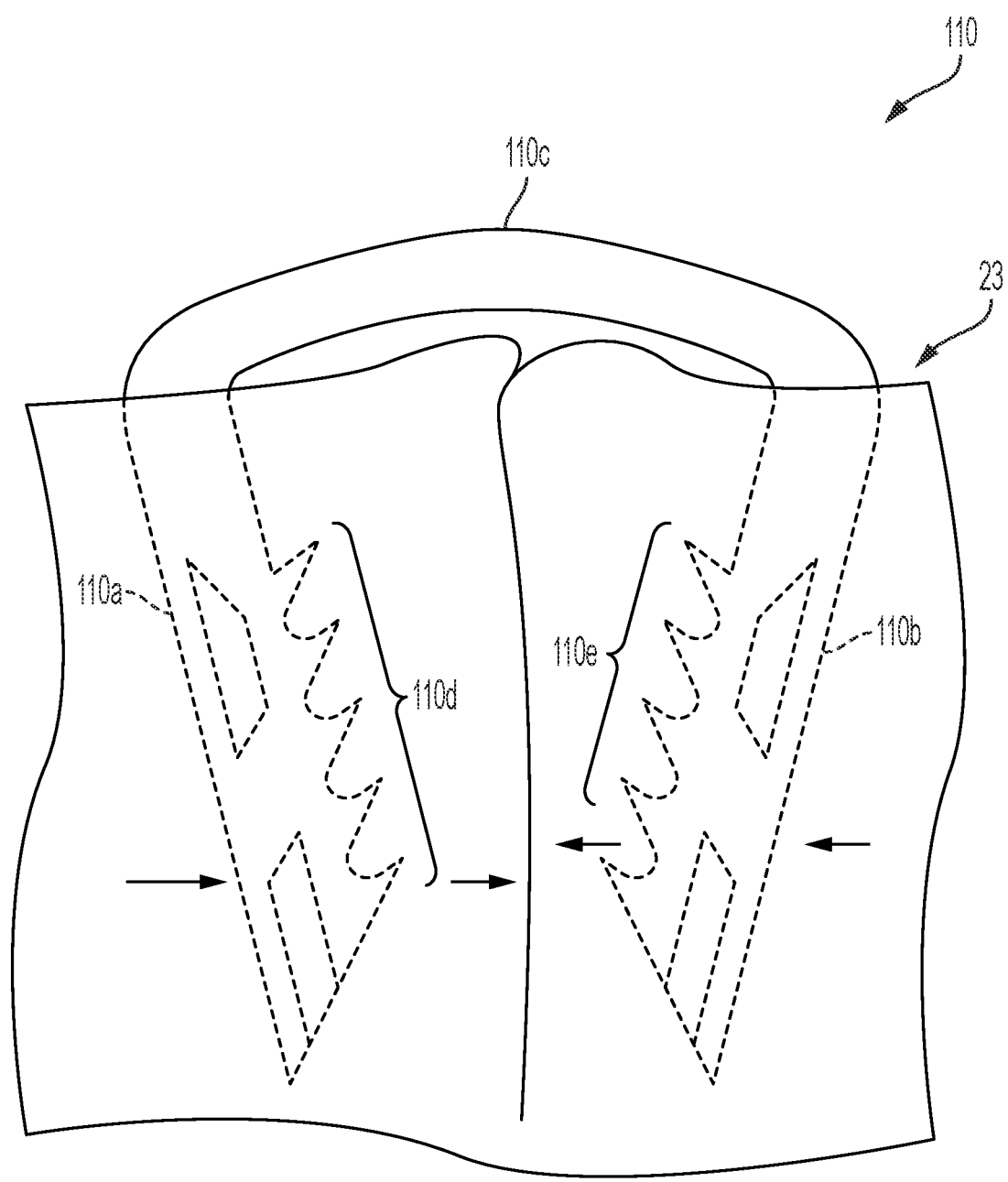
FIG. 78 shows an elevation view of a flexible surgical staple in accordance with one embodiment of the invention.

Progressive FIGS. 76-78 show a pre-tensioned surgical staple 110 which collapses when released from the handle thus causing the tissue 23 to approximate, as shown in this series of Figures. Staple 110 has staple legs 110a and 110b and staple bridge portion 110c. Staple legs 110a and 110b are provided with one or more inwardly directed barbs 110d and 110e that permit insertion while securing the staple 110 in place in the tissue 23 that has been manually approximated. Staple 110 is tensioned in the delivery device so as to collapse inward upon insertion and release from the insertion device into tissue 23.

Figure 79A:
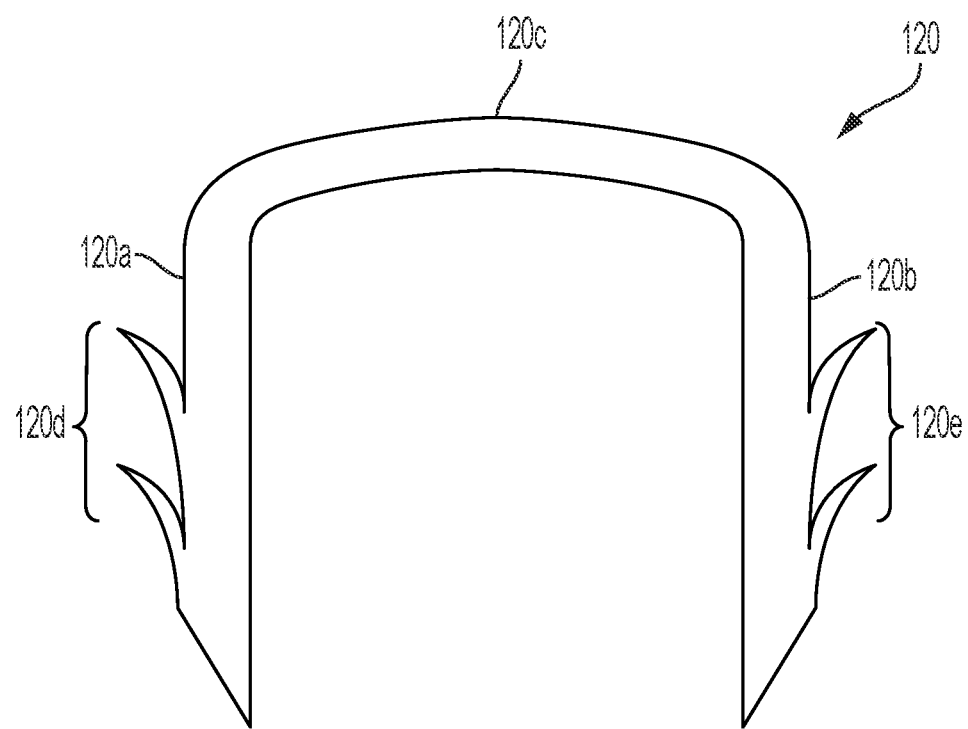
FIG. 79a shows an elevation view of a surgical staple in accordance with one embodiment of the invention.

FIG. 79a shows a surgical staple 120 having staple legs 120a and 120b and staple bridge portion 120c. Staple legs 120a and 120b are provided with one or more flexible outwardly directed barbs 120d and 120e that may be molded as part of respective staple legs 120a and 120b or be cut out post-molding. Outwardly directed barbs 120d and 120e are sufficiently flexible to flex in response to insertion into tissue, to permit insertion while securing the staple 120 in place in the tissue 23 that has been manually approximated.

Figure 79B:
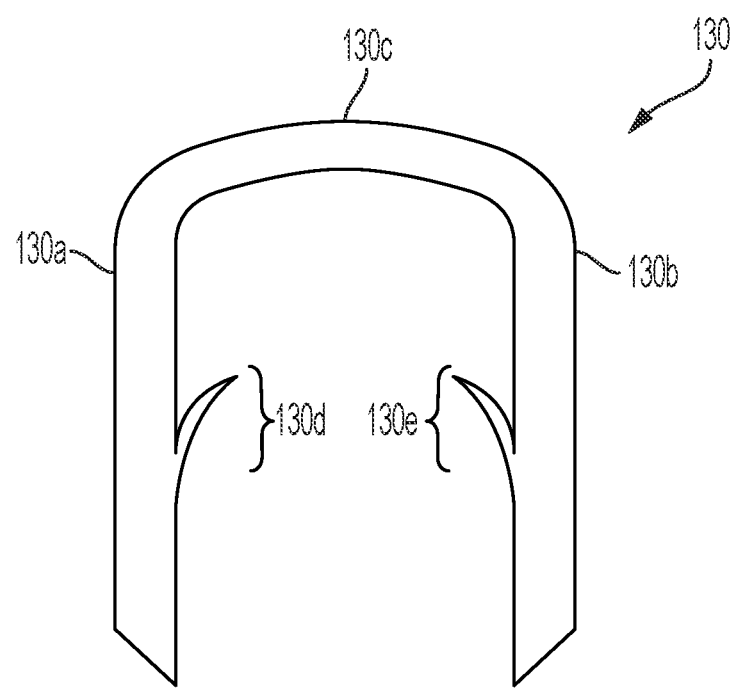
FIG. 79b shows an elevation view of a surgical staple in accordance with one embodiment of the invention.

FIG. 79b shows a surgical staple 130 having staple legs 130a and 130b and staple bridge portion 130c. Staple legs 130a and 130b are provided with one or more flexible inwardly directed barbs 130d and 130e that may be molded as part of respective staple legs 130a and 130b or be cut out post-molding.

Figure 80A:
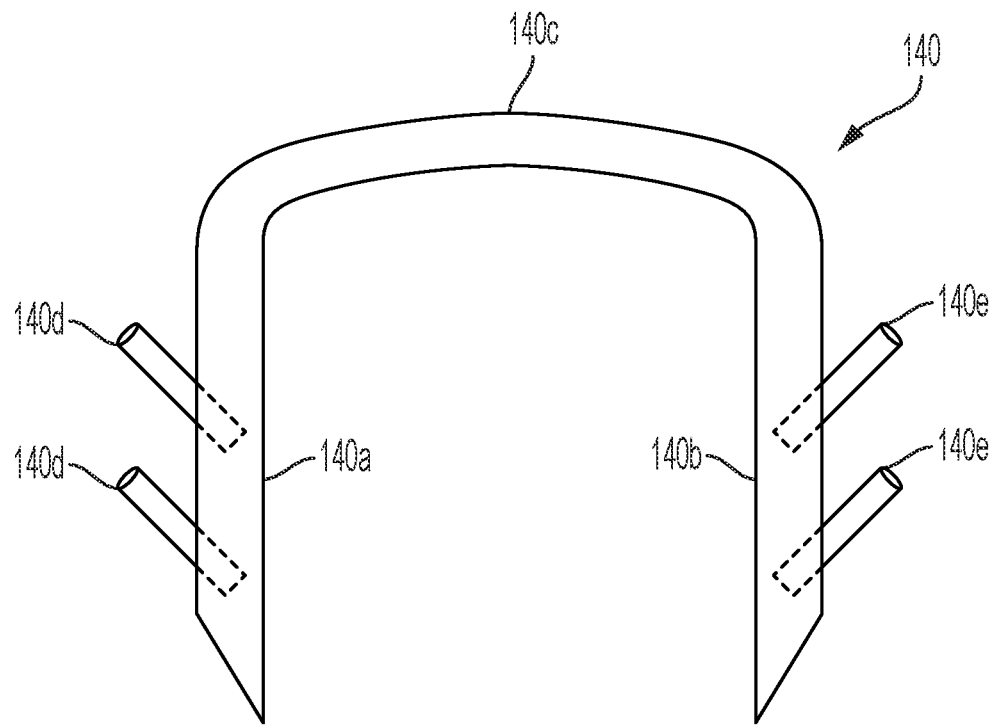
FIG. 80a shows an elevation view of a surgical staple in accordance with one embodiment of the invention.

FIG. 80a shows an elevation view of a surgical staple in accordance with one embodiment of the invention. FIG. 80a shows a surgical staple 140 having staple legs 140a and 140b and staple bridge portion 140c. Staple legs 140a and 140b are provided with one or more flexible outwardly directed suture material lengths 140d and 140e that may be molded as part of respective staple legs 140a and 140b or be inserted as separate pieces as shown, post-molding. Outwardly directed suture material lengths 140d and 140e are sufficiently flexible to flex in response to insertion into tissue, to permit insertion while securing the staple 140 in place in the tissue 23 that has been manually approximated. The suture material lengths 140d and 140e may be of a bioabsorbable material, while the surgical staple 140 may be of a bioabsorbable material or otherwise of a rigid material. In the embodiment wherein the suture material lengths 140d and 140e is of a bioabsorbable material while the surgical staple 140 is of a rigid material requiring subsequent removal, the suture may dissolve post-insertion, permitting relatively easy removal of the rigid staple by a straight pulling action.

Figure 80B:
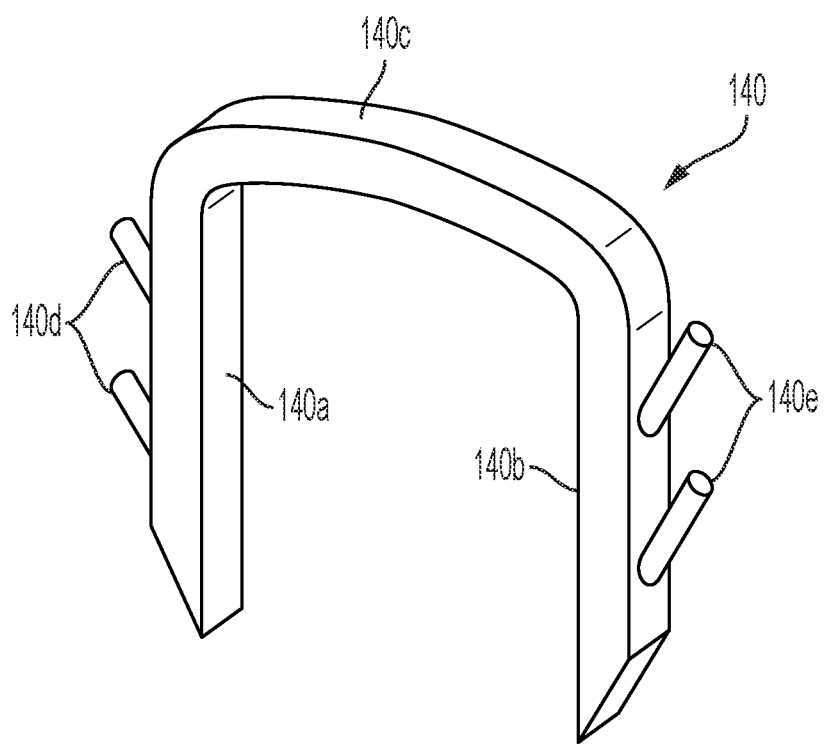
FIG. 80b shows a lateral perspective view of a surgical staple in accordance with one embodiment of the invention.

FIG. 80b shows a lateral perspective view of a surgical staple in accordance with one embodiment of the invention.

Figure 81A:
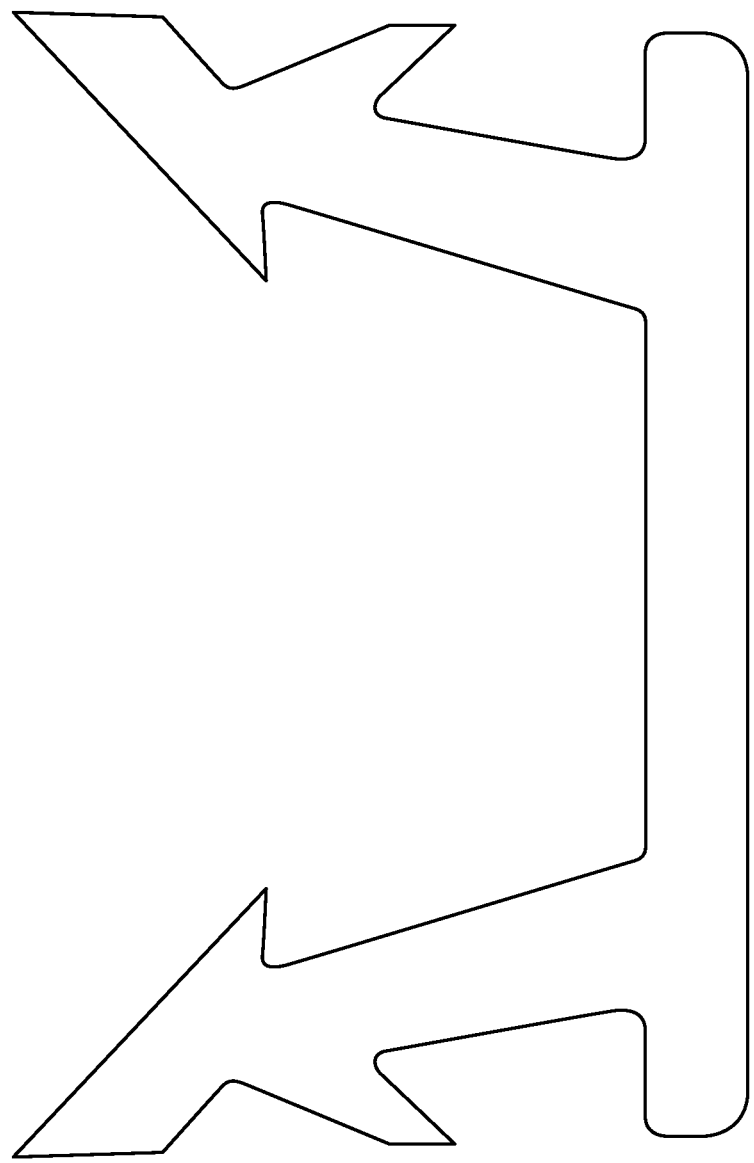
FIG. 81a shows an elevation view of a surgical staple in accordance with one embodiment of the invention.

FIG. 81a shows an elevation view of a surgical staple in accordance with one embodiment of the invention.

Figure 81B:
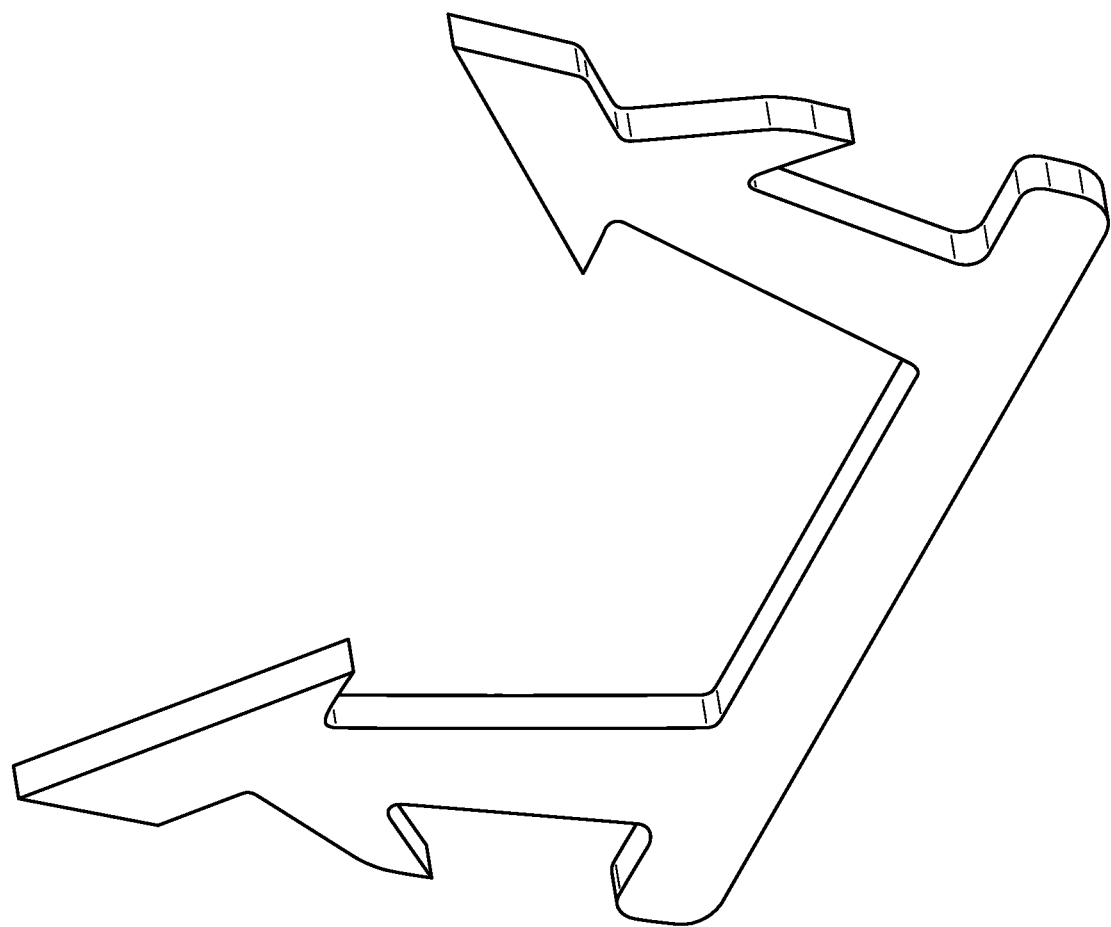
FIG. 81b shows a lateral perspective view of a surgical staple in accordance with one embodiment of the invention.

FIG. 81b shows a lateral perspective view of a surgical staple in accordance with one embodiment of the invention.

Figure 81C:
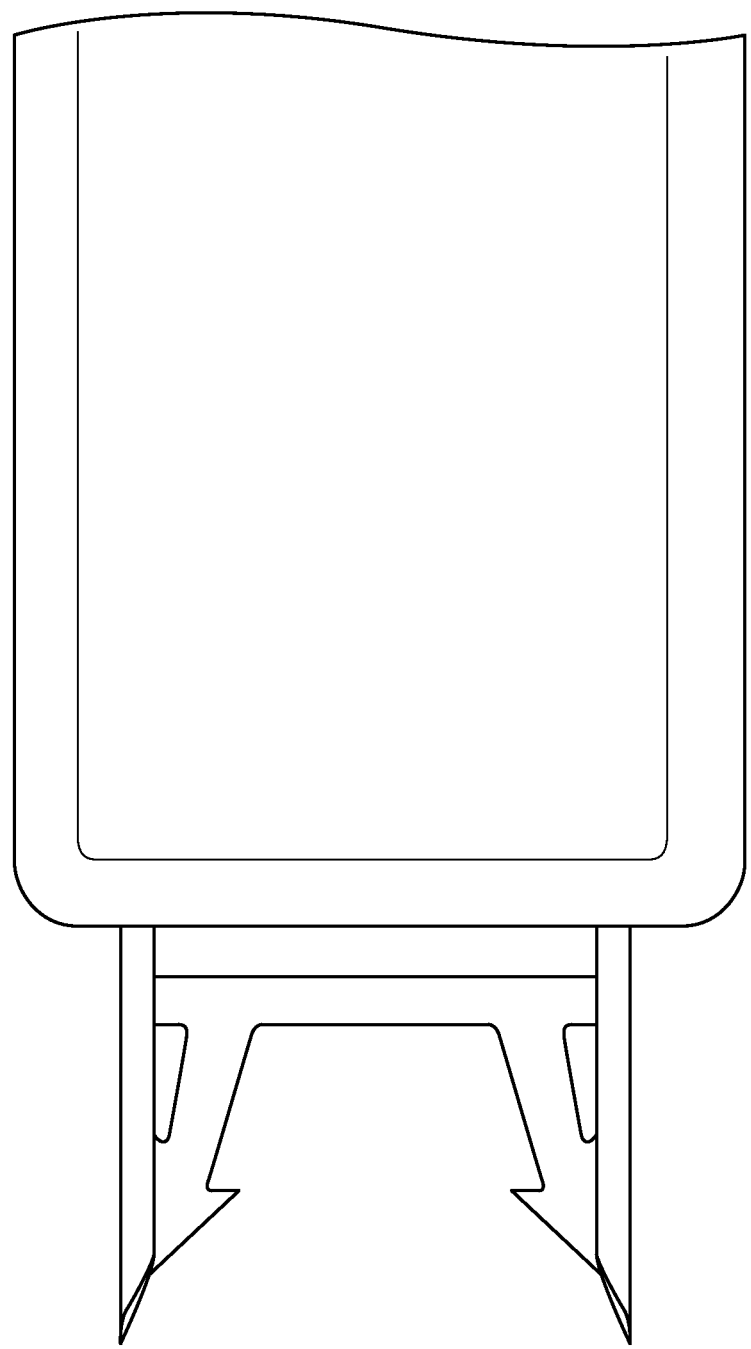
FIG. 81c shows an elevation view of a flexible surgical staple and staple insertion device in accordance with one embodiment of the invention.

FIG. 81c shows an elevation view of a flexible surgical staple and staple insertion device in accordance with one embodiment of the invention.

Figure 81D:
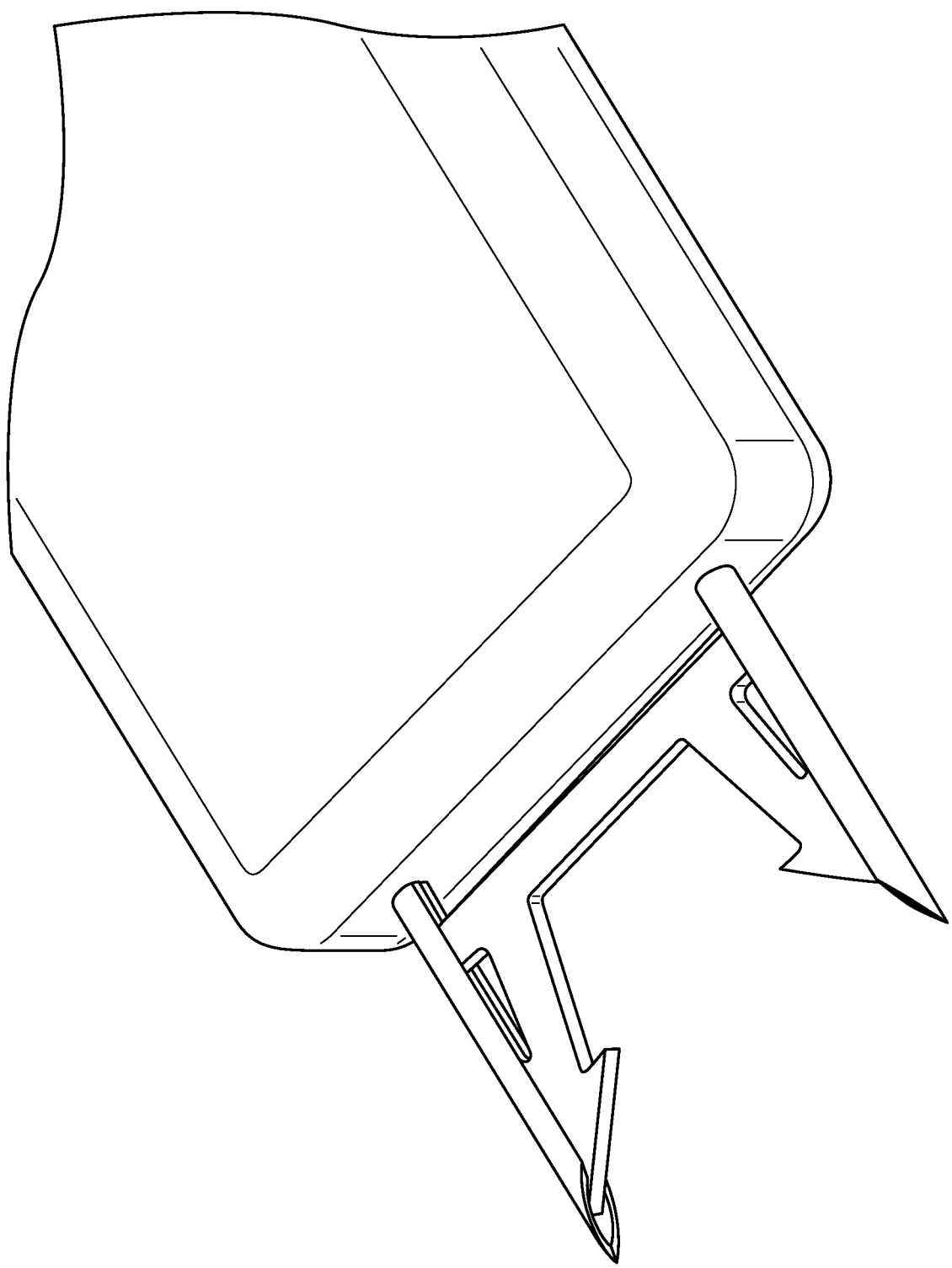
FIG. 81d shows a lateral perspective view of a flexible surgical staple and staple insertion device in accordance with one embodiment of the invention.

FIG. 81d shows a lateral perspective view of a flexible surgical staple and staple insertion device in accordance with one embodiment of the invention.

Notwithstanding that the numerical ranges and parameters setting forth the broad scope of the disclosure are approximations, any numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Other embodiments of the disclosure will be apparent to those skilled in the art from consideration of the specification and practice of the disclosure disclosed herein. It is intended that the specification and examples be considered as exemplary only, and that modifications may be made to the described embodiments without departing from the spirit and scope of the disclosure as defined in the claims.

What is claimed is:
1. A surgical staple comprising:
 a. a solid first leg for anchoring in a first tissue portion, a solid second leg for anchoring in a second tissue portion, and an elastically deformable bridge monolithically formed with the first leg and the second leg; the solid first leg and the solid second leg each forming respective angles greater than 90 degrees with respective portions of said elastically deformable bridge when said surgical staple is in an open, uncompressed state, said elastically deformable bridge of sufficient elasticity so as to permit said first leg and the second leg to be urged from an open, uncompressed state angled position to a substantially parallel position; and
 b. each of said solid first leg and said solid second leg having a terminal end each comprising a distally directing point, such that, said solid first leg and said solid second leg have been urged into said substantially parallel position, said distally directing points are directed substantially orthogonal to said elastically deformable bridge; and each said terminal end having respective interior and exterior lateral sides, each said interior lateral side comprising an interior lateral barb directed at an angle to said respective leg, and each said exterior lateral side comprising an exterior lateral barb directed at an angle to said respective leg.

2. A surgical staple according to claim 1 wherein each of said solid first leg and said solid second leg each additionally comprise a channel engagement extension portion extending from the respective lateral sides thereof.

3. A surgical staple according to claim 1 wherein each of said solid first leg and said solid second leg additionally comprise a channel engagement extension portion extending from the respective lateral sides thereof, said channel engagement extension portion having a curved surface.

4. A surgical staple comprising:
   a. a flexible staple bridge of a flexible resorbable suture material; and
   b. a pair of staple legs extending from said staple bridge, the staple legs adapted to be moved from a relatively compressed state wherein said staple legs are substantially parallel to a relatively expanded state, and wherein each of said staple legs additionally comprising interior lateral sides each comprising a lateral side barb directed at an angle to said lateral side, and exterior lateral sides each comprising an exterior lateral barb directed at an angle to said exterior lateral side, said lateral barbs shaped so as to resist the withdrawal from tissue once placed into tissue once the staple legs are inserted into tissue.

5. A surgical staple according to claim 4 wherein each of said first leg and said second leg each additionally comprise a channel engagement extension portion extending from the respective lateral sides thereof.

6. A surgical staple according to claim 4 wherein each of said first leg and said second leg additionally comprise a channel engagement extension portion extending from the respective lateral sides thereof, said channel engagement extension portion having a curved surface.

7. A staple insertion device comprising:
   a) a handle portion; and
   b) substantially parallel insertion portions extending from said handle, said insertion portions each having an interior lateral channel, and each insertion portion having a terminal sharp point adapted to pierce tissue; the insertion portions adapted to slidingly engage a flexible staple, and to completely contain the length of said flexible staple therebetween, said flexible staple comprising:
   i. a solid first leg for anchoring in a first tissue portion, a solid second leg for anchoring in a second tissue portion, and an elastically deformable bridge monolithically formed with the first leg and the second leg; the solid first leg and the solid second leg each forming respective angles greater than 90 degrees with respective portions of said elastically deformable bridge, said elastically deformable bridge of sufficient elasticity so as to permit said first leg and the second leg to be urged from an opened angled position to a substantially parallel position; and
   ii. each of said solid first leg and said solid second leg having a terminal end each comprising a distally directing point, such that, said solid first leg and said solid second leg have been urged into said substantially parallel position, said distally directing points are directed substantially orthogonal to said elastically deformable bridge; and each said terminal end having interior and exterior lateral sides each comprising a lateral barb extending therefrom and directed at an angle to said respective leg.

8. A staple insertion device according to claim 7 wherein said substantially parallel insertion portions extend into said handle and are adapted to guide said flexible staple from a position within said handle to a position at the distal end of said parallel insertion portions.

9. A staple insertion device according to claim 8 wherein said substantially parallel insertion portions define a path along which a flexible staple may be urged such that, as said flexible staple is urged from a position within said handle toward a position at the distal end of said parallel insertion portions, said flexible staple is deformed from a relatively expanded state to a relatively compressed state.

10. A staple insertion device according to claim 7, additionally comprising a cartridge adapted to supply flexible staples in a series to said position within said handle.

* * * * *